US012714696B2

(12) United States Patent
Gruet

(10) Patent No.: US 12,714,696 B2
(45) Date of Patent: Aug. 25, 2026

(54) LOW DOSE FLURALANER COMPOSITIONS FOR PROTECTION AGAINST PARASITIC INVERTEBRATE PEST

(71) Applicant: VIRBAC, Carros (FR)

(72) Inventor: Philippe Gruet, Carros (FR)

(73) Assignee: VIRBAC, Carros (FR)

( * ) Notice: Subject to any disclaimer, the term of this patent is extended or adjusted under 35 U.S.C. 154(b) by 0 days.

(21) Appl. No.: 17/601,016

(22) PCT Filed: Apr. 2, 2020

(86) PCT No.: PCT/EP2020/059429
§ 371 (c)(1),
(2) Date: Oct. 1, 2021

(87) PCT Pub. No.: WO2020/201440
PCT Pub. Date: Oct. 8, 2020

(65) Prior Publication Data

US 2022/0168278 A1 Jun. 2, 2022

Related U.S. Application Data

(60) Provisional application No. 62/828,911, filed on Apr. 3, 2019.

(51) Int. Cl.
*A61K 31/42* (2006.01)
*A61P 33/00* (2006.01)

(52) U.S. Cl.
CPC .............. *A61K 31/42* (2013.01); *A61P 33/00* (2018.01)

(58) Field of Classification Search
CPC ................................ A61K 31/42; A61P 33/00
See application file for complete search history.

(56) References Cited

FOREIGN PATENT DOCUMENTS

| | | | |
|---|---|---|---|
| EP | 3351243 | * | 7/2018 |
| EP | 33451243 | * | 7/2018 |
| WO | 2015/091900 | A1 | 6/2015 |
| WO | WO 2015/091900 | * | 6/2015 |

OTHER PUBLICATIONS

Kilp et. al. (Parasites and Vectors (2014) 7:1-5,) (Year: 2014).*
Rohdich et. al. (Parasites and Vectors (2014) 7:83 pp. 1-5). (Year: 2014).*
Kilp et. al. (Parasites and Vectors (2014) 7:85 pp. 1-5). (Year: 2014).*
Perez-Sanchez, R., et al., "Acaricidal activity of fluralaner against Omithodoros moubata and Omithodoros erraticus argasid ticks evaluated through in vitro feeding," Veterinary Parasitology: 243 (2017) pp. 119-124.
International Search Report and Written Opinion mailed Jul. 9, 2020, issued in corresponding International Application No. PCT/EP2020/059429, filed Apr. 2, 2020, 15 pages.
Kilp, S., et al., "Pharmacokinetics of fluralaner in dogs following a single oral or intravenous administration," Parasites and Vectors: vol. 7, No. 1, Mar. 7, 2014.

* cited by examiner

*Primary Examiner* — Marcos L Sznaidman
(74) *Attorney, Agent, or Firm* — CHRISTENSEN O'CONNOR JOHNSON KINDNESS PLLC

(57) ABSTRACT

Low doses of fluralaner or another isoxazoline derivative are administered to an animal such as a pet, typically a dog or a cat, preferentially by administration of a repeated dose, at regular intervals or at varying intervals, each dose being of the same or different amount, which leads to efficacy against arthropods, especially fleas and ticks. Various regimens, galenic forms, posologies, therapeutic indications, combinations with other active or synergistic ingredients, and smart devices or methods for release of doses to the animal can be provided, alone or in combinations.

12 Claims, 5 Drawing Sheets

LOW DOSE FLURALANER COMPOSITIONS FOR PROTECTION AGAINST PARASITIC INVERTEBRATE PEST

The present invention relates to low dose isoxazoline compositions and methods of administration.

BACKGROUND ART

Current commercial compositions rely on dispensing a high dose of the isoxazoline compound. For example, a leading commercial composition Bravecto® is indicated to be applied at the dose of 25 mg/kg, in a single application for a duration of 3 months. Bravecto® contains fluralaner.

Another commercial composition Nexgard® is indicated to be applied at the dose of 2 to 3 mg/kg in a single application for a duration of 1 month. Nexgard® contains afoxolaner.

The publication Kilp (Parasite and vectors 2014, 7:85) provides a pharmacological profile of fluralaner to establish innocuity, for administered doses 12.5, 25, 50 mg/kg oral or 12.5 mg intravenous.

The publication *The effect of food on the pK of oral fluralaner* (Parasite and vectors 2014, 7:84) discloses an effect fed/fasted, wherein administration to the fed animal increased the AUC in the conditions of the testing.

The publication Comparative pK of fluralaner in dogs and cats, topical and iv (Parasite and vectors 2016, 9:296) reports testing on 24 dogs and cats, with low hepatic clearance. Doses tested included 12.5 to 50 mg/kg to dogs, and 20 to 80 mg/kg to cats. The AUC in cats was about half the AUC in dogs.

The publication Plasma pK fluralaner and ivermectin in dogs (Parasite and vectors 2015, 8:508) describes the absence of interference between fluralaner and ivermectin. The administered dose of fluralaner was 56 mg/kg.

No actual protection or treatment effect was tested in these publications.

Also, the publication WO2015/091900 discloses the use of isoxazoline derivatives for the treatment or prevention of arthropod infestations in poultry, wherein the effective amount is between 0.01 and 50 mg/kg body weight of animals treated. Mite control tests were performed on poultry was tested using a fluralaner dose of 10 μg/kg.

EP3351243A discloses an isoxazoline compound for use in protecting an animal from a parasitic invertebrate pest, wherein the compound is administered orally, and wherein the compound is administered in a dosage of from about 0.01 mg/kg to about 100 mg/kg of animal body weight. Flea control tests were performed on cats using 10 mg/kg with an unspecified “test compound” solubilized in PPG/glycerol, with a low effect of “at least 50% mortality”.

SUMMARY

In one aspect of the present invention a low dose of fluralaner or another isoxazoline derivative is administered to an animal such as a pet, typically a dog or a cat, preferentially by administration of a repeated dose, at regular intervals or at varying intervals, each dose being of the same or different amount, which leads to efficacy against arthropods, especially fleas and ticks.

The dose can be reduced at least 2, 3, 4, 5, 6, 7, 8, 9, 10 times, preferentially at least 3, 4, 5 times, even more preferentially about 4 times from a leading commercial product (BRAVECTO®) at the filing date of this specification. Efficacy against fleas is immediate and up to 60 days, and efficacy against ticks is from 5 days and up to 45 days.

Plasma concentration of at least 80, 90, 100, 110, 120, 130, 140, 150 ng/ml is reached in about 5-7 days, with at least 5, 10, 15, 20, 30, 40, 50 ng/ml reached from the first day of administration.

Plasma concentration can be at least about 2, 3, 4, 5, 6, 7, 8, 9, 10 times higher as would have been expected from the conventional protocol in the leading commercial product (25 mg/kg every 3 months).

Very useful and preferred embodiments of the present invention consist in the discovery of the interest and the surprising effects obtained in mixing every an each individual disclosures of the various concepts hereafter.

As an illustrative example, the invention consists in and discloses the Fluralaner low dose concepts associated with the Fluralaner new therapeutic indication and covers the combination:

- Fluralaner for use in protecting an animal from a parasitic invertebrate pest, wherein fluralaner is administered to said animal at a reduced dosage, said reduced dosage being comprised between 0.025 mg/kg and 12.5 mg/kg, between 0.035 mg/kg and 9.37 mg/kg, more preferably between 0.05 mg/kg and 9.37 mg/kg, for example, daily, and wherein said animal is for example a senior dog.
- A method for protecting an animal from a parasitic invertebrate pest comprising orally or parenterally administering to the animal a pesticidally effective amount of fluralaner, an N-oxide, a salt or an enantiomer thereof, wherein fluralaner is administered at a dosage comprised between 10 and 100 μg/kg/day, preferably at a dosage comprised between 20 and 50 μg/kg/day, even more preferably at a dosage comprised between 30 and 40 μg/kg/day, wherein the animal is for example a Serengeti cat.

Protecting an animal from a parasitic invertebrate pest includes preventing, reducing or eliminating parasitic infestation or infection of the animal.

Without being limited to a particular theory or effect, at least some embodiments rely on the higher biodisponibility of the isoxazoline derivative when administered at lower dose and/or at more frequent schedule and/or for a shorter or longer duration than in the state of the art.

Particular embodiments of the concepts included in the present invention can be single or combinations of the following embodiments:

1. Fluralaner or Other Isoxazoline Derivative in Low Dose Form:

Fluralaner administered at a lower dose than indicated by the commercial products for the target animal. Doses can be administered orally, such as pet food, for example in liquid or solid form, or a mixture of both, gel, for example to be deposited on or mixed with food, treats, pills, tablets, strips, chews, drinking water or other drinking liquid, oral or nasal spray. Doses can be administered topically, such as collar, tag, impregnated device such as an impregnated toy, patch, spot-on, pour-on, matrix, such as a matrix with controlled diffusion kinetics. Doses can be administered by injection or subparenterally by another method, such as implant, long- or delayed-action injectable. Combinations of these modes of administration are also envisioned, simultaneously, sequentially, or alternatively in a chronological sequence.

Fluralaner administered continuously or periodically, such as daily, weekly, monthly. Fluralaner administered in a charging dose and maintenance doses, for example, in combination with a continuous and/or periodical schedule.

Dose can be between about 35 and 250 μg/kg of the animal, for example daily, for example, for one to several months, such as three months. Efficacy against fleas can be obtained with a plasmatic concentration of at least about 10 ng/ml, efficacy against tick with at least about 100 ng/ml.

2. Fluralaner or Other Isoxazoline Derivative New Galenic Form:

Fluralaner administered in a form or vehicle promoting, assisting, or ensuring delivery of a lower dose than indicated by the commercial products for the target animal.

3. Fluralaner or Other Isoxazoline Derivative New Posology Indications:

Fluralaner administered in combination with pet food, during meals, or relative to meals to benefit from the synergistic effect of administration with food. The posology is determined so as to reduce the total amount present in the animal before, during, or after treatment, and/or to reduce the total amount present in the animal dejections, whether solid or liquid. The doses can be cumulated by several simultaneous or quasi-simultaneous administrations, or a charging dose followed by maintenance doses. The administration can be based on a schedule or on observation of symptoms of infestation. The dose of a day or scheduled period can be subdivided or continuous during the day or part of the day, for example, 2, 3, 4, 5 or more sub-doses, which can be administered at or around meals. The administration of the reduced dose can be for protection or treatment during only one day, two, three, four, or five days.

4. Fluralaner or Other Isoxazoline Derivative New Therapeutic Indications:

Fluralaner administered to protect or treat animals against tiger mosquitoes. Fluralaner administered to protect or treat particular races or species of animals or pets, particular animals or groups having digestive affections or difficulties, for example, by the use of the meal effect, animals having particular affections, particular gender (male or female), specific age group, such as pups or senior dogs and/or cats, particular size, such as large dogs and/or cats.

5. Fluralaner or Other Isoxazoline Derivative New Combination with Other Active or Synergistic Ingredient(s):

Fluralaner in combination with another active against endoparasite(s), ectoparasite(s), or combinations thereof. For example, in combination with an IGR (insect growth regulator), such as pyriproxyfene, permethrine, lufenuron, with a repellant, such as citridiol or a pyrethroid inseticice, such as flumethrin. Also, separately or additionally, fluralaner in combination with pheromones. Fluralaner administered with a repellent or active against mosquitoes, phlebotominae, red bugs, wasps, hornets, in particular with effect on the environment surrounding the pet.

6. Fluralaner Smart Devices and Methods:

A smart device or intelligent device is a device that releases a low dose of fluralaner in accordance with the invention, wherein the dose is controlled by an action on the device or remotely on a remote controller that interacts with the device. The remote controller can be a computer, a phone or a smartphone, for example. Interaction is via telephone lines, data channels, and/or magnetic or electromagnetic signals. The smart device or intelligent device can be a collar, or another device secured, administered or implanted on or in the animal, such as a patch, an implant, a matrix, etc., or any other device equipped with a remote control circuit and antenna adapted for remote control by a user. The release is preferentially topical, but the release can also be parenteral, intravenous, oral, buccal and/or nasal.

DETAILED DESCRIPTION

Definitions and Incorporations by Reference

In this specification, any description of an ingredient, composition, action, or method that mentions fluralaner also constitutes the description of the same ingredient, composition, action or method for any isoxazoline derivative, or combinations thereof, including the isoxazoline derivatives mentioned in the following section “active principle: isoxazoline derivatives”.

In this specification, any mention of a patent, patent application publication, patent application, or other publication or document constitutes an express incorporation by reference of the contents of that document, to the extent it is not inconsistent with this specification.

Thus, in the framework of the invention, the concepts/ideas and technical solutions provided are developed and exemplified with the fluralaner molecule. However, the results obtained for fluralaner can be applied to other isoxazoline derivatives, including variants.

Therefore, in this specification, all the described molecules, and other existing isoxazolines and variants are comprised within the scope of this invention and the term fluralaner can be exchanged with any other isoxazoline molecule described above that are in the scope of our invention.

In this specification, the description of each embodiments of compounds, compositions, formulations, associations, combinations, methods, and uses, constitutes a description of the association of several of such embodiments, and the association of any of such individual or combined embodiments, in particular, combinations with any or several in combination of the embodiments of methods and uses described herein.

Active Principle: Isoxazoline Derivatives

Fluralaner

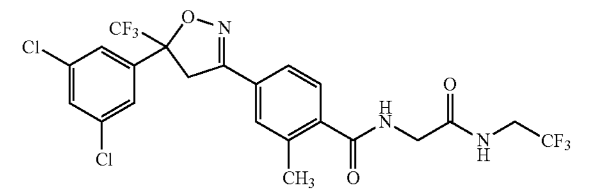 [SMILES: Cc1cc(C2=NOC(c3cc(Cl)cc(Cl)c3)(C(F)(F)F)C2)ccc1C(=O)NCC(=O)NCC(F)(F)F]

Fluralaner molecule: CAS 864731-61-3

As described in patent WO05085216

Other Isoxazoline Molecules

Fluralaner Derivatives

Other isoxazoline molecules can also be encompassed in the present invention, such as:

Fluralaner derivatives, as described in patent WO05085216 in series 5

Afoxolaner afoxolaner (CAS 1093861-60-9)

4-[(5RS)-5-(5-Chloro-α,α,α-trifluoro-m-tolyl)-4,5-dihydro-5-(trifluoromethyl)-1,2-oxazol-3-yl]-N-[2-oxo-2-(2,2,2-trifluoroethylamino)ethyl]naphthalene-1-carboxamide

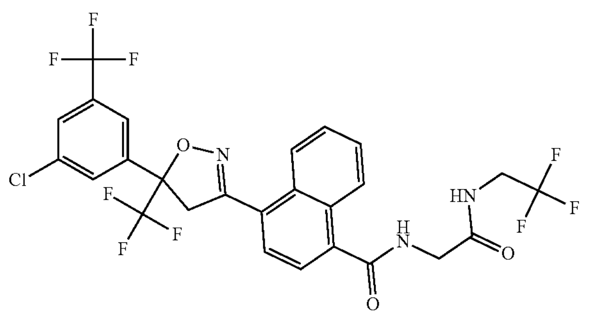 [SMILES: O=C(CNC(=O)c1ccc(C2=NOC(c3cc(Cl)cc(C(F)(F)F)c3)(C(F)(F)F)C2)c2ccccc12)NCC(F)(F)F]

Sarolaner sarolaner (CAS 1398609-39-6)

1-(5'-((5S)-5-(3,5-Dichloro-4-fluorophenyl)-5-(trifluoromethyl)-4,5-dihydroisoxazol-3-yl)-3'-H-spiro(azetidine-3,1'-(2)benzofuran)-1-yl)-2-(methylsulfonyl)ethanone

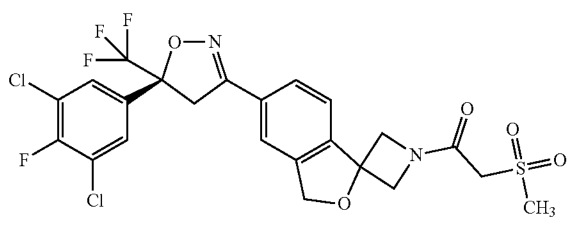 [SMILES: CS(=O)(=O)CC(=O)N1CC2(C1)OCc1cc(C3=NO[C@@](c4cc(Cl)c(F)c(Cl)c4)(C(F)(F)F)C3)ccc12]

Lotilaner lotilaner (CAS 1369852-71-0)

5-((5S)-4,5-dihydro-5-(3,4,5-trichlorophenyl)-5-(trifluoromethyl)-3-isoxazolyl)-3-methyl-N-(2-oxo-2-((2,2,2-trifluoroethyl)amino)ethyl)-2-thiophenecarboxamide

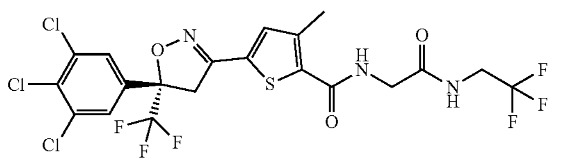 [SMILES: Cc1cc(C2=NO[C@@](c3cc(Cl)c(Cl)c(Cl)c3)(C(F)(F)F)C2)sc1C(=O)NCC(=O)NCC(F)(F)F]

Tigolaner tigolaner CAS 1621436-41-6

2,2-Chloro-N-(1-cyanocyclopropyl)-5-(1'-methyl-3'-(1,1,2,2,2-pentafluoroethyl)-4'-(trifluoromethyl)(1,5'-bi-1H-pyrazol)-4-yl)benzamide

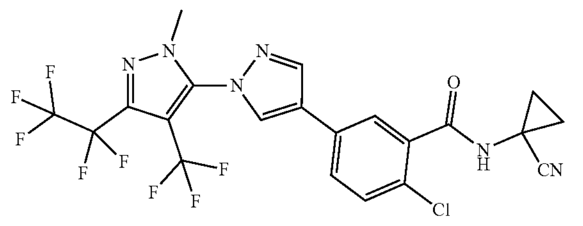 [SMILES: Cn1nc(C(F)(F)C(F)(F)F)c(C(F)(F)F)c1-n1cc(-c2ccc(Cl)c(C(=O)NC3(C#N)CC3)c2)cn1]

Other Isoxazoline Derivatives

CAS 943846-17-1, CAS 1231753-88-0, CAS1231754-09-8, CAS 1231755-02-4, CAS 1393119-41-9, CAS 1414378-14-5,

Compound 33-Z,

Compound 1-129 from WO2008122375

Compound II from WO2015150442

SCY-344,

Fluxametamide CAS 928783-29-3

CAS 1237587-26-6

SYN547407=isocycloseram (Syngenta), CAS 2061933-85-3

Sumitomo's candidate described in WO2012086462

Avista's candidate (WO2016115315)—A1443

Anacor (AN8391) and backup (AN11437) candidates (US2013131017, U.S. Pat. No. 8,546,357, WO13078071)

Isoxazolines as described in patents EP2833867 and EP2182945:

4-[5-(3,5-dichlorophenyl)-4,5-dihydro-5-(trifluoromethyl)-3-isoxazolyl)-2-methyl-N-(2-pyridinylmethyl)benzamide;

4-[5-(3,5-dichlorophenyl)-4,5-dihydro-5-(trifluoromethyl)-3-isoxazolyl)-2-methyl-N-[2-oxo-2-[(2,2,2-trifluoroethyl)amino]ethyl)benzamide;

4-[5-(3,5-dichlorophenyl)-4,5-dihydro-5-(trifluoromethyl)-3-isoxazolyl)-2-methyl-N-[2-(methylthio)ethyl)benzamide;

4-[5-(3,5-dichlorophenyl)-4,5-dihydro-5-(trifluoromethyl)-3-isoxazolyl)-2-methyl-N-[2-(methylsulfinyl)ethyl)benzamide;

4-[5-(3,5-dichlorophenyl)-4,5-dihydro-5-(trifluoromethyl)-3-isoxazolyl)-2-methyl-N-[2-(methylsulfonyl)ethyl)benzamide;

4-[5-(3,5-dichlorophenyl)-4,5-dihydro-5-(trifluoromethyl)-3-isoxazolyl)-2-methyl]-N-[1-methyl-3-(methylthio)propyl]benzamide;

4-[5-(3,5-dichlorophenyl)-4,5-dihydro-5-(trifluoromethyl)-3-isoxazolyl)-2-methyl-N-(2-pyridinylmethyl)benzamide;

4-[5-(3,5-dichlorophenyl)-4,5-dihydro-5-(trifluoromethyl)-3-isoxazolyl)-2-methyl-N-[2-oxo-2-[(2,2,2-trifluoroethyl)amino)ethyl)benzamide;

4-[5-(3,5-dichlorophenyl)-4,5-dihydro-5-(trifluoromethyl)-3-isoxazolyl)-2-methyl-N-[2-(methylthio)ethyl)benzamide;

4-[5-(3,5-dichlorophenyl)-4,5-dihydro-5-(trifluoromethyl)-3-isoxazolyl]-2-methyl-N-[2-(methylsulfinyl)ethyl]benzamide;

4-[5-(3,5-dichlorophenyl)-4,5-dihydro-5-(trifluoromethyl)-3-isoxazolyl]-2-methyl-N-[2-(methylsulfonyl)ethyl]benzamide;

and

4-[5-(3,5-dichlorophenyl)-4,5-dihydro-5-(trifluoromethyl)-3-isoxazolyl]-2-methyl-N-[1-methyl-3-(methylthio)propyl]benzamide.

Compound of formula (I)

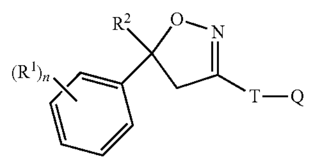

Formula (I), wherein $R^1$=halogen, $CF_3$, $OCF_3$, CN, n=integer from 0 to 3, preferably 1, 2 or 3, $R^2$=$C_1$-$C_3$-haloalkyl, preferably $CF_3$ or $CF_2Cl$, T=5- or 6-membered ring, which is optionally substituted by one or more radicals Y, Y=methyl, halomethyl, halogen, CN, $NO_2$, $NH_2$—C═S, or two adjacent radicals Y form together a chain, especially a three or four membered chain;

Q=X—$NR^3R^4$ or a 5-membered N-heteroaryl ring, which is optionally substituted by one or more radicals:

X=$CH_2$, $CH(CH_3)$, CH(CN), CO, CS, $R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuiryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl, $R^3$-1

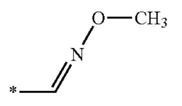

$R^3$-2

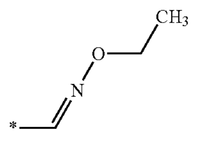

$R^3$-3

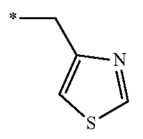

$R^3$-4

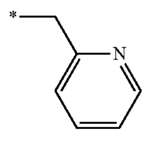

$R^3$-5

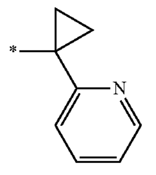

$R^3$-6

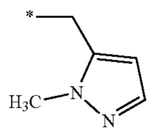

$R^3$-7

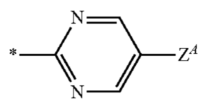

$R^3$-8

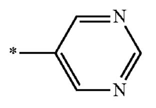

-continued $R^3$-9

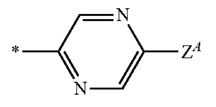

$R^3$-10

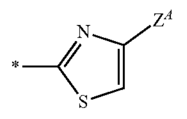

$R^3$-11

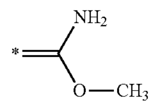

$R^3$-12

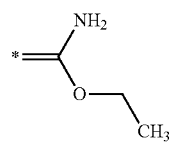

$R^3$-13

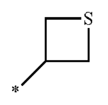

$R^3$-14

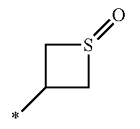

$R^3$-15

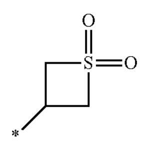

wherein zA=hydrogen, halogen, cyano, halomethyl ($CF_3$);

$R^4$=hydrogen, ethyl, methoxymelhyl, halomelhoxymelhyl, ethoxymethyl, haloethoxymethyl, propoxymethyl, methylcarbonyl, elhylcarbonyl, propylcarbonyl, cyclopropylcarbonyl, methoxycarbonyl, melhOxymethylcarbonyl, amine>carbonyl, elhylaminocarbonylmethyl, elhylaminocarbonylethyl, dimelhOxyethyl, propynylaminocarbonylmethyl, haloethylaminocarbonylmelhyl, cyanomelhylaminocarbonylmelhyl, or haloethylaminocarbonylethyl;

or R3 and R4 together form a substituent selected from the group consisting of:

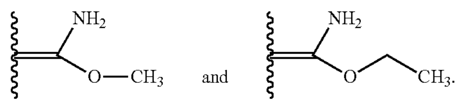

Compounds of formula i

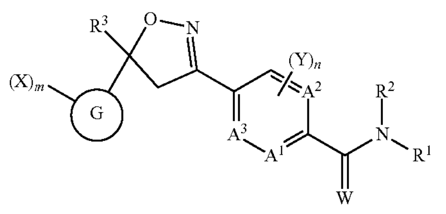

i wherein, inter alia, each of $A^1$, $A^2$ and $A^3$ are independently C or N; G is a benzene ring; W is O or S; and X is halogen or CrC6 haloalkyl.

Isoxazoline Variants

Such molecules are disclosed as well as their corresponding N-oxides, enantiomers, salts, solvates, polymorphs . . . especially S-fluralaner, which the most active enantiomer of fluralaner, having a CAS nb: CAS 1122022-02-9.

Concepts

1 Fluralaner Low Dose

The description of the concepts in this section "Fluralaner low dose" constitutes a description of each of these concepts in combination with each of the concepts disclosed in the other five sections, and/or other portions of this description.

In particular, each "low dose" concept can be combined with a "new galenic" concept, and/or a "new posology" concept, and/or a new therapeutic indication" concept, and/or a "new combinations" concept. Each "low dose" concept is particularly appropriate to be implemented in association with a "new posology" concept, and such association is particularly appropriate to be implemented with a "new galenic" concept, and in a "new therapeutic indication" (each of these indications being with or without the "new galenic" concept and/or with or without a "new combination" concept).

1.1 Important Features

From the known dosage of 25 mg/kg bodyweight/3 months of sustained efficacy (Bravecto), a 1-month dosage is supposed to be 25/3=around 8 mg/kg/month. However, in one aspect of the invention, a dosage as low as 1 or 2 or 3 or 4 mg/kg/month is sufficient to obtain the desired effect. This represents a decrease in dosage of 2 or even more than 2 times. This is particularly interesting as fluralaner is not degraded in stools and can pollute the environment. Moreover, adverse effects with fluralaner have been reported and a decrease in dosage enables to limit those undesirable effects. Therefore applying the exact needed dosage to an animal is extremely beneficial, also because of the cost of the active ingredient and the economic advantage produced by an adjustment of the really effective dose.

Target dosage in one embodiment: about 35 μg/kg/day×90 days: which means 8 times less product than the currently marketed fluralaner product (Bravecto).

The target dosage (expressed in μg of active ingredient/kg of animal bodyweight/day of administration of the active ingredient to the animal) may vary according to the targeted pest and its susceptibility to the active ingredient. Therefore, the target dosage may vary, for example, between about 5 μg/kg/day to about 200 μg/kg/day. In another embodiment, the target dosage may vary between about 10 μg/kg/day to about 100 μg/kg/day or between about 20 μg/kg/day to about 50 μg/kg/day.

Fluralaner may be administered as a single dose for a predetermined period of efficacy and/or as a regular and/or continuous sustained release for a determined period of time in order to maintain the effective amount of the active ingredient in the body.

Dosage forms may contain from about 0.5 mg to about 5 g of an active agent. In one embodiment of the dosage form, the dosage is from about 1 mg to about 500 mg of the active agent. More typically the dosage is about 1 mg to about 25 mg, 1 mg to about 50 mg, 10 mg to 10 about 100 mg, or 20 mg to about 200 mg. In other embodiments, the dosage is about 50 mg to about 300 mg, 50 mg to about 400 mg, 50 mg to about 500 mg, 50 mg to about 600 mg, 50 mg to about 800 mg, or 100 mg to about 1000 mg. In one embodiment of the invention, the active agent is present in the formulation at a concentration of about 0.05% to about 50% weight/volume. In other embodiments, the active agent may be present in the formulation at a concentration of about 0.1% to about 30%, about 0.5% to about 20% (w/v) or about 1% to about 10% (w/v). In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume. In a particular advantageous embodiment of the invention, the daily dose of the compounds is about 0.01 mg/kg to about 0.10 mg/kg of weight of animal. In another embodiment, the dose is about 0.02 mg/kg to about 0.08 mg/kg of weight of animal. In other embodiments, the dose of the inventive compounds is about 0.02 mg/kg to about 0.05 mg/kg, about 0.025 mg/kg to about 0.050 mg/kg or about 0.03 mg/kg to about 0.04 mg/kg. In other preferred embodiments, the dose is about 0.031 mg/kg to about 0.039 mg/kg, 0.032 mg/kg to about 0.038 mg/kg or 0.033 mg/kg to about 0.037 mg/kg. More typically, in some embodiments the dose of the active compounds is about 0.034 mg/kg to about 0.036 mg/kg. In still other embodiments of the invention, the dose received daily by the animal may be as low as about 0.035 mg/kg. With a device adapted for releasing such a dose daily, the total amount of active received after 3 months does not exceed 3.15 mg/kg (which is highly desirable compared to the current amount dispensed by Bravecto for the same period of time that is 25 mg/kg).

1.2 Definitions

Reduced dosage: in the framework of the invention, «reduced dosage» refers to a dosage that is decreased regarding usual recommendation (ie 25 mg/kg/3 months for a dog in Bravecto®). In some embodiments, this reduced dosage corresponds to 1/50, 1/10, 1/8, 1/7, 1/5, 1/4, 1/3, 3/8, 1/2 times the regular dosage of the Bravecto for a given period of time.

For instance, with Bravecto, a 25 mg/kg dosage is recommended for a dog over a period of 3 months. A reduced dosage thus corresponds for example to less than 12.5, 9.37, 8.33, 5, 3.5, 3.15, 3, 2.5, 0.5 mg/kg for a period of 3 months, in a single or as multiple administrations.

For a dog receiving fluralaner, this reduced dosage is comprised for example between around 0.5 and around 12.5 mg/kg, preferably between around 2.5 and around 10 mg/kg preferably between around 5 and around 10 mg/kg, preferably between around 7 and around 10 mg/kg.

Around: in the framework of the invention, around refers to a value that is more or less 1%, 2%, 3%, 4%, 5%, 10%, 15%, 20%, 25%, 30% of the target value. For instance, a dosage of around 5 mg/kg refers to a dosage of 5 mg, but also to a dosage comprised between 4.75 and 5.25 mg/kg to dosage comprised between 3.5 to 6.5 mg/kg.

About: in the framework of the invention, about also refers to a value that is more or less 1%, 2%, 3%, 4%, 5%, 10%, 15%, 20%, 25%, 30% of the target value. For instance, a dosage of about 5 mg/kg refers to a dosage of 5 mg, but also to a dosage comprised between 4.75 and 5.25 mg/kg to dosage comprised between 3.5 to 6.5 mg/kg.

In an embodiment, the dosage of 12.5 mg/kg for administration of fluralaner to a dog is specifically excluded.

By "effective amount" or "efficient amount" or "effective dose" is intended a sufficient amount of a composition of the invention to eradicate or reduce the number of parasites infesting the animal. In one embodiment, an effective amount of the active agent achieves at least 70% efficacy against the target parasite compared to a negative control according to known methods used in the art (animal not treated or treated with a placebo). In other embodiments, an effective amount of the active agent achieves at least 80%, or at least 90% efficacy against the target pests. Preferably, an effective amount of the active agent will achieve at least 95% efficacy against the target pests. In some embodiments, an effective amount of the compounds and compositions of the invention achieve at least 98% or 100% efficacy against the target parasites.

In the framework of the invention, a "nanodosage" means an extremely reduced dosage as compared to the well-established treatment. A nanodosage refers to a dosage that is less than 700 times less than the well-established treatment. For instance, a dosage of 0.035 mg/kg, whereas the well-established treatment is 25 mg/kg.

In the framework of the invention "week-end therapy" means administering to an animal, for example an animal leaving indoor, a preventive compound to avoid infestation by indesirable parasites such as some or all of fleas, ticks, mites or the like, particularly fleas, ticks, or both. A week-end therapy is administered prior to contacting the animal with a dangerous environment and has an immediate or rapid action.

In at least some embodiments of the invention, an "efficient protection" is attained when the plasmatic concentration of fluralaner in the bloodstream is superior to around 10 ng/ml against fleas, superior to around 100 ng/ml against ticks.

1.3 Embodiments

Fluralaner can be administered at a reduced dosage using various routes: topical, oral, injectable.

For topical route, fluralaner can be administered for example through a collar, a smart collar, a tag, an impregnated device, a spot-on, a pour-on or a patch.

For oral route, fluralaner can be administered as a pet food (solid or liquid), treats, pastes, chews, tablets, in addition to drinking water or as a liquid to be poured directly in the mouth or on the food.

For injectable route, fluralaner can be administered as an implant, a biodegradable injectable implant ("depot implant"), an injection (s.c. or i.m.), a long acting injectable.

In an embodiment, the dose for the prevention and/or the treatment of a flea infestation of the animal is administered to an animal one, two, three, four, five days in a row, in a nanodosage.

In an embodiment, the dose is administered to an animal one, two, three, four, five days in a row, preferably 4 days, in a mean daily dosage of about 0.01 to 0.05 mg/kg, preferably about 0.02 to 0.04 mg/kg, even more preferably around 0.035 mg/kg.

In an embodiment, the dose is administered to an animal one, two, three, four, five days in a row, in a dosage of about 0.035 mg/kg.

In an embodiment, said dose is administered orally.

In an embodiment, said animal is a dog.

In another embodiment, the dose for the prevention and/or the treatment of a tick infestation of the animal is administered to an animal one, two, three, four times in a row, at a dosage comprised between 0.1 and 0.5 mg/kg, preferably 0.2 and 0.3 mg/kg, preferably 0.25 mg/kg, followed by a nanodosage for 1, 2, 3, 4, 5, 6, 7, 8, 9 days. Optionally, the animal is further administered a 0.6 mg/kg dosage one time.

In another embodiment, the dose is administered to an animal one, two, three, four times in a row, at a dosage 0.1 and 0.5 mg/kg, preferably 0.2 and 0.3 mg/kg, preferably 0.25 mg/kg, followed by a dosage of about 0.035 mg/mg for 1, 2, 3, 4, 5, 6, 7, 8, 9 days, preferably 6 days. Optionally, the animal is further administered a 0.6 mg/kg dosage one time.

In another embodiment, the dose is administered to an animal one, two, three, four times in a row, at a dosage of 0.25 mg/kg, followed by a nanodosage for 1, 2, 3, 4, 5, 6, 7, 8, 9 days. Optionally, the animal is further administered a 0.6 mg/kg dosage one time.

In another embodiment, the dose is administered to an animal one, two, three, four times in a row, at a dosage of 0.25 mg/kg, followed by a low dosage of about 0.035 mg/mg for 1, 2, 3, 4, 5, 6, 7, 8, 9 days. Optionally, the animal is further administered a 0.6 mg/kg dosage one time.

In an embodiment, said dose is administered orally.

In an embodiment, said animal is a dog.

In another embodiment, the dose is administered once to an animal in a reduced dosage of 6.25 mg/kg, In an embodiment, said dose is administered topically.

In an embodiment, said animal is a dog.

In an embodiment, fluralaner is administered to an animal as a monthly treatment at a reduced dosage with an efficacy of at least 1 month. Said reduced dosage corresponds to about ¼, ⅕, ⅙, ⅐, ⅛, ⅑, ⅒ of the standard dosage of 25 mg/kg. Preferably said reduced dosage is comprised between 2 and 3 mg/kg.

In an embodiment, the animal is a dog.

Fluralaner Week End Therapy:

Fluralaner for use in protecting an animal from a parasitic invertebrate pest (ticks, flea or mite), wherein the compound is administered orally, wherein the compound is administered 1, 2, 3, 4, 5, 6, 7, 8, 9 hours, preferably 3 to 5 hours, preferably 4 hours prior to a walk in a dangerous environment.

A method for protecting an animal from a parasitic invertebrate pest comprising orally or parenterally administering to the animal a pesticidally effective amount of fluralaner, an N-oxide, a salt or an enantiomer thereof, wherein the compound is administered orally, wherein the compound is administered 1, 2, 3, 4, 5, 6, 7, 8, 9 hours, preferably 3 to 5 hours, for example, 4 h, prior to a walk in a dangerous environment.

In an embodiment, the animal is a dog.

Fluralaner Pet Food:

Fluralaner for use in protecting an animal from a parasitic invertebrate pest (ticks, flea or mite), wherein the compound is administered orally, wherein the compound is administered in the pet food, every day, every 2, 3, 4, 5, 6, 7 days at a nanodosage.

Fluralaner for use in protecting an animal from a parasitic invertebrate pest (ticks, flea or mite), wherein the compound is administered orally, wherein the compound is administered in the pet food, every day, every 2, 3, 4, 5, 6, 7 days in a dosage of about 0.01 to 0.05 mg/kg, preferably about 0.02 to 0.04 mg/kg, even more preferably around 0.035 mg/kg Petfood comprising fluralaner for use in protecting an animal from a parasitic invertebrate pest (ticks, flea or mite), wherein fluralaner is administered at a nanodosage.

Petfood comprising fluralaner for use in protecting an animal from a parasitic invertebrate pest (ticks, flea or mite), wherein fluralaner is administered in a dosage of about 0.01 to 0.05 mg/kg, preferably about 0.02 to 0.04 mg/kg, even more preferably around 0.035 mg/kg In an embodiment, the animal is a dog. Preferably the animal is a cat.

In an embodiment, Fluralaner is in a galenic form suitable to be administered or mixed within the pet food (powder, liquid, paste or the like) or as a petfood kibble.

Fluralaner on Demand:

Fluralaner for use in protecting an animal from a parasitic invertebrate pest (ticks, flea or mite), wherein the compound is administered on demand, when the animal is considered at risk (for example when the animal is about to be in a dangerous environment). Fluralaner is preferably administered at a nanodosage, and the dose is repeated when necessary to ensure an efficient protection.

Aspects of the present invention relates also to methods, apparatuses and compositions which allow the sequential application of Fluralaner for ensuring better treatment. The invention is applicable to any veterinary agent in addition to Fluralaner, in particular with a therapeutic or cosmetic or dermatological effect, and to any animal.

There remains today, in the animal health field, a need for novel strategies for administering veterinary compounds which make it possible to improve the treatments while at the same time maintaining maximum safety for the user and for the environment.

The inventors have developed a novel approach for treating animals with Fluralaner, which consists in sequentially applying a veterinary composition. The inventors have shown that this sequential application has advantages, in particular for treatments of parasites, compared with oral or spot-on or pour-on application, such as the prevention of side effects and efficacy.

The inventors have developed a novel method for treating animals which consists in administering a veterinary composition containing Fluralaner sequentially according to a determined application mode. The inventors have shown that this method allows better control of the doses and greater efficacy of action, without side effects for the animals. In particular, the inventors have shown that the sequential administration with an initial dose (termed loading dose) of veterinary compounds can make it possible to obtain, at equal total doses, an effect greater than that obtained in particular by oral or spot-on or pour-on application.

A subject of the present invention therefore lies in a process for applying a veterinary compound to a non-human mammal, comprising the sequential topical, oral, transdermal, etc. . . . application of a determined total dose of Fluralaner according to a dosage regimen comprising (i) an initial dose D0, applied at the beginning of treatment, representing at most 65% of the determined total dose, and (ii) a plurality of maintenance doses Di, applied sequentially during the duration of the treatment. The sum of the Di doses and of the DO dose is equal to the determined total dose and the total dose is a reduced dosage.

Another subject of the present invention lies in a process for therapeutic or cosmetic treatment of a non-human mammal by administration of Fluralaner, the process comprising the sequential application, in particular the sequential topical application, of a determined total dose of said compound according to a dosage regimen of Fluralaner comprising (i) an initial dose D0, applied at the beginning of treatment, representing at most 65% of the determined total dose, and (ii) a plurality of maintenance doses Di, applied sequentially during the duration of the treatment. The sum of the Di doses and of the DO dose is equal to the determined total dose. The total dose is a reduced dosage.

Another subject of the invention relates to Fluralaner for use thereof for the therapeutic or cosmetic treatment of a non-human mammal by sequential application of a determined total dose of Fluralaner, characterized in that the application is carried out according to a dosage regimen comprising (i) an initial dose D0, applied at the beginning of treatment, representing at most 65% of the determined total dose, and (ii) a plurality of maintenance doses Di, applied sequentially during the duration of the treatment. The sum of the Di doses and of the D0 dose is equal to the determined total dose. The total dose is a reduced dosage.

Another subject of the invention relates to the use of Fluralaner for producing a composition intended for the therapeutic or cosmetic treatment of a non-human mammal by sequential topical application of a determined total dose of said compound, characterized in that the application is carried out according to a dosage regimen comprising (i) an initial dose D0, applied at the beginning of treatment, representing at most 65% of the determined total dose, and (ii) a plurality of maintenance doses Di, applied sequentially during the duration of the treatment. The sum of the Di doses and of the DO dose is equal to the determined total dose. The total dose is a reduced dosage.

The Fluralaner (or a composition comprising Fluralaner) can be applied to the mouth or to the blood or to the skin or to the hair of the non-human mammal manually (pipette, spray) or in an automated manner.

Another subject of the invention relates to a device for delivering Fluralaner to a non-human mammal, characterized in that it comprises a determined total dose of said compound and a controlled sequential release system ensuring the delivery of an initial dose D0 of the compound at the beginning of treatment, said dose D0 representing 0.5% to 65% of the determined total dose, and of a plurality of maintenance doses Di of the compound, the sum of the Di doses and of the D0 dose being equal to the determined total dose. The device may be for example a pipette, a collar, an implant, or a biodegradable bolus or cap or pill or tablet, in particular a collar comprising a dispersing nozzle, etc.

The invention is applicable to any veterinary compound with Fluralaner and it can be implemented in any non-human mammal, such as in particular pets (canines, felines, etc.), farm animals (cattle, the ovine race, pigs, etc.), horses, etc. The dose(s) DO and maintenance dose(s) Di may take the values as indicated for charge and maintenance doses in other parts of this description.

A subject of the invention therefore relates to a compound (or a composition) for use thereof for treating a non-human mammal by sequential application of a determined total dose of said compound, characterized in that the application is carried out according to a dosage regimen comprising (i) an initial dose D0, applied at the beginning of treatment, representing at most 65% of the determined total dose, and (ii) a plurality of maintenance doses Di, applied sequentially during the duration of the treatment, the sum of the Di doses and of the DO dose being equal to the determined total dose.

As indicated, an aspect of the invention is based in particular on the unexpected demonstration that the distribution of the effective total amount of Fluralaner for veterinary use in several sequential doses (or fractions), including an initial dose (loading dose D0) and maintenance doses (Di or di), makes it possible to obtain a better effect than the application of the determined total dose (D) and that the total dose is a reduced dosage.

The initial dose (DO) may be adapted by those skilled in the art according to the target non-human mammal and to the duration of the treatment.

In one preferred embodiment, the initial dose D0 represents from 0.5% to 60% of the determined total dose, preferably from 1% to 60%. More preferentially, when the targeted treatment duration is less than 2 months, the initial dose D0 advantageously represents from 10-60% of the determined total dose, in particular from 15-60%, from 20-60%, from 20 to 50% or from 30 to 50%. When the targeted treatment duration is greater than 2 months, the initial dose D0 preferably represents from 0.5% to 10%, from 0.5% to 8%, more preferentially from 1% to 5%, of the determined total dose.

In one particular mode, when Fluralaner has a targeted treatment duration of less than 2 months, the initial dose D0 advantageously represents from 10-60% of the determined total dose, preferably from 15-60%, more preferentially from 20% to 60%, from 20% to 50% or even more preferentially from 30-50%.

In one particular mode, when Fluralaner has a targeted treatment duration of greater than 2 months, the initial dose D0 advantageously represents from 0.5% to 10% of the determined total dose, from 0.5% to 8%, or more preferentially from 1-5%.

After application or release of the initial dose, the treatment of the invention comprises the application or the release of several maintenance doses (Di). In the context of the invention, the maintenance doses may be identical or variable during treatment. Preferably nevertheless, all the maintenance doses Di are identical.

Preferably, each maintenance dose Di represents at most 35% of the initial dose D0, more preferentially at most 20%, even more preferentially at most 10%. Moreover, the frequency of application of the maintenance doses Di may be constant throughout the treatment, or variable.

In one preferred mode, the maintenance doses Di are identical and their frequency of application is constant during the treatment. Advantageously, the frequency of application of the maintenance doses Di is between 1 h and 1 month, preferably between 2 h and 15 days, more preferentially between 4 h and 7 days, even more preferentially between 12 h and 4 days.

The duration of the treatment, or the frequency of application and/or the amount of the maintenance doses Di can be adjusted by those skilled in the art according to Fluralaner, to the non-human mammal and to the type of treatment. Thus, the duration of the treatment can be between 1 and 24 months, more preferentially between 1 and 18 months, for example between 6 and 12 months or 1 and 6 months.

In one particular mode, the compound is Fluralaner or a mixture of therapeutic agents (e.g. of antiparasitics), the initial dose D0 represents from 20-60% of the determined total dose, and each maintenance dose Di is identical and administered daily.

Topical Administration:

The invention comprises the sequential topical administration of Fluralaner or more compounds, according to a determined application mode. The administration is topical and preferentially localized on the skin, at the surface.

In one preferred mode of the invention, Fluralaner or the composition is administered on a zone of the animal's skin, for example the neck or any practical zone (for example the back, between the shoulders, etc.) by means of a device suitable for the targeted zone, such as, for example, a collar, a spray or a dispersing nozzle. The administration can be carried out by means of any device comprising a container containing the compound.

In one preferred mode, Fluralaner or the composition is administered by means of a controlled-release device, for example a collar. Other controlled-release-mode devices are mentioned for example in patents U.S. Pat. No. 7,140,325 or U.S. Pat. No. 6,010,492 that are incorporated herewith by reference.

The administration of Fluralaner or the composition is generally continued until the whole of the determined total dose is administered. Of course, the treatment can be interrupted if the purpose is achieved beforehand or if the practitioner decides to do so. And this is one of the main advantage of the invention since it allows not to treat the animal if it is not necessary (in case there is no infestation, for example when the animal is in house).

Composition:

The term "composition" is intended to mean any formulation used for applying Fluralaner, whether it is pure or in mixture form, additionally comprising a carrier or excipient that is acceptable from a veterinary point of view.

The term "excipient that is acceptable from a veterinary point of view" is intended to mean an excipient that is tolerated by the non-human mammal when it is applied topically, and which is capable of sufficiently dissolving and/or formulating Fluralaner.

The composition of the present invention may also comprise one or more additional agents or adjuvants, such as one or more co-solvents, dyes, spreading agents, antioxidants, light-stabilizers and/or adhesion agents.

2 Fluralaner New Galenic

The description of the concepts in this section "Fluralaner new galenic" constitutes a description of each of these concepts in combination with each of the concepts disclosed in the other five sections, and/or other portions of this description, and in particular in combination with the concepts "Fluralaner low dose" disclosed in section 1 hereabove.

2.1 Important Features

Another aspect of the invention to be combined with the other features is the formation of parasiticidal compositions which comprise fluralaner. The composition of the invention can also be in a variety of forms which include, but are not limited to, oral formulations, injectable formulations, and topical, dermal or subdermal formulations. The formulations are intended to be administered to an animal which includes but is not limited to mammals, birds and fish.

Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

The composition of the invention may be in a form suitable for oral use, for example, as baits, dietary supplements, troches, lozenges, chewables, tablets, hard or soft capsules, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release. Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, polyethylene glycols (PEGs) and ethanol, or an oil medium, for example peanut oil, liquid paraffin, or olive oil. The compositions of the invention may also be in the form of oil-in-water or water-in-oil emulsions. The oily phase may be a vegetable oil, for example, olive oil or arachis oil, or a mineral oil, for example, liquid paraffin or mixtures of these. Suitable emulsifying agents may for example, soybean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening agents, bittering agents and/or preservatives. In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a co-surfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example C8-C10 caprylic/capric triglyceride. In another embodiment of the oily phase will represent a % v/v range selected from the group consisting of about 2 to about 15%; about 7 to about 10%; and about 8 to about 9% v/v of the microemulsion. The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion. Surfactants for the microemulsion include diethylene glycol monoethyl ether, dipropylene glycol monomethyl ether, polyglycolyzed C8-C10 glycerides or polyglyceryl-6 dioleate. In addition to these surfactants, the co-surfactants include short-chain alcohols, such as ethanol and propanol. Some compounds are common to the three components discussed above, i.e., aqueous phase, surfactant and co-surractant. However, it is well within the skill level of the practitioner to use different compounds for each component of the same formulation. In one embodiment for the amount of surractant/co-surfactant, the co-surfactant to surfactant ratio will be from about 1/7 to about 1/2. In another embodiment for the amount of co-surfactant, there will be from about 25 to about 75% v/v of surfactant and from about 10 to about 55% v/v of co-surfactant in the microemulsion. Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives. Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present. Syrups and elixirs may be formulated with sweetening agents, for example, glycerol, propylene glycol, sorbitol or sucrose. Such formulations may also contain a demulcent, a preservative, flavoring agent(s) and/or coloring agent(s). In another embodiment of the invention, the composition can be in paste form. Examples of embodiments in a paste form include but are not limited to those described in U.S. Pat. Nos. 6,787,342 and 7,001,889. In addition to the isoxazoline compound of the invention, the paste can also contain fumed silica; a viscosity modifier; a carrier; optionally, an absorbent; and optionally, a colorant, stabilizer, surfactant, or preservative.

The process for preparing a paste formulation comprises the steps of:

(a) dissolving or dispersing the isoxazoline compound into the mixer by mixing;

(b) adding the fumed silica to the carrier containing the dissolved isoxazoline compound and mixing until the silica is dispersed in the carrier;

(c) allowing the intermediate formed in (b) to settle for a time sufficient in order to allow the air entrapped during step (b) to escape; and (d) adding the viscosity modifier to the intermediate with mixing to produce a uniform paste.

The above steps are illustrative, but not limiting. For example, step (a) can be the last step.

In one embodiment of the formulation, the formulation is a paste containing isoxazoline compound, fumed silica, a viscosity modifier, an absorbent, a colorant; and a hydrophilic carrier which is triacetin, a monoglyceride, a diglyceride, or a triglyceride. The paste may also include, but is not limited to, a viscosity modifier including PEG 200, PEG 300, PEG 400, PEG 600, monoethanolamine, triethanolamine, glycerol, propylene glycol, polyoxyethylene (20) sorbitan mono-oleate (POLYSORBATE 80 or TWEEN 80), and poloxamers (e.g., PLURONIC L 81); an absorbent including magnesium carbonate, calcium carbonate, starch, and cellulose and its derivatives; and a colorant. The compositions may be in the form of a sterile injectable aqueous or oleaginous suspension or an injectable solution. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Co-solvents such as ethanol, propylene glycol glycerol formal or polyethylene glycols may also be used. Preservatives, such as phenol or benzyl alcohol, may be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables, topical, dermal and subdermal formulations can include emulsions, creams, ointments, gels, pastes, powders, shampoos, pour-on formulations, spot-on solutions and suspensions, dips and sprays. Topical application of an inventive compound or of a composition including at least one inventive compound among active agent(s) therein, in the form of a spot-on or pour-on composition, can allow for the inventive compound to be absorbed through the skin to achieve systemic levels, distributed through the sebaceous glands or on the surface of the skin achieving levels throughout the hair coat. When the compound is distributed through the sebaceous glands, they can act as a reservoir, whereby there can be a long-lasting effect (up to several months) effect. Spot-on formulations are typically applied in a localized region which refers to a relatively small area on the animal rather than to a large portion of the surface of the animal. In one embodiment of a localized region, the location is between the shoulders. In another embodiment of a localized region it is a stripe, e.g. a stripe from head to tail of the animal. Pour-on formulations are described in U.S. Pat. No. 6,010,710.

In some embodiments, the pour-on formulations may be oily, and generally comprise a diluent or vehicle and also a solvent (e.g. an organic solvent) for the active ingredient if the latter is not soluble in the diluent. In other embodiments, the pour-on formulations may be non oily, including alcohol-based formulations. Organic solvents that can be used in the invention include but are not limited to acetyltributyl citrate, fatty acid esters such as the dimethyl ester, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, propylene glycol monomethyl ether, propylene glycol monoethyl ether, ethylene glycol, diisobutyl adipate, diisopropyl adipate (also known as CERAPHYL 230), triacetin, butyl acetate, octyl acetate, propylene carbonate, butylene carbonate, dimethylsulfoxide, organic amides including dimethylformamide and dimethylacetamide, and diethyl phthalate, or a mixture of at least two of these solvents In one embodiment of the invention, the pharmaceutically or veterinarily acceptable carrier of the formulation comprises C1-C10 alcohols or esters thereof (including acetates, such as ethyl acetate, butyl acetate and the like), C10-C18 saturated fatty acids or esters thereof, C10-C18 monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycol s, glycol ethers, glycol esters or glycol carbonates, polyethylene glycols of various grades (PEGs) or monoethers, diethers, monoesters or diesters thereof (e.g. diethylene glycol monoethyl ether), or mixtures thereof. As vehicle or diluent, mention may be made of plant oils such as, but not limited to soybean oil, groundnut oil, castor oil, corn oil, cotton oil, olive oil, grape seed oil, sunflower oil, coconut oils etc.; mineral oils such as, but not limited to, petrolatum, paraffin, silicone, etc.; aliphatic or cyclic hydrocarbons or alternatively, for example, medium-chain (such as C8 to C12) triglycerides. In another embodiment of the invention, an emollient and/or spreading and/or film forming agent can be added. In one embodiment, the emollient and/or spreading and/or film-forming agent is those agents selected from the group consisting of: (a) polyvinylpyrrolidone, polyvinyl alcohols, copolymers of vinyl acetate and vinylpyrrolidone, polyethylene glycols, benzyl alcohol, 2-pyrrolidones including, but not limited to N-methylpyrrolidone, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulfates (e.g. sodium lauryl sulfate and sodium cetyl sulfate); sodium dodecylbenzenesulfonate, sodium dioctylsulphosuccinate; fatty acids (e.g. those derived from coconut oil), (c) cationic surfactants such as water-soluble quaternary ammonium salts of formula N+R'R"R'"R"", Y— in which the radicals R are optionally hydroxylated hydrocarbon radicals and Y— is an anion of a strong acid such as the halide, sulfate and sulfonate anions; cetyltrimethylammonium bromide is among the cationic surfactants which can be used, (d) amine salts of formula N+HR'R"R'" in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. POLYSORBATE 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents. The solvent will be used in proportion with the concentration of the isoxazoline compound and its solubility in this solvent. It will be sought to have the lowest possible volume. The vehicle makes up the difference to 100%.

In one embodiment of the amount of emollient, the emollient is used in a proportion of from 0.1 to 50% and 0.25 to 5%, by volume. In another embodiment of the invention, the composition can be in ready-to-use solution for localized topical application, including a spot-on formulation, as is described in U.S. Pat. No. 6,395,765. In addition to the isoxazoline compound, the solution may contain a crystallization inhibitor, an organic solvent and an organic co-solvent. In one embodiment of the amount of crystallization inhibitor, the crystallization inhibitor can be present in a proportion of about 1 to about 30% (w/v) in the composition. In other embodiments, the crystallization inhibitor may be present in a proportion of about 1 to about 20% (w/v) and about 5 to about 15%. Acceptable inhibitors are those whose addition to the formulation inhibits the formation of crystals when the formulation is applied. In some embodiments, formulations may include compounds that function as cristallization inhibitors other than those listed herein. In these embodiments, the suitability of a cristallization inhibitor may be determined by a the test in which 0.3 ml of a solution comprising 10% (w/v) of isoxazoline compound in the liquid carrier and 10% of the inhibitor are deposited on a glass slide at 200° C. and allowed to stand for 24 hours. The slide is then observed with the naked eye. Acceptable inhibitors are those whose addition provides for few (e.g. less than ten crystals) or no crystals. In one embodiment, the organic solvent has a dielectric constant of about 2 to about 35, 10 about 10 to about 35 or about 20 to about 30. In other embodiments, the solvent will have a dielectric constant of between about 2 and about 20, or between about 2 and about 10. The content of this organic solvent in the overall composition will complement to 100% of the composition. The solvent may comprise a mixture of solvents including a mixture of an organic solvent and an organic co-solvent. In one embodiment, and the organic co-solvent has a boiling point of less than about 300° C. or less than about 250° C. In other embodiments, the cosolvent has a boiling point of below about 200° C., or below about 130° C. In still another embodiment of the invention, the organic co-solvent has a boiling point of below about 100° C., or below about 80° C. In still other embodiments, the organic co-solvent will have a dielectric constant of a range selected from the group consisting of about 2 to about 40, about 10 to about 40, or typically about 20 to about 30. In some embodiments of the invention, the co-solvent may be present in the composition in an organic co-solvent/organic solvent weight/weight (W/W) ratio of about 1/15 to about 1/2.

In some embodiments, the co-solvent is volatile so as to act as a drying promoter, and is miscible with water and/or with the organic solvent The formulation can also comprise an antioxidizing agent intended to inhibit oxidation in air, this agent being present in a proportion selected from a range consisting of about 0.005 to about 1% (w/v) and about 0.01 to about 0.05%. Crystallization inhibitors which are useful for the invention include but are not limited to: (a) polyvinylpyrrolidone, polyvinyl alcohols, copolymers of vinyl acetate and of 30 vinylpyrrolidone, polyethylene glycols of various grades, benzyl alcohol, 2-pyrrolidones including, but not limited to N-methylpyrrolidone, dimethylsulfoxide, mannitol, glycerol, sorbitol or polyoxyethylenated esters of sorbitan; lecithin or sodium carboxymethylcellulose; a solvent as described herein that is capable of inhibiting crystal formation; acrylic derivatives, such as methacrylates or other polymers derived from acrylice monomers, and others; (b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulfonate or sodium dioctyl sulphosuccinate; or fatty acids (e.g. coconut oil); (c) cationic surfactants, such as water-soluble quaternary ammonium salts; (d) amine salts of formula N—HR'R"R'", in which the R radicals are identical or different optionally hydroxylated hydrocarbon radicals; octadecylamine hydrochloride is one of the cationic surfactants which can be used; (e) non-ionic surfactants, such as optionally polyoxyethylenated esters of sorbitan, e.g. POLYSORBATE 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide; (f) amphoteric surfactants, such as substituted lauryl compounds of betaine; or (g) a mixture of at least two of the compounds listed in (a)-(f) above. In one embodiment of the cristallization inhibitor, a cristallization inhibitor pair will be used. Such pairs include, for example, the combination of a film-forming agent of polymeric type and of a surface-active agent. These agents will be selected from the compounds mentioned above as cristallization inhibitor. In one embodiment of the film-forming agent, the agents are of the polymeric type which include but are not limited to the various grades of polyvinylpyrrolidone, polyvinyl alcohols, and copolymers of vinyl acetate and of vinylpyrrolidone. In one embodiment of the surface-active ager, the agents include but are not limited to those made of non-ionic surfactants; in another embodiment of the surface active agents, the agent is a polyoxyethylenated esters of sorbitan and in yet another embodiment of the surface active agent, the agents include the various grades of POLYSORBATE, for example POLYSORBATE 80.

In another embodiment of the invention, the film-forming agent and the surface-active agent can be incorporated in similar or identical amounts within the limit of the total amounts of crystallization inhibitor mentioned elsewhere In one embodiment of the antioxidizing agents, the agents are those conventional in the art and include but is not limited to butylated hydroxyanisole, butylated hydroxytoluene, ascorbic acid, sodium metabisulphite, propyl gallatte, sodium thiosulfate or a mixture of not more than two of them. The non-active formulation components discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients are added. The volume of the topical formulations applied is not restricted as long as the amount of substance administered is shown to be safe and efficacious. Typically the volume applied depends on the size and weight of the animal as well as the concentration of active, the extent of infestation by parasites and the type of administration. In some embodiments, the volume applied can be of the order of about 0.3 to about 5 ml or about 0.3 ml to about 1 ml. In one embodiment for the volume, the volume is on the order of about 0.5 ml, for cats and on the order of about 0.3 to about 3 ml for dogs, depending on the weight of the animal. In other embodiments, the volume applied may be about 5 ml to about 10 ml, about 5 ml to about 15 ml, about 10 ml to about 20 ml, or about 20 ml to about 30 ml, depending on the size of the animal treated and the concentration of the active agent in the formulation, among other factors. In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type). For spot-on formulations, the carrier can be a liquid carrier vehicle as described in U.S. Pat. No. 6,426,333. In one embodiment, the spot-on formulation comprises a solvent and a co-solvent wherein the solvent may be acetone, acetonitrile, benzyl alcohol, butyl diglycol, dimethylacetamide, dimethylformamide, dipropylene glycol n-butyl ether, propylene glycol monomethyl ether, propylene glycol monoethyl ether, diisobutyl adipate, diisopropyl adipate (also known as CERAPHYL 230), triacetin, butyl acetyle, octyl acetate, propylene carbonate, butylene carbonate, dimethylsulfoxide, organic amides including dimethylformamide and dimethylacetamide, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, ethylene glycol, diethyl phthalate fatty acid esters, such as the diethyl ester or diisobutyl adipate, and a mixture of at least two of these solvents. In another embodiment, the spot-on formulations include a co-solvent that is absolute ethanol, isopropanol or methanol, or a mixture thereof. In another embodiment, the compositions include benzyl alcohol as a co-solvent.

In one embodiment of the invention, the pharmaceutically or veterinarily acceptable carrier of the formulation comprises C1-C10 alcohols or esters thereof (including acetates, such as ethyl acetate, butyl acetate and the like), C10-C18 saturated fatty acids or esters thereof, C10-C18 monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof. The liquid carrier vehicle can optionally contain a cristallization inhibitor including an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, 2-pyrrolidone including N-methylpyrrolidone (NMP), dimethylsulfoxide, polyethylene glycols, benzyl alcohol, mannitol, glycerol, sorbitol, polyoxyethylenated sorbitan esters; lecithin, sodium carboxymethylcellulose, solvents as defined herein that can inhibit the formation of crystals, and acrylic derivatives such acrylates or methacrylates as well as other polymers derived from acrylic monomers, or a mixture of these cristallization inhibitors. Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

2.2 Definitions

Reduced dosage: in the framework of the invention, «reduced dosage» refers to a dosage that is decreased regarding usual recommendation (ie 25 mg/kg/3 months for a dog in Bravecto). In some embodiments, this reduced dosage corresponds to 1/50, 1/10, 1/8, 1/7, 1/5, 1/4, 1/3, 3/8, 1/2 times the regular dosage for a given period of time.

For instance, with Bravecto, a 25 mg/kg dosage is recommended for a dog over a period of 3 months. A reduced dosage thus corresponds for example to less than 12.5, 9.37, 8.33, 5, 3.5, 3, 2.5, 0.5 mg/kg for a period of 3 months, in a single or as multiple administrations.

For a dog receiving fluralaner, this reduced dosage is comprised for example between around 0.5 and around 12.5 mg/kg, preferably between around 2.5 and around 10 mg/kg preferably between around 5 and around 10 mg/kg, preferably between around 7 and around 10 mg/kg.

Around: in the framework of the invention, around refers to a value that is more or less 1%, 2%, 3%, 4%, 5%, 10%, 15%, 20%, 25%, 30% of the target value. For instance, a dosage of around 5 mg/kg refers to a dosage of 5 mg, but also to a dosage comprised between 4.75 and 5.25 mg/kg to dosage comprised between 3.5 to 6.5 mg/kg.

About: in the framework of the invention, about also refers to a value that is more or less 1%, 2%, 3%, 4%, 5%, 10%, 15%, 20%, 25%, 30% of the target value. For instance, a dosage of about 5 mg/kg refers to a dosage of 5 mg, but also to a dosage comprised between 4.75 and 5.25 mg/kg to dosage comprised between 3.5 to 6.5 mg/kg.

In an embodiment, the dosage of 12.5 mg/kg for administration of fluralaner to a dog is specifically excluded.

By "effective amount" or "effective dose" is intended a sufficient amount of a composition of the invention to eradicate or reduce the number of parasites infesting the animal. In one embodiment, an effective amount of the active agent achieves at least 70% efficacy against the target parasite compared to a negative control according to known methods used in the art (animal not treated or treated with a placebo). In other embodiments, an effective amount of the active agent achieves at least 80%, or at least 90% efficacy against the target pests. Preferably, an effective amount of the active agent will achieve at least 95% efficacy against the target pests. In some embodiments, an effective amount of the compounds and compositions of the invention achieve at least 98% or 100% efficacy against the target parasites.

By "palatability" is intended "that is palatable".

2.3 Embodiments

Appropriate vehicle for the active ingredient are the chews disclosed in U.S. Pat. No. 8,628,794-U.S. Pat. No. 8,541,019-US2014094418-and US20180199573A1 (Virbac).

Because of the food effect on the bioavailability of Fluralaner, a pet food composition (or alternatively a liquid formulation for drinking or for mixing with the food) is of particular interest in order to diminish furthermore the required effective amount of fluralaner.

Chews can be as described in patents: WO16073347 from ZOETIS, EZ Med patents—U.S. Pat. Nos. RE43,582, 6,387,381, RE41,108, Novartis patents—U.S. Pat. No. 8,628,794-U.S. Pat. No. 8,541,019-US2014094418, Merial patents—WO2004016252, Bayer patents—U.S. Pat. No. 7,914,816, Piedmont Pharmaceutical—WO2007067582-WO2009064859, Bayer—WO2012049156, Intervet/MSD patents—U.S. Pat. No. 7,914,816, Argenta—WO2014141223. Topical solutions can be as described in patents: Intervet—WO2009024541, EP2190289B. Injectables can be as described in patents: WO16138339, WO16164487, WO2013119442.

3 Fluralaner New Posology

The description of the concepts in this section "Fluralaner new posology" constitutes a description of each of these concepts in combination with each of the concepts disclosed in the other five sections, and/or other portions of this description, and in particular in combination with the concepts "Fluralaner low dose" disclosed in section 1 hereabove.

3.1 Important Features

An advantage of the invention is, at least in some aspects, practicity for targeting the parasite: it offers the same galenic form (for example one soft chew with one fixed effective amount of fluralaner). If the animal is infected with fleas, the treatment can consist in administering only one soft chew to the animal whereas if the animal is infected by ticks (that require a higher effective amount of fluralaner), then the treatment consists in administering 2, 3 or more soft chews to reach the effective amount (depending of the susceptibility of the parasite). The goal is also reached even more efficiently with a paste or a liquid (for which adjustment of the dose is easier) where the user can adjust the effective amount corresponding to the parasitosis diagnosed on the animal.

The posology can be modified to obtain an improved effect of fluralaner, with less toxicity, more efficiency, and/or a tailored use depending on the pet owner's need (protection against fleas only, against ticks only).

3.2 Definitions

Immediate: less than 10, 9, 8, 7, 6, 5, 4, 3 hours.

Rapid: less than 72, 48, 36, 24 hours.

Smart collar: device that is attached to a body part of the animal (ie the neck) and which can release a controlled amount of active product, on a signal. Said signal could be for example a button on the collar, an order from a connected device, a detection of a scratching movement from the animal by a detection device, said the detection device being directly on the collar or on a connected device, such as house assistants (ie Alexa device) etc.

Dangerous environment: In the framework of the invention, a dangerous environment is defined as an environment that is susceptible to host fleas. In another embodiment, said dangerous environment is defined as an environment that is susceptible to host ticks. An environment can also be dangerous against both fleas and ticks.

Tailored to need posology: In the framework of the invention, a tailored to need posology refers to a treatment that is individually and specifically adapted to a specific animal on a specific use. For example, the dosage needed for the treatment of a dog against fleas is 10 times less than the dosage required for a tick. Therefore a tailored to need posology for a treatment against fleas in a dog can be 10 times lower than the dosage needed for a tailored to need posology against ticks in a dog. A tailored to need posology is possible when the treatment is available as a multidose treatment such as breakable tablets, breakable chew, mini treats, treats, add-on for petfood, petfood, oral paste, etc. . . . .

Reduced dosage: in the framework of the invention, «reduced dosage» refers to a dosage that is decreased regarding usual recommendation (ie 25 mg/kg/3 months for a dog in Bravecto). In some embodiments, this reduced dosage corresponds for example to 1/50, 1/10, 1/8, 1/7, 1/5, 1/4, 1/3, 3/8, 1/2 times the regular dosage for a given period of time.

For instance, with Bravecto, a 25 mg/kg dosage is recommended for a dog over a period of3 months. A reduced dosage thus corresponds for example to less than 12.5, 9.37, 8.33, 5, 3.5, 3, 2.5, 0.5 mg/kg for a period of 3 months, in a single or as multiple administrations.

For a dog receiving fluralaner, this reduced dosage is comprised for example between around 0.5 and around 12.5 mg/kg, preferably between around 2.5 and around 10 mg/kg preferably between around 5 and around 10 mg/kg, preferably between around 7 and around 10 mg/kg.

Around: in the framework of the invention, around refers to a value that is more or less 1%, 2%, 3%, 4%, 5%, 10%, 15%, 20%, 25%, 30% of the target value. For instance, a dosage of around 5 mg/kg refers to a dosage of 5 mg, but also to a dosage comprised between 4.75 and 5.25 mg/kg to dosage comprised between 3.5 to 6.5 mg/kg.

About: in the framework of the invention, about also refers to a value that is more or less 1%, 2%, 3%, 4%, 5%, 10%, 15%, 20%, 25%, 30% of the target value. For instance, a dosage of about 5 mg/kg refers to a dosage of 5 mg/kg, but also to a dosage comprised between 4.75 and 5.25 mg/kg to dosage comprised between 3.5 to 6.5 mg/kg.

In an embodiment, the dosage of 12.5 mg/kg for administration of fluralaner to a dog is specifically excluded.

By "effective amount" or "effective dose" is intended a sufficient amount of a composition of the invention to eradicate or reduce the number of parasites infesting the animal. In one embodiment, an effective amount of the active agent achieves at least 70% efficacy against the target parasite compared to a negative control according to known methods used in the art (animal not treated or treated with a placebo). In other embodiments, an effective amount of the active agent achieves at least 80%, or at least 90% efficacy against the target pests. Preferably, an effective amount of the active agent will achieve at least 95% efficacy against the target pests. In some embodiments, an effective amount of the compounds and compositions of the invention achieve at least 98% or 100% efficacy against the target parasites.

3.3 Embodiments

Fluralaner can be administered topically (collar, controlled release collar, smart collar . . . )

Fluralaner can be administered orally (solid or liquid pet food, add on to the regular meal of the animal, chew, treat, etc. . . . )

Fluralaner can be administered with a fatty meal to improve bioavailability. Chew, treat, etc. (see US20140121194 to Sumitomo)

Administration of fluralaner together with a meal, treat, chew at a dose that is decreased by at least 2, 2.5, 3 times as compared to the standard dosage.

Administration of fluralaner together with a calming compound. Said calming compound being for instance a pheromone as described for instance in patents EP1047415B1, EP0948963B1, EP2954886A, EP0724832, EP0958963, WO2015150386, U.S. Pat. No. 6,821,928B2, 8,741,965, 5,709,863 or 9,044,395.

Pheromones are compounds of choice to be combined within a composition containing the fluralaner. It has been observed that a calm animal infested by parasites is easier to treat with fluralaner.

In one embodiment, the invention provide a combination of a composition according to the invention (preferably as a paste or a liquid) and a diagnostic test for the detection and identification of the parasite and a dose range scale indicating to the user the effective amount of active ingredient (and therefore of the composition) required to treat the animal.

A method for protecting an animal from a parasitic invertebrate pest comprising orally or parenterally administering to the animal a pesticidally effective amount of fluralaner, an N-oxide, a salt or an enantiomer thereof, wherein the effective amount to be administered is calculating by identifying (or diagnosing) the parasite(s) and indicating the appropriate effective amount to the user that administer to the animal the effective amount of fluralaner to treat the parasite(s).

The smart use of fluralaner compound is of great importance because a decreased use of such product leads to a better control of the amount of compound used, and thus a decrease in pollution, positive impact on environment.

The posology could be modified to obtain an improved effect of fluralaner, with less toxicity, more efficiency, and/or a tailored use depending on the pet owner's need.

For example, in one aspect, for improving efficacy, while limiting product use and dispersion, the dose amount and posology can be adjusted to limit or adjust the plasma concentration in the animal to at most one of the values, or to within one of the ranges, indicated in this description and corresponding to low dose embodiments in accordance with the invention.

In particular, the administered dose amount can be selected so as to obtain a plasma concentration of the active within a range between a lower limit and an upper limit among these values. For example, the dose can be selected to be low and the posology of charge and maintenance doses is selected and scheduled so that plasma concentration is 4 to 6 times higher than the plasma concentration that would have been expected from the plasma concentration obtained by administering Bravecto according to the conventional protocol, or 2 to 4, 2 to 5, 2 to 6, 2 to 7, 2 to 8, 2 to 9, 2 to 10, 3 to 5, 3 to 6, 3 to 7, 3 to 8, 3 to 10, 4 to 7, 4 to 8, 4 to 9, 4 to 10 times. Plasma concentration in a range of 80 to 150, 90 to 140, 100 to 130, or 80 to250, 80 to 200, 90 to 250, 90 to 200, 100 to 250, 100 to 200 ng/ml can be obtained.

In some embodiments, for efficacy against fleas, administered doses may be selected so as to result in plasma concentration 2, 3, 4, 5, 6, 7, 8, 9, or 10 times lower than the above values and ranges.

In some embodiments, the administered doses and schedule are selected so that the plasma concentration within the above values or ranges in accordance with the present invention is reached at 1, 2, 3, 4, 5, 6, 7 or more days from the start of administration, and be maintained for a duration of a few hours, such as at least 4, 6, 12, 18 hours, or at least 1, 2, 3, 4, 5, 6, 7 days, or at least 1, 2, 3, 4, 5 weeks, or at least 1, 2, 3, 4, 5, 6, 7, 8, 9, 10, 11, 12 months, or for a period of time selected within these ranges, the plasma concentration becoming lower than the lower limit after this time period.

For example, a single charge dose may be followed by maintenance doses of a lower amount, or by a continuously administered dose. Instead of the single charge dose and maintenance doses, a succession of same-amount or progressively varying doses may be administered, or a continuous administration allowing the same pattern of dosage administration and/or the same plasma concentration profile within the ranges characteristic of the present invention. A charging dose can be selected to result in a plasma concentration of at least 1/7, 1/6, 1/5, 1/4, 1/3, 1/2, 2/3, 3/4 of the target plasma concentration in the animal. A second, third, fourth, and/or fifth charging dose of the same or different amount may be administered, for example, at least once a day, or at least 2, 3, 4, 5 times a day, for a duration of 1, 2, 3, 4, 5, 6, 7 days. Also, the charging and maintenance doses can be selected as a function of the corresponding plasma concentration in the animal, for example, each individual charging does resulting in at least 1/5, 1/4, 1/3, 1/2, 2/3, 3/4 of the target plasma concentration in the animal. The maintenance dose may be administered after, or between, the charging doses, for a duration of at least 1, 2, 3, 4, 5, 6, 7 days, or at least 1, 2, 3, 4, 5 weeks, or at least 1, 2, 3, 4, 5, 6, 7, 8, 9, 10, 11, 12 months, or for a period of time within these ranges. The frequency of administration of the maintenance dose may be a day or a fraction of a day, for example 4, 6, 12, 18 hours, a week or a fraction of a week, for example 2, 3, 4, 5, 6 days, or several weeks, such as 1, 2, 3, 4, 5, 6, 7, 8, 9, 10 weeks.

4 Fluralaner New Therapeutic Indications

The description of the concepts in this section "Fluralaner new therapeutic indications" constitutes a description of each of these concepts in combination with each of the concepts disclosed in the other five sections, and/or other portions of this description, and in particular in combination with the concepts "Fluralaner low dose" disclosed in section 1 hereabove.

4.1 Important Features

Subgroups of animals. Each animal in a group or a specie as feline or canine have specificities and several different breeds exists. There are many differences between an animal belonging to a breed versus another animal belonging to another breed within the same specie; For example, an animal of one breed may be susceptible to the toxicity of one active ingredient whereas another animal of another breed of the same specie may not be. It is anticipated that differences exits in terms of susceptibility to the fluralaner and its effects and that the effective amount of fluralaner against a same parasite may differ from one breed to another within the same specie. Without being limited by any particular theory, it is hypothetized that the reason may reside in different physiology of the members of different breeds. The same is considered for the age of an animal in the same breed and the sex of an animal in the same breed.

Therefore the invention is dedicated to the effective amount of fluralaner for an individual inside a determined breed:

For illustrative example: 1) Fluralaner for use in protecting an Abyssinian cat from a parasitic invertebrate pest, wherein fluralaner is administered to said animal at a reduced dosage.

2) Fluralaner for use in protecting an Aegean cat from a parasitic invertebrate pest, wherein fluralaner is administered to said animal at a reduced dosage, said reduced dosage being comprised between 0.025 mg/kg and 12.5 mg/kg, more preferably between 0.5 mg/kg and 9.37 mg/kg.

The list of recognized cat breeds is long and includes: Abyssinian, Aegean, Australian Mist, American Curl, American Bobtail, American Polydactyl, American shorthair, American Wirehair, Arabian Man, Asian, Asian Semi-longhair, Balinese, Bambino, Bengal, Birman, Bombay, Brazilian Shorthair, British Shorthair, British Longhair, Burmese, Burmilla, California Spangled Cat, Chantilly/Tiffany, Chartreux, Clausie, Cheetoh, Colorpoint Shorthair, Cornish Rex, Cymric, Cyprus cat, Devon Rex Doinskoy, Dragon Li, Dwelf, Egyptian Mau, European Shorthair, Exotic Shorthair, German Rex, Havana Brown, Highlander, Himalayan/Colorpoint Persian, Japanese Bobtail, Javanese, Khao Manee, Korat, Kurilian Bobtail, LaPerm, Maine Coon, Manx, Mekong bobtail, Minskin, Munchkin, Nebelung, Napoleon, Norwegian Forest Cat, Ocicat, Ojos Azules, Oregon Rex, Oriental Bicolor, Oriental Shorthair, Oriental Longhair, Persian, Peterbald, Pixie-bob, Ragamuffin, Ragdoll, Russian Blue, Russian Black, White or Tabby, Savannah, Scottish Fold, Selkirk Rex, Serengeti cat, Serrade petit, Siamese, Siberian Singapura, Snowshoe, Sokoke, Somali, Sphynx, Swedish forest cat, Thai, Tonkinese, Toyger, Turkish Angora, Turkish Van, Ukrainian Levkoy, and York Chocolate Cat. But the same applies for every breed.

The list of American Kennel Club recognized breeds includes Affenpinscher, afghan hound, Airedale Terrier, Akita, Alaskan Malamute, American English Coonhound, American Eskimo Dog, American Foxhound, American Staffordshire Terrier, American Water Spaniel, Anatolian Shepherd Dog, Australian Cattle Dog, Australian Shepherd, Australian Terrier, Basenji, Basset Hound, Beagle, Bearded Collie, Beauceron, Bedlington Terrier, Belgian Malinois, Belgian Sheepdog, Belgian Tervuren, Bernese Mountain dog, Bichon Frise, Black and Tan Coonhound, Black Russian Terrier, Bloodhound, Bluetick Coonhound, Border Collie, Border Terrier, Borzoi, Boston Terrier, Bouview des Flandres, Boxer, Boykin Spaniel, Briard, Brittany, Brussels Griffon, Bull Terrier, Bulldog, BuUmastiff, Cairn Terrier, Canaan dog, Cane Corso, Cardigan Welsh Corgi, Cavalier King Charles Spaniel, Cesky Terrier, Chesapeake Bay Retriever, Chihuahua, Chinese Crested, Chinese Shar-Pei, Chow Chow, Cirneco dell'Etna, Clumber Spaniel, Cocker Spaniel, Collie, Curly-Coated Retriever, Dachshund, Dalmatian, Dandie Dinmont Terrier, Doberman Pinscher, Dogue de Bordeaux, English Cocker Spaniel, English Foxhound, English Setter, English Springer Spaniel, English Toy Spaniel, Entlebucher Mountain Dog, Field Spaniel, Finnish Lapphund, Finnish Spitz, Flat-Coated Retriever, French bulldog, German Pinscher, German Shepherd Dog, German Shorthaired Pointer, German Wirehaired Pointer, Giant Schnauzer, Glen of Imaal Terrier, Golden Retriever, Gordon Setter, Great Dane, Great Pyrenees, Greater Swiss Mountain Dog, Greyhound, Harrier, Havanese, Ibizian Hound Icelandic Sheepdog, Irish Red and White Setter, Irish Setter, Irish Terrier, Irish Water Spaniel, Irish Wolfhound, Italian Greyhound, Japanese Chin, Keeshond, Kerry Blue Terrier Komondor, Kuvasz, Labrador Retriever, Lakeland Terrier, Leonberger, Lhasa Apso, Lowchen, Maltese, Manchester Terrier, Mastiff, Miniature Bull Terrier, Miniature Pinscher, Miniature Schnauzer, Neapolitan Mastiff, Newfoundland, Norfolk Terrier, Norwegian Buhund, Norwegian Elkhound, Norwegian Lundehund, Norwich Terrier, Nova Scotia Duk Tolling Retriever, Old English Sheepdog, Otterhound, Papillion, Parson Russell Terrier, Pekingese, Pembroke Welsh Corgi, Petit Basser Griffon Vendeen, Pharaoh Hound, Plott, Pointer, Polish Lowland Sheepdog, Pomeranian, Poodle, Portuguese Water Dog, Pug, Puli, Pyrencan Shepherd, Rat Terrier, Redbone Coonhound, Rhodesian Ridgeback, Rottweiler, Russsell Terrier, Saint Bernard, Saluki, Samoyed, Schipperke, Scottish Deerhound, Scottish Terrier, Sealyham Terrier, Shetland Sheepdog, Shiba Inu, Shih Tzu, Siberian Husky, Silky Terrier, Skye Terrier Smooth Fox Terrier, Soft Coated Wheaten Terrier, Spinone Italiano, Staffordshire Bull Terrier, Standard Schnauzer, Sussex Spaniel, Swedish Vallhund, Tibetan Mastiff, Tibetan Spaniel, Tibetan Terrier, Toy Fox Terrier, Treeing Walker Coonhound, Vizsla, Weimaraner, Welsh Springer Spaniel, Welsh Terrier, West Highland White Terrier, Whippet, Wire Fox Terrier, Wirehaired Pointing Griffon, Xoloitzcuintli, and Yorkshire Terrier. And the same applies for every dog breed.

Animals having digestive issues have a lower tendency to absorb fluralaner (food effect on bioavailability as reported in Walther et al. Parasites & Vectors 2014, 7:84: The effect of food on the pharmacokinetics of oral fluralaner in dogs)

Fluralaner is not degraded in feces of the animals, there is therefore a huge interest to administer exactly the right amount of active ingredient depending on the need at a given moment. To ensure a responsible use, for the animal, as well as for the environment.

4.2 Definitions

In the framework of the invention, a senior animal is an animal that exceeds by more than 60%, 70%, 80% its ordinary lifespan.

4.3 Embodiments

Dog breeds having digestive issues are generally large dog breeds.

A large breed dog is a dog weighing more than 25, more than 30 kg. Large dog breeds are: Alaskan Malamute, American Foxhound, American Staffordshire Terrier, Australian Shepherd, Beauceron, Belgian Shepherd/Malinois, Belgian Shepherd/Sheepdog, Belgian Shepherd/Tervuren, Black and Tan Coonhound, Bloodhound, Bluetick Coonhound, Bouvier des Flandres, Boxer, Briard, Bull Terrier, Chesapeake Bay Retriever, Chinook, Chow Chow, Clumber Spaniel, Collie, Curly-Coated Retriever, Doberman Pinscher, English Coonhound, English Foxhound, English Pointer, English Setter, Entlebucher Mountain Dog, Flat-Coated Retriever, German Shepherd Dog, German Shorthaired Pointer, German Wirehaired Pointer, Giant Schnauzer, Golden Retriever, Gordon Setter, Greyhound, Irish Setter, Irish Water Spaniel, Komondor, Labrador Retriever, Old English Sheepdog, Poodle, Redbone Coonhound, Rhodesian Ridgeback, Saluki, Samoyed, Spinone Italiano, Treeing Walker Coonhound, Vizsla, Weimaraner, Akita, Anatolian Shepherd, Bernese Mountain Dog, Black Russian Terrier, Boerboel, Borzoi, Bullmastiff, Cane Corso, Dogue de Bordeaux, Great Dane, Great Pyrenees, Greater Swiss Mountain Dog, Irish Wolfhound, Kuvasz, Leonberger, Mastiff, Neapolitan Mastiff, Newfoundland Dog, Otterhound, Rottweiler, Saint Bernard, Scottish Deerhound, Tibetan Mastiff.

Small dog bread are dogs weighing less than 15 or 10 kg, for example: Affenpinscher, Australian Terrier, Basenji, Bedlington Terrier, Bichon Frise, Border Terrier, Boston Terrier, Brussels Griffon, Cairn Terrier, Cavalier King Charles Spaniel, Chihuahua, Chinese Crested Dog, Coton de Tulear, Dandie Dinmont Terrier, English Toy Spaniel, Havanese, Italian Greyhound, Japanese Chin, Lakeland Terrier, Lhasa Apso, Lowchen, Maltese, Manchester Terrier, Miniature Dachshund, Miniature Pinscher, Miniature Poodle, Miniature Schnauzer, Norfolk Terrier, Norwegian Lundehund, Norwich Terrier, Papillon, Parson Russell Terrier, Pekingese, Pomeranian, Portuguese Podengo, Pug, Rat Terrier, Schipperke, Scottish Terrier, Sealyham Terrier, Shetland Sheepdog/Sheltie, Shiba Inu, Shih Tzu, Silky Terrier, Smooth Fox Terrier, Tibetan Spaniel, Tibetan Terrier, Toy Fox Terrier, Toy Manchester Terrier, Welsh Terrier, West Highland White Terrier/Westie, Wire Fox Terrier, Yorkshire Terrier.

Medium dog bread are dogs weighing between 10 and 30 kg, for example: Afghan Hound, Airedale Terrier, American Cocker Spaniel, American Eskimo Dog, American Water Spaniel, Australian Cattle Dog, Basset Hound, Beagle, Bearded Collie, Border Collie, Boykin Spaniel, Brittany Spaniel, Canaan Dog, Cardigan Welsh Corgi, Cirneco dell'Etna, Dachshund, Dalmatian, English Bulldog, English Cocker Spaniel, English Springer Spaniel, Field Spaniel, Finnish Lapphund, Finnish Spitz, French Bulldog, German Pinscher, Glen of Imaal Terrier, Harrier, Ibizan Hound, Icelandic Sheepdog, Irish Terrier, Keeshond, Kerry Blue Terrier, Miniature Bull Terrier, Norwegian Buhund, Norwegian Elkhound, Nova Scotia Duck Tolling Retriever, Pembroke Welsh Corgi, Petit Basset Griffon Vendeen, Pharaoh Hound, Plott Hound, Polish Lowland Sheepdog, Portuguese Water Dog, Puli, Pyrenean Shepherd, Schnauzer, Shar-Pei, Siberian Husky, Skye Terrier, Spanish Water Dog, Staffordshire Bull Terrier, Sussex Spaniel, Swedish Vallhund, Welsh Springer Spaniel, Wheaten Terrier, Whippet, Wirehaired Pointing Griffon, Xoloitzcuintli/Mexican Hairless.

Ectoparasites: In particular, the formulations of this invention may be effective against ectoparasites including: flies such as *Haematobia* (Lyperosia) *irritans* (horn fly), *Stomoxys calcitrans* (stable fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus instestinalis, Gastrophilus haemorrhoidalis*, and *Gastrophilus naslis*; lice such as *Bovicola* (*Damalinia*) *bovis, Bovicola equi, Haematopinus asini, Felicola subrostratus, Heterodoxus spiniger, Lignonathus setosus* and *Trichodectes canis*; keds such as *Melophagus ovinus*; mites such as *Psoroptes* spp., *Sarcoptes scabei, Chorioptes bovis, Demodex equi, Cheyleitellia* spp., *Notoedres cati, Trombicula* spp. and *Otodectes cyanotis* (ear mites); ticks such as *Ixodes* spp., *Boophilus* spp., *Rhipicephalus* spp., *Amblyomma* spp., *Dermacentor* spp., *Hyalomma* spp. and *Haemaphysalis* spp.; and fleas such as *Ctenocephalides felis* (cat flea) and *Ctenocephalides canis* (dog flea).

Mosquitos: House mosquito (*Culex*), including *Culex Pipiens* and *Culex restuans* Theobald, Southern mosquito (*Culex quinquefasciatus, Culex fatigans*), Asian tiger mosquito (*Aedes albopictus*), Yellow fever mosquito (*Aedes aegypti*).

5 Fluralaner New Combinations

The description of the concepts in this section "Fluralaner new combinations" constitutes a description of each of these concepts in combination with each of the concepts disclosed in the other five sections, and/or other portions of this description, and in particular in combination with the concepts "Fluralaner low dose" disclosed in section 1 hereabove. In the framework of the invention, a senior animal is an animal that exceeds by more than 60%, 70%, 80% its ordinary lifespan.

5.1 Important Features

Focus on a pyrethroid insecticide, such as flumethrin, Bifenthrin, Cyfluthrins, Cypermethrin, Cyphenothrin, deltamethrin, d-phenothrin, Esfenvalerate, Etofenprox, Fenpropathrin, Gamma-cyhalothrin, Imiprothrin, Lambda-cyhalothrin, Momfluorothrin, Prallethrin, Permethrin, pyrethrins, Tau-fluvalinate, Tefluthrin, Tetramethrin.

Focus on a neonicotinoid, such as imidacloprid, acetamiprid, clothianidin, dinotefuran, nitenpyram, thiacloprid, thiamethoxam.

In a particular embodiments, the isoxazoline is combined with a pyrethroid instecticide, and a neonicotinoid, in particular, with citridiol and flumethrin.

Focus on a compound active against dirofilaria, such as ivemectine, pyrantel, milbemycine, praziquantel, pyrantel, lufenuron, moxidectine, imidacloprid, selamectine, spinosad or other anti-heartworm compounds Fluralaner and a repellent such as citridiol, Methyl anthranilate and other anthranilate-based insect repellents, Benzaldehyde, Dimethyl carbate Dimethyl phthalate, Icaridin, also known as picaridin, Bayrepel, and KBR 3023, Ethyl butylacetylaminopropionate (IR3535 or 3-[N-Butyl-N-acetyl]-aminopropionic acid, ethyl ester), Metofluthrin, Permethrin, SS220, Tricyclodecenyl allyl ether, or natural repellents such as Beautyberry leaves, Birch tree bark, Bog Myrtle (*Myrica gale*), Catnip oil nepetalactone), Citronella oil, Essential oil of the lemon eucalyptus (*Corymbia citriodora*) and its active compound p-menthane-3,8-diol (PMD), Neem oil, Lemongrass, Tea tree oil from the leaves of *Melaleuca alternifolia*, Tobacco, etc. . . . .

Subgroups of parasites: mosquitos, sand fly (phlebotome), ages (aoutas), wasps and hornets Compositions comprising Fluralaner in combination with ectoparasiticides agents.

Compositions comprising Fluralaner in combination with endoparasiticides agents.

Broad protection including environment (protection of the pet owner by the repellant presence of the treated pet)

Include all species, including new companion animals: ferret, toy pig, mouse, rat, hamsters, rabbits, birds, small lizards, snakes . . . .

5.2 Definitions

Fat containing device: In the framework of the invention, a fat containing device refers to any edible (or non-edible) device that can be administered to the target species. Of particular interest are edible devices. Such devices include:

soft chews, treats, fatty tablets, chewable tablets, meal, petfood, candy, edible toy, and the like . . . .

5.3 Embodiments

Among the active ingredients particularly useful to associate with fluralaner are:

A.1 Acetylcholine esterase inhibitors selected from triazemate or from the class of carbamates consisting of aldicarb, alanycarb, benfuracarb, carbaryl, carbofu-ran, carbosulfan, methiocarb, methomyl, oxamyl, pirimicarb, propoxur and thiodi-carb, or from the class of organophosphates consisting of acephate, azinphos-ethyl, azinphos-methyl, chlorfenvinphos, chlorpyrifos, chlorpyrifos-methyl, deme-ton-S-methyl, diazinon, dichlorvos/DDVP, dicrotophos, dimethoate, disulfoton, ethion, fenitrothion, fenthion, isoxathion, malathion, methamidaphos, methi-dathion, mevinphos, monocrotophos, oxymethoate, oxydemeton-methyl, parathion, parathion-methyl, phenthoate, phorate, phosalone, phosmet, phosphami-don, pirimiphos-methyl, quinalphos, terbufos, tetrachlorvinphos, triazophos and trichlorfon;

A.2 GABA-gated chloride channel antagonists selected from the cyclodiene organochlorine endosulfan, N-Ethyl-2,2-dimethylpropionamide-2-(2,6-dichloro-α, α,α-trifluoro-p-tolyl) hydrazon, N-Ethyl-2,2-dichloro-1-methylcyclopropane-carboxamide-2-(2,6-dichloro-α,α,α-trifluoro-p-tolyl) hydrazon or from the class of phenylpyrazoles consisting of acetoprole, ethiprole, fipronil, pyrafluprole, pyriprole, vaniliprole:

A.3 Sodium channel modulators selected from the class of pyrethroids consisting of allethrin, bifenthrin, beta-cyfluthrin, cyfluthrin, lambda-cyhalothrin, cypermethrin, alpha-cypermethrin, beta-cypermethrin, zeta-cypermethrin, deltamethrin, esfenvalerate, etofenprox, fenpropathrin, fenvalerate, flucythrinate, tau-fluvalinate, metofluthrin, permethrin, profluthrin, pyrethrin (pyrethrum), silafluofen and tralomethrin;

A.4 Nicotinic acteylcholine receptor agonists/antagonists selected from nicotin, cartap hydrochloride, thiocyclam or from the class of neonicotinoids consisting of acteamiprid, chlothianidin, dinotefuran, imidacloprid, nitenpyram, spinosad (allosteric agonist), spinetoram (allosteric agonist), thiacloprid, thiamethoxam and AKD-1022;

A.5 Chloride channel activators selected from abamectin, emamectin benzoate, lepimectin or milbemectin;

A.6 Juvenile hormone mimics selected from hydroprene, kinoprene, fenoxycarb or pyriproxyfen;

A.7 Compounds affecting the oxidative phosphorylation selected from diafenthi-uron, fenbutatin oxide, propargite or chlorfenapyr;

A.8 Inhibitors of the chitin biosynthesis selected from buprofezin or from the class of benzylureas consisting of bistrifluron, diflubenzuron, flufenoxuron, hexaflumuron, lufenuron, novaluron and teflubenzuron;

A.9 Moulting disruptors selected from cyromazine or from the class of ecdysone agonists consisting of methoxyfenozide, tebufenozide and azadirachtin;

A.10 Mitochondrial electron transport inhibitors selected from pyridaben, tolfen-pyrad or flufenerim.

A.11 Voltage-dependent sodium channel blockers selected from indoxacarb or metaflumizone.

A.12 Inhibitors of the lipid synthesis selected from spirodiclofen, spiromesifen or spirotetramat.

A.13 group of various compounds consisting of amidoflumet, amitraz, bifenazate, clofentezine, cyenopyrafen, cyflumetofen, etoxazole, flonicamid, flubendiamine, flupyrazophos, hexythiazox, piperonyl butoxide, pymetrozine, pyridalyl, pyriflu-quinazon, chlorantraniliprole 5-Bromo-2-(3-chloro-pyridin-2-yl)-2H-pyrazole-3-carboxylic acid [4-cyano-2-(1-cyclopropyl-ethylcarbamoyO-θ-methyl-phenyl]-amide, 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide, 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide, 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide, 5-Bromo-2-(3-chloro-pyridin-2-yl)-2H-pyrazole-3-carboxylic acid [2,4-dichloro-6-(1-cyclopropyl-ethylcarbamoyl)-phenyl]-amide, 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide, N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester, N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester, N'-(2-{[5-Bromo-2-(3-chloro-pyridin-2-yl)-2H-pyrazole-3-carbonyl]-amino}-5-chloro-S-methyl-benzoyO-N^'-dimethyl-hydrazinecarboxylic acid methyl ester, N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester, N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester, the aminofuranone compounds 4-{[(6-Bromopyrid-3-yl)methyl](2-fluoroethyl)amino}furan-2(5H)-on, 4-{[(6-Fluoropyrid-3-yl)methyl](2,2-difluoroethyl)amino}furan-2(5H)-on, 4-{[(2-chloro1,3-thiazolo-5-yl)methyl](2-fluoroethyl)amino}furan-2(5H)-on, 4-{[(6-chloropyrid-3-yl)methyl](2-fluoroethyl)amino}furan-2(5H)-on, 4-{[(6-chloropyrid-3-yl)methyl](2,2-difluoroethyl)amino}furan-2(5H)-on, 4-{[(6-chloro-5-fluoropyrid-3-yl)methyl](methyl)amino}furan-2(5H)-on, 4-{[(5,6-dichloropyrid-3-yl)methyl](2-fluoroethyl)amino}furan-2(5H)-on, 4-{[(6-chloro-5-fluoropyrid-3-yl)methyl](cyclopropyl)amino}furan-2(5H)-on, 4-{[(6-chloropyrid-3-yl)methyl](cyclopropyl)amino}furan-2(5H)-on and 4-{[(6-chloropyrid-3-yl)methyl](methyl)amino}furan-2(5H)-on, the malononitrile compounds 2-(2,2,3,3,4,4,5,5-octafluoropentyl)-2-(3,3,3-trifluoro-propyl)malononitrile ($CF_2H—CF_2—CF_2—CF_2—CH_2—C(CN)_2—CH_2—CH_2—CF_3$) and 2-(2,2,3,3,4,4,5,5-octafluoropentyl)-2-(3,3,4,4,4-pentafluorobutyl)-malonodinitrile ($CF_2H—CF_2—CF_2—CF_2—CH_2—C(CN)_2—CH_2—CH_2—CF_2—CF_3$), the alkynylether compound 4-but-2-ynyloxy-6-(3,5-dimethyl-piperidin-1-yl)-2-fluoro-pyrimidine, the phtalamid compound (R)-,(S)-

3-chlor-N1-{2-methyl-4-[1,2,2,2-tetrafluor-1-(trifluormethyl)ethyl]phenyl}-N2-(1-methyl-2-methylsulfonylethyl)phthalamid, the pyripyropene compound cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester and the pyridazine compound 8-(2-vyclopropylmethoxy-4-trifluoromethyl-phenoxy)-3-(6-trifluoromethyl-pyridazin-3-yl)-3-aza-bicyclo[3.2.1]octane in synergistically effective amounts.

11. A azoles such as triazoles, imidazoles, pyrazoles, thiazoles and oxazoles selected from the group consisting of azaconazole, benomyl, bitertanol, bromuconazole, carbendazim, cyproconazole, cyazofamid, difenoconazole, diniconazole, diniconazole-M, enilconazole, epoxiconazole, ethaboxam, etridiazole, fluquinconazole, fenbuconazole, flusilazole, flutriafol, fuberidazole, hexaconazole, hymexazole, imazalil, imazalil-sulfphate, imibenconazole, ipconazole, metconazole, myclobutanil, oxpoconazol, paclobutrazol, pefurazoate, penconazole, prochloraz, propiconazole, prothioconazole, simeconazole, triadimefon, triadimenol, tebuconazole, tetraconazole, thiabendazole, triticonazole, triflumizole, uniconazol and 1-(4-chlorophenyl)-2-([1,2,4]triazol-1-yl)-cycloheptanol;

11. B strobilurins selected from the group consisting of azoxystrobin, dimoxystrobin, enestroburin, fluoxastrobin, kresoxim-methyl, methominostrobin, orysastrobin, picoxystrobin, pyraclostrobin, pyribencarb, trifloxystrobin, methyl 2-(ortho-(2,5-dimethylphenyloxymethylene)phenyl)-3-methoxyacrylate, 2-(2-(6-(3-chloro-2-methyl-phenoxy)-5-fluoro-pyrimidin-4-yloxy)-phenyl)-2-methoxyimino-N-methyl-acetamide and 3-methoxy-2-(2-(N-(4-methoxy-phenyO-cyclo-propanecarboximidoylsulfanylmethyO-phenyl)-acrylic acid methyl ester;

11. C carboxamides selected from the group consisting of benalaxyl, benalaxyl-M, benodanil, bixafen, boscalid, carboxin, carpropamid, dimethomorph, diclocymet, fenhexamid, fluopyram, flutolanil, furametpyr, flumorph, flumetover, fluopicolide (picobenzamid), mandipropamid, mepronil, metalaxyl, mefenoxam, ofurace, oxadixyl, oxycarboxin, oxytetracyclin, penthiopyrad, silthiofam, thifluzamide, tiadinil, zoxamide, 5-fluoro-1,3-dimethyl-1H-pyrazole-4-carboxylic acid [2-(1,2-dimethyl-propyl)-phenyl]-amide, methyl-3-(4-chlorophenyl)-3-(2-isopropoxycarbonylamino-3-methylbutyrylamino)propionate, 2-chloro-N-(1,1,3-trimethyl-indan-4-yl)-nicotinamide, N-(3-ethyl-3,5-5-trimethyl-cyclohexyl)-3-formylamino-2-hydroxy-benzamide, N-(2-{4-[3-(4-chlorophenyl)prop-2-ynyloxy]-3-methoxyphenyl}ethyl)-2-methanesulfonylamino-3-methylbutyramide, N-(2-{4-[3-(4-chlorophenyl)-prop-2-ynyloxy]-3-methoxyphenyl}ethyl)-2-ethanesulfonylamino-3-methyl-butyramide, N-(6-methoxy-pyridin-3-yl) cyclopropane-carboxamide, 2-amino-4-methyl-thiazole-5-carboxamide, N-(2-cyanophenyl)-3,4-dichloroisothiazole-5-carboxamide, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(3',4'-dichloro-5-fluorobiphenyl-2-yl)-3-difluoromethyl-1-methylpyrazole-4-carboxamide; N-(3',4'-dichloro-4-fluorobiphenyl-2-yl)-3-difluoromethyl-1-methylpyrazole-4-carboxamide, N-(3',4'-dichloro-5-fluorobiphenyl-2-yl)-3-difluoromethyl-1-methylpyrazole-4-carboxamide, N-(2-(1,3-dimethylbutyl)-phenyl)-1,3-dimethyl-5-fluoro-1H-pyrazole-4-carboxamide, N-(4'-chloro-3',5-difluoro-biphenyl-2-yl)-3-difluoromethyl-1-methyl-1H-pyrazole-4-carbox amide, N-(4'-chloro-3',5-difluoro-biphenyl-2-yl)-3-trifluoromethyl-1-methyl-1H-pyrazole-4-carbox amide, N-(3',4'-dichloro-5-fluoro-biphenyl-2-yl)-3-trifluoromethyl-1-methyl-1H-pyrazole-4-carbox amide, N-(3',5-difluoro-4'-methyl-biphenyl-2-yl)-3-difluoromethyl-1-methyl-1H-pyrazole-4-carboxamide, N-(3',5-difluoro-4'-methyl-biphenyl-2-yl)-3-trifluoromethyl-1-methyl-1H-pyrazole- 4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoromethyl-1-methyl-1H-pyrazole-4-carboxamide, N-(2',4'-difluorobiphenyl-2-yl)-1-methyl-3-trifluoromethyl-1H-pyrazole-4-carboxamide, N-(2',4'-dichlorobiphenyl-2-yl)-1-methyl-3-trifluoromethyl-1H-pyrazole-4-carboxamide, N-(2',4'-difluorobiphenyl-2-yl)-3-difluoromethyl-1-methyl-1H-pyrazole-4-carboxamide, N-(2',4'-dichlorobiphenyl-2-yl)-3-difluoromethyl-1-methyl-1H-pyrazole-4-carboxamide, N-(2',5'-difluorobiphenyl-2-yl)-1-methyl-3-trifluoromethyl-1H-pyrazole-4-carboxamide, N-(2',5'-dichlorobiphenyl-2-yl)-1-methyl-3-trifluoromethyl-1H-pyrazole-4-carboxamide, N-(2',5'-difluorobiphenyl-2-yl)-3-difluoromethyl-1-methyl-1H-pyrazole-4-carboxamide, N-(2',5'-dichlorobiphenyl-2-yl)-3-difluoromethyl-1-methyl-1H-pyrazole-4-carboxamide, N-(3',5'-difluoro-biphenyl-2-yl)-1-methyl-3-trifluoromethyl-1H-pyrazole-4-carboxamide, N-(3',5'-dichlorobiphenyl-2-yl)-1-methyl-3-trifluoromethyl-1H-pyrazole-4-carboxamide, N-(3',5'-difluorobiphenyl-2-yl)-3-difluoromethyl-1-methyl-1H-pyrazole-4-carboxamide, N-(3',5'-dichlorobiphenyl-2-yl)-3-difluoromethyl-1-methyl-1H-pyrazole-4-carboxamide, N-(3'-fluorobiphenyl-2-yl)-1-methyl-3-trifluoromethyl-1H-pyrazole-4-carboxamide, N-(3'-chlorobiphenyl-2-yl)-1-methyl-3-trifluoromethyl-1H-pyrazole-4-carboxamide; N-(3'-fluorobiphenyl-2-yl)-3-difluoromethyl-1-methyl-1H-pyrazole-4-carboxamide, N-(3'-chlorobiphenyl-2-yl)-3-difluoromethyl-1-methyl-1H-pyrazole-4-carboxamide, N-(2'-fluorobiphenyl-2-yl)-1-methyl-3-trifluoromethyl-1H-pyrazole-4-carboxamide, N-(2'-chlorobiphenyl-2-yl)-1-methyl-3-trifluoromethyl-1H-pyrazole-4-carboxamide, N-(2'-fluorobiphenyl-2-yl)-3-difluoromethyl-1-methyl-1H-pyrazole-4-carboxamide, N-(2'-chlorbiphenyl-2-yl)-3-difluoromethyl-1-methyl-1H-pyrazole-4-carboxamide; N-(2'-fluoro-4'-chloro-5'-methylbiphenyl-2-yl)-1-methyl-3-trifluoromethyl-1H-pyrazole-4-carboxamide, N-(3',4',5'-trifluorobiphenyl-2-yl)-1-methyl-3-trifluoromethyl-1H-pyrazole-4-carboxamide, N-(3',4',5'-trifluorobiphenyl-2-yl)-1-methyl-3-difluoromethyl-1H-pyrazole-4-carboxamide, N-(2',4',5'-trifluorobiphenyl- 2-yl)-1-methyl-3-difluoromethyl-1H-pyrazole-4-carboxamide, N-(3',4',5'-trifluorobiphenyl-2-yl)-3-chlorofluoromethyl-1-methyl-1H-pyrazole-4-carboxamide, N-[2-(1,1,2,3,3,3-hexafluoropropoxy)phenyl]-1-methyl-3-trifluoromethyl-1H-pyrazole-4-carboxamide, N-[2-(1,1,2,3,3,3-hexafluoropropoxy)-phenyl]-3-difluoromethyl-1-methyl-1H-pyrazole-4-carboxamide, N-[2-(2-chloro-1,1,2-trifluoroethoxy)phenyl]-1-methyl-3-trifluoromethyl-1H-pyrazole-4-carboxamide, N-[2-(2-chlor-1,1,2-trifluoroethoxy)phenyl]-3-difluoromethyl-1-methyl-1H-pyrazole-4-carboxamide, N-[2-(1,1,2,2-tetrafluoroethoxy)phenyl]-3-difluoromethyl-1-methyl-1H-pyrazole-4-carboxamide, N-[2-(1,1,2,2-tetrafluoroethoxy)phenyl]-1-methyl-3 -trifluoromethyl-1H-pyrazole-4-carboxamide, N-(4'-(trifluoromethylthio)biphenyl-2-yl)-3-difluoromethyl-1-methyl-1H-pyrazole-4-carboxamide, N-(4'-(trifluoromethylthio)biphenyl-2-yl)-1-methyl-3-trifluoromethyl-1H-pyrazole-4-carboxamide and N-(2-bicycloprop-2-ylphenyl)-3-difluoromethyl-1-methyl-1H-pyrazole-4-carboxamide; heterocyclic compounds selected from the group consisting of acibenzolar-S-methyl, anilazine, aldimorph, blasticidin-S, bupirimate, captafol, captan, chinomethionat, cyprodinil, dazomet, debacarb, diclomezine, difenzoquat, difenzoquat-methylsulphat, diflumetorim, dodemorph, dodemorph-acetate, famoxadone, fenamidone, fenarimol, ferimzone, fenpiclonil, fenpropidin, fenpropimorph, fludioxonil, fluazinam, fluoroimid, folpet, fenoxanil, iprodione, mepanipyrim, nitrapyrin, nuarimol, octhilinone, oxolinic acid, piperalin, probenazole, procymidone, proquinazid, pyrifenox, pyrimethanil, pyroquilon, quinoxyfen, tricyclazole, triforine, tridemorph, vinclozolin, 5-chloro-7-(4-methylpiperidin-1-yl)-6-(2,4,6-trifluorophenyl)-[1,2,4]triazolo[1,5-a]pyrimidine, 6-(4-tert-butylphenyl)-5-methyl-[1,2,4]triazolo[1,5-a]pyrimidine-7-ylamine, 5-methyl-6-(3,5,5-trimethyl-hexyl)-[1,2,4]triazolo[1,5-a]pyrimidine-7-ylamine, 5-methyl-6-octyl-[1,2,4]triazolo[1,5-a]pyrimidine-7-yl-amine, 6-methyl-5-octyl-[1,2,4]tri-azolo[1,5-a]pyrimidine-7-yl-amine, 6-ethyl-5-octyl-[1,2,4]triazolo[1,5-a]pyrimidine-7-yl-amine, 5-ethyl-6-octyl-[1,2,4]triazolo[1,5-a]pyri-midine-7-ylamine, 5-ethyl-6-(3,5,5-trimethyl-hexyl)-[1,2,4]triazo-lo[1,5-a]pyrimi-dine-7-ylamine, 6-octyl-5-propyl-[1,2,4]triazolo[1,5-a]pyrimidine-7-yl-amine, 5-methoxy-methyl-6-octyl-[1,2,4]triazolo[1,5-a]pyrimidine-7-yl-amine, 6-octyl-5-trifluoromethyl-[1,2,4]triazolo[1,5-a]pyrimidine-7-yl-amine and 5-trifluoromethyl-6-(3,5,5-trimethyl-hexyl)-[1,2,4]tri-azolo[1,5-a]pyrimidine-7-ylamine, 2,3,5,6-tetrachloro-4-methanesulfonyl-pyridine, 3,4,5-trichloro-pyridine-2,6-di-carbonitrile, N-(1-(5-bromo-3-chloro-pyridin-2-yl)-ethyl)-2,4-dichloro-nicotinamide, N-((5-bromo-3-chloro-pyridin-2-yl)-methyl)-2,4-dichloro-nicotinamide, 2-butoxy-6-iodo-3-propylchromen-4-one and N,N-dimethyl-3-(3-bromo-6-fluoro-2-methylindole-1-sulfonyl)-[1,2,4]triazole-1-sulfonamide; arbamates selected from the group consisting of diethofencarb, ferbam, flubenthiavalicarb, iprovalicarb, mancozeb, maneb, metam, methasulphocarb, metiram, propamocarb, propamocarb hydrochlorid, propineb, thiram, zineb, ziram, 4-fluorophenyl N-(1-(1-(4-cyanophenyl)ethanesulfonyl)but-2-yl)carbamate, methyl 3-(4-chlorophenyl)-3-(2-isopropoxycarbonylamino-3-methyl-butyrylamino) various fungicides selected from the group of antibiotics comprising kasugamycin, kasugamycin-hydrochlorid-hydrat, mildiomycin, streptomycin, polyoxin and validamycin A; the group of nitrophenyl derivatives comprising binapacryl, dinocap, dinobuton, dicloran, nitrothal-isopropyl and tecnazen; the group of sulfur-containing heterocyclyl compounds comprising dithianon and isoprothiolane; the group of organometallic compounds comprising fentin salts; the group oforganophosphorus compounds comprising edifenphos, iprobenfos, fosetyl, fosetyl-aluminum, phosphorous acid and its salts, pyrazophos and tolclofos-methyl; the group of organochlorine compounds comprising chlorothalonil, dichlofluanid, dichlorophen, pentachlorophenol and its salts, flusulfamide, hexachlorobenzene, phthalide, pencycuron, quintozene, thiophanate-methyl and tolylfluanid; the group of inorganic active compounds comprising Bordeaux mixture, copper acetate, copper hydroxide, copper oxychloride, basic copper sulfate, oxin-copper and sulfur; and/or selected from a group of various fungicides consisting of biphenyl, bronopol, cyflufenamid, cymoxanil, diphenylamine, dimethirimol, dodine, dodine free base, ethirimol, furalaxyl, iminoctadine, iminoctadine-triacetate, iminoctadine-tris(albesilate), guazatine, guazatine-acetate, metrafenone, prohexadione calcium, spiroxamine guanidine, N-(4-chloro-2-nitro-phenyl)-N-ethyl-4-methyl-benzenesulfon-amide, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluormethyl-4-(3-trimethyl-silanyl-propoxy)-phenyl)-N-ethyl-N-methyl formamidine and N'-(5-difluormethyl-2-methyl-4-(3-trimethylsilanyl-propoxy)-phenyl)-N-ethyl-N-methyl formamidine; in a synergistically effective amount.

Pesticidal active isoxazoline compounds have been described in WO05/085219, WO2007/075459, WO2008/019760 and WO2008/012027. Further isoxazoline compounds comprising annelated bicyclic moieties, as an naphtyl group, are disclosed in WO2007/079162. Preparation methods are described in WO 2007/074789 and WO 2007/094313. In general, pesticidal active isoaxzoline compounds are also described in JP 2007/016017, JP 2007/106756, WO 2005/085216, WO 2007/026965, WO 2007/105814, WO 2007/125984, WO 2007/026965, JP 2008-239611, WO 2008108448, WO 2009/005015, WO 2009/035004, WO 2008/150393, WO 2008/154528, WO 2009/002809, WO 2009/003075, WO 2009/025983, WO 2009/051956, WO 2009/022746, WO 2009/049846, WO 2008/126665, US 2008/00262057 and WO 2009/024541. The prior art does not disclose pesticidal mixtures comprising selective isoxazoline compounds according to the present invention showing unexpected and synergistic effects in combination with other pesticidically active compounds.

Benalaxyl, methyl N-(phenylacetyl)-N-(2,6-xylyl)-DL-alaninate (DE2903612); metalaxyl, methyl N-(methoxyacetyl)-N-(2,6-xylyl)-DL-alaninate (GB1500581); ofurace, (RS)-α-(2-chloro-N-2,6-xylylacetamido)-γ-butyrolactone [CAS RN 58810-48-3]; oxadixyl; N-(2,6-dimethylphenyl)-2-methoxy-N-(2-oxo-3-oxazolidinyl)acetamide (GB2058059); aldimorph, “4-alkyl-2,5(or 2,6)-dimethylmorpholine”, comprising 65-75% of 2,6-dimethylmorpholine and 25-35% of 2,5-dimethylmorpholine, comprising more than 85% of 4-dodecyl-2,5(or 2,6)-dimethylmorpholine, where “alkyl” also includes octyl, decyl, tetradecyl and hexadecyl, with a cis/trans ratio of 1:1 [CAS RN 91315-15-0]; dodine, 1-dodecylguanidinium acetate (Plant Dis. Rep., Vol. 41, p. 1029 (1957)); dodemorph, 4-cyclododecyl-2,6-dimethylmorpholine (DE-A1198125); fenpropimorph, (RS)-cis-4-[3-(4-tert-butylphenyl)-2-methylpropyl]-2,6-dimethylmorpholine (DE-A 27 52 096); fenpropidin, (RS)-I-[3-(4-tert-butylphenyl)-2-methylpropyl]piperidine (DE-A 27 52 096); guazatine, mixture of the reaction products from the amidation of technical grade iminodi(octamethylene) diamine, comprising various guanidines and polyamines [CAS RN 108173-90-6]; iminoctadine, 1,1'-iminodi(octamethylene)diguanidine (Congr. Plant Pathol., 1., p. 27 (1968); spiroxamine, (8-tert-butyl-1,4-dioxaspiro[4.5]dec-2-yl)diethylamine (EP-A 281 842); tridemorph, 2,6-dimethyl-4-tridecylmorpholine (DE-A 1 1 64 152); pyrimethanil, 4,6-dimethylpyrimidin-2-ylphenylamine (DD-A 151 404); mepanipyrim, (4-methyl-6-prop-1-ynylpyrimidin-2-yl)phenylamine (EP-A 224 339); cyprodinil, (4-cyclopropyl-6-methylpyrimidin-2-yl)phenylamine (EP-A 310 550); cycloheximide, 4-{(2R)-2-[(1S,3S,5S)-3,5-dimethyl-2-oxocyclohexyl]-2-hydroxyethyl}pi-peridine-2,6-dione [CAS RN 66-81-9]; griseofulvin, 7-chloro-2',4,6-trimethoxy-6'-methylspiro[benzofuran-2(3H),1'-cyclohex-2'-ene]-3,4'-dione [CAS RN 126-07-8]; kasugamycin, 3-O-[2-amino-4-[(carboxyiminomethyl)amino]-2,3,4,6-tetradeoxy-α-D-arabino-hexopyranosyl]-D-chiro-inositol [CAS RN 6980-18-3]; natamycin, (8E,14E,16E,18E,20E)-(1R,3S,5R,7R,12R,22R,24S,25R,26S)-22-(3-amino-3,6-dideoxy-β-D-mannopyranosyloxy)-1,3,26-trihydroxy-12-methyl-10-oxo-6,11,28-trioxatricyclooctacosa-8,14,16,18,20-pentaene-25-carboxylic acid [CAS RN 7681-93-8]; polyoxin, 5-(2-amino-5-O-carbamoyl-2-deoxy-L-xylonamido)-1-(5-carboxy-1,2,3,4-tetrahydro-2,4-dioxopyrimidin-1-yl)-1,5-dideoxy-β-D-allofuranuronic acid [CAS RN 22976-86-9]; streptomycin, 1,1'-{1-L-(1,3,5/2,4,6)-4-[5-deoxy-2-O-(2-deoxy-2-methylamino-α-L-glucopyranosyl)-3-C-formyl-α-L-lyxofuranosyloxy]-2,5,6-trihydroxycyclohex-1,3-ylene}diguanidine (J. Am. Chem. Soc. Vol. 69, p. 1234 (1947)); bitertanol, β-([1,1'-biphenyl]-4-yloxy)-α-(1,1-dimethylethyl)-1H-1,2,4-triazole-1-ethanol (DE-A 23 24 020); bromuconazole, 1-[[4-bromo-2-(2,4-dichlorophenyl) tetrahydro-2-furanyl]methyl]-1H-1,2,4-triazole (Proc. 1990 Br. Crop. Prot. Conf.—Pests Dis. Vol. 1, p. 459); cyproconazole, 2-(4-chlorophenyl)-3-cyclopropyl-1-[1,2,4]triazol-1-ylbutan-2-ol (U.S. Pat. No. 4,664,696); difenoconazole, 1-{2-[2-chloro-4-(4-chlorophenoxy)phenyl]-4-methyl-[1,3]dioxolan-2-ylmethyl]-1H-[1,2,4]triazole (GB-A2098607); diniconazole, (βE)-β-[(2,4-dichlorophenyl) methylene]-α-(1,1-dimethylethyl)-1 H-1,2,4-triazole-1-ethanol (Noyaku Kagaku, 1983, Vol. 8, p. 575); enilconazole (imazalil), 1-[2-(2,4-dichlorophenyl)-2-(2-propenyloxy) ethyl]-1H-imidazole (Fruits, 1973, Vol. 28, p. 545); epoxiconazole, (2RS,3SR)-1-[3-(2-chlorophenyl)-2,3-epoxy-2-(4-fluorophenyl)propyl]-1H-1,2,4-triazole (EP-A 196 038); fenbuconazole, α-[2-(4-chlorophenyl)ethyl]-α-phenyl-1H-1,2,4-triazole-1-propanenitrile (Proc. 1988 Br. Crop Prot. Conf.—Pests Dis., Vol. 1, p. 33); fluquinconazole, 3-(2,4-dichlorophenyl)-6-fluoro-2-[1,2,4]-triazol-1-yl-3H-quinazolin-4-one (Proc. Br. Crop Prot. Conf.-Pests Dis., 5-3, 41 1 (1992)); flusilazole, 1-{[bis(4-fluorophenyl)methylsilanyl] methyl}-1H-[1,2,4]triazole (Proc. Br. Crop Prot. Conf.-Pests Dis., Vol. 1, p. 413 (1984)); flutriafol, α-(2-fluorophenyl)-α-(4-fluorophenyl)-1H-1,2,4-triazole-1-ethanol (EP-A 15756); hexaconazole, 2-(2,4-dichlorophenyl)-1-[1,2,4]triazol-1-ylhexan-2-ol (CAS RN 79983-71-4); ipconazole, 2-[(4-chlorophenyl)methyl]-5-(1-methylethyl)-1-(1H-1,2,4-triazol-1-yl-methyl)cyclopentanol (EP-A 267 778), metconazole, 5-(4-chlorobenzyl)-2,2-dimethyl-1-[1,2,4]triazol-1-ylmethylcyclopentanol (GB 857 383); myclobutanil, 2-(4-chlorophenyl)-2-[1,2,4]triazol-1-ylmethylpentanenitrile (CAS RN 88671-89-0); penconazole, 1-[2-(2,4-dichlorophenyl)pentyl]-1H-[1,2,4]triazole (Pesticide Manual, 12th Ed. 2000, p. 712); propiconazole, 1-[[2-(2,4-dichlorophenyl)-4-propyl-1,3-dioxolan-2-yl]methyl]-1H-1,2,4-triazole (BE 835 579); prochloraz, N-(propyl-[2-(2,4,6-trichlorophenoxy)ethyl])imidazole-1-carboxamide (U.S. Pat. No. 3,991,071); prothioconazole, 2-[2-(1-chlorocyclopropyl)-3-(2-chlorophenyl)-2-hydroxypropyl]-2,4-dihydro[1,2,4] triazole-3-thione (WO 96/16048); simeconazole, α-(4-fluorophenyl)-α-[(trimethylsilyl)methyl]-1H-1,2,4-triazole-1-ethanol [CAS RN 149508-90-7], tebuconazole, 1-(4-chlorophenyl)-4,4-dimethyl-3-[1,2,4]triazol-1-ylmethylpentan-3-ol (EP-A 40 345); tetraconazole, 1-[2-(2,4-dichlorophenyl)-3-(1,1,2,2-tetrafluoroethoxy)propyl]-1H-1,2,4-triazole (EP-A 234 242); triadimefon, 1-(4-chlorophenoxy)-3,3-dimethyl-1-(1H-1,2,4-triazol-1-yl)-2-butanone (BE793867); triadimenol, β-(4-chlorophenoxy)-α-(1,1-dimethylethyl)-1H-1,2,4-triazole-1-ethanol (DE-A 324010); triflumizol, (4-chloro-2-trifluoromethylphenyl)-(2-propoxy-1-[1,2,4]triazol-1-ylethylidene)-amine (JP-A 79/119 462); triticonazole, (5E)-5-[(4-chlorophenyl)methylene]-2,2-dimethyl-1-(1H-1,2,4-triazol-1-ylmethyl)cyclopentanol (FR 26 41 277); iprodione, N-isopropyl-3-(3,5-dichlorophenyl)-2,4-dioxoimidazolidine-1-carboxamide (GB 13 12 536); myclozolin, (RS)-3-(3,5-dichlorophenyl)-5-methoxymethyl-5-methyl-1,3-oxazolidine-2,4-dione [CAS RN 54864-61-8]; procymidone, N-(3,5-dichlorophenyl)-1,2-dimethylcyclopropane-1,2-dicarboximide (U.S. Pat. No. 3,903,090); vinclozolin, 3-(3,5-dichlorophenyl)-5-methyl-5-vinyloxazolidine-2,4-dione (DE-A 22 07576); ferbam, iron(3+) dimethyldithiocarbamate (U.S. Pat. No. 1,972,961); nabam, disodium ethylenebis(dithiocarbamate) (U.S. Pat. No. 2,317,765); maneb, manganese ethylenebis (dithiocarbamate) (U.S. Pat. No. 2,504,404); mancozeb, manganese ethylenebis(dithiocarbamate) polymer complex zinc salt (GB 996 264); metam, methyldithiocarbaminic acid (U.S. Pat. No. 2,791,605); metiram, zinc ammoniate ethylenebis(dithiocarbamate) (U.S. Pat. No. 3,248,400); propineb, zinc propylenebis(dithiocarbamate) polymer (BE 611 960); polycarbamate, bis(dimethylcarbamodithioato-κS,κS')[μ-[[1,2-ethanediylbis[carbamodithioato-κS,κS' ]](2-)]]di[zinc][CAS RN 64440-88-6]; thiram, bis(dimethylthiocarbamoyl) disulfide (DE-A 642 532); ziram, dimethyldithiocarbamate [CAS RN 137-30-4]; zineb, zinc ethylenebis(dithiocarbamate) (U.S. Pat. No. 2,457,674); anilazine, 4,6-dichloro-N-(2-chlorophenyl)-1,3,5-triazine-2-amine (U.S. Pat. No. 2,720,480); benomyl, N-butyl-2-acetylaminobenzimidazole-1-carboxamide (U.S. Pat. No. 3,631,176); boscalid, 2-chloro-N-(4'-chlorobiphenyl-2-yl) nicotinamide (EP-A 545 099); carbendazim, methyl (1H-benzimidazol-2-yl)carbamate (U.S. Pat. No. 3,657,443); carboxin, 5,6-dihydro-2-methyl-N-phenyl-1,4-oxathiine-3-carboxamide (U.S. Pat. No. 3,249,499); oxycarboxin, 5,6-dihydro-2-methyl-1,4-oxathiine-3-carboxanilide 4,4-dioxide (U.S. Pat. No. 3,399,214); cyazofamid, 4-chloro-2-cyano-N,N-dimethyl-5-(4-methylphenyl)-1H-imidazole-1-sulfonamide (CAS RN 120116-88-3]; dazomet, 3,5-dimethyl-1,3,5-thiadiazinane-2-thione (Bull. Soc. Chim. Fr. Vol. 15, p. 891 (1897)); diflufenzopyr, 2-{1-[4-(3,5-difluorophenyl)semicarbazono]ethyl}nicotinic acid [CAS RN 109293-97-2]; dithianon, 5,10-dioxo-5,10-dihydronaphtho [2,3-b][1,4]dithiin-2,3-dicarbonitrile (GB 857 383); famoxadone, (RS)-3-anilino-5-methyl-5-(4-phenoxyphenyl)-1,3-oxazolidine-2,4-dione [CAS RN 131807-57-3];

fenamidone, (S)-1-anilino-4-methyl-2-methylthio-4-phenylimidazolin-5-one [CAS RN 161326-34-7]; fenarimol, α-(2-chlorophenyl)-α-(4-chlorophenyl)-5-pyrimidinemethanol (GB 12 18 623); fuberidazole, 2-(2-furanyl)-1H-benzimidazole (DE-A 12 09 799); flutolanil, α,α,α-trifluoro-3'-isopropoxy-o-toluanilide (JP 1104514); furametpyr, 5-chloro-N-(1,3-dihydro-1,1,3-trimethyl-4-isobenzofuranyl)-1,3-dimethyl-1H-pyrazole-4-carboxamide [CAS RN 123572-88-3]; isoprothiolane, diisopropyl 1,3-dithiolan-2-ylidenemalonate (Proc. Insectic. Fungic. Conf. 8. Vol. 2, p. 715 (1975)); mepronil, 3'-isopropoxy-o-toluanilide (U.S. Pat. No. 3,937,840); nuarimol, α-(2-chlorophenyl)-α-(4-fluorophenyl)-5-pyrimidinemethanol (GB 12 18 623); fluopicolide (picobenzamid), 2,6-dichloro-N-(3-chloro-5-trifluoromethylpyridin-2-ylmethyl)benzamide (WO 99/42447); probenazole, 3-allyloxy-1,2-benzothiazole 1,1-dioxide (Agric. Biol. Chem. Vol. 37, p. 737 (1973)); proquinazid, 6-iodo-2-propoxy-3-propylquinazolin-4(3H)-one (WO 97/48684); pyrifenox, 2',4'-dichloro-2-(3-pyridyl) acetophenone (EZ)-O-methyloxime (EP 49 854); pyroquilon, 1,2,5,6-tetrahydropyrrolo[3,2,1-ij]quinolin-4-one (GB 139 43 373) quinoxyfen, 5,7-dichloro-4-(4-fluorophenoxy)quinoline (U.S. Pat. No. 5,240,940); silthiofam, N-allyl-4,5-dimethyl-2-(trimethylsilyl)thiophene-3-carboxamide [CAS RN 175217-20-6]; thiabendazole, 2-(1,3-thiazol-4-yl)benzimidazole (U.S. Pat. No. 3,017,415); thifluzamide, 2',6'-dibromo-2-methyl-4'-trifluoromethoxy-4-trifluoromethyl-1,3-thiazole-5-carboxanilide [CAS RN 130000-40-7]; thiophanate-methyl, 1,2-phenylenebis(iminocarbonothioyl) bis(dimethylcarbamate) (DE-A 19 30 540); tiadinil, 3'-chloro-4,4'-dimethyl-1,2,3-thiadiazole-5-carboxanilide [CAS RN 223580-51-6]; tricyclazole, 5-methyl-1,2,4-triazolo[3,4-b][1,3]benzothiazole [CAS RN 41814-78-2]; triforine, N,N'-{piperazine-1,4-diylbis[(trichloromethyl)methylene]}diformamide (DE-A 19 01 421); 5-chloro-7-(4-methylpiperidin-1-yl)-6-(2,4,6-trifluorophenyl)-[1,2,4] triazolo[1,5-a]pyrimidine (WO 98/46607) and other triazolo pyrimidine (EP-A 71 792; EP-A 141 317; WO 2003/009687; WO 2005/087771; WO 2005/087772; WO 2005/087773; WO 2006/087325; WO 2006/092428);

Bordeaux mixture, mixture of CuSO4×3Cu(OH)2×3CaSO4 [CAS RN 8011-63-0] copper acetate, Cu(OCOCHs)2 [CAS RN 8011-63-0]; copper oxychloride, Cu2Cl(OH)3 [CAS RN 1332-40-7]; basic copper sulfate, CuSO4 [CAS RN 1344-73-6]; binapacryl, (RS)-2-sec-butyl-4,6-dinitrophenyl 3-methylcrotonate [CAS RN 485-31-4]; dinocap, mixture of 2,6-dinitro-4-octylphenylcrotonate and 2,4-dinitro-6-octylphenylcrotonate, where "octyl" is a mixture of 1-methylheptyl, 1-ethylhexyl and 1-propylpentyl (U.S. Pat. No. 2,526,660); dinobuton, (RS)-2-sec-butyl-4,6-dinitrophenyl isopropyl carbonate [CAS RN 973-21-7]; nitrothal-isopropyl, diisopropyl 5-nitroisophthalate (Proc. Br. Insectic. Fungic. Conf. 7., Vol. 2, p. 673 (1973)); fenpiclonil, 4-(2,3-dichlorophenyl)-1H-pyrrole-3-carbonitrile (Proc. 1988 Br. Crop Prot. Conf.—Pests Dis., Vol. 1, p. 65); fludioxonil, 4-(2,2-difluorobenzo[1,3]dioxol-4-yl)-1H-pyrrole-3-carbonitrile (The Pesticide Manual, publ. The British Crop Protection Council, 10th ed. 1995, p. 482); acibenzolar-S-methyl, methyl 1,2,3-benzothiadiazole-7-carbothioate [CAS RN 135158-54-2]; flubenthiavalicarb (benthiavalicarb), isopropyl {(S)-1-[(1R)-1-(6-fluorobenzothiazol-2-yl)-ethylcarbamoyl]-2-methylpropyl}carbamate (JP-A 09/323 984); carpropamid, 2,2-dichloro-N-[1-(4-chlorophenyl)ethyl]-1-ethyl-3-methylcyclopropane-carboxamide [CAS RN 104030-54-8]; chlorothalonil, 2,4,5,6-tetrachloroisophthalonitrile (U.S. Pat. No. 3,290,353); cyflufenamid, (Z)-N-[α-(cyclopropylmethoxyimino)-2,3-difluoro-6-(trifluoromethyl)benzyl]-2-phenylacetamide (WO 96/19442); cymoxanil, 1-(2-cyano-2-methoxyiminoacetyl)-3-ethylurea (U.S. Pat. No. 3,957,847); diclomezine, 6-(3,5-dichlorophenyl-p-tolyl)pyridazin-3(2H)-one (U.S. Pat. No. 4,052,395) diclocymet, (RS)-2-cyano-N-[(R)-1-(2,4-dichlorophenyl)ethyl]-3,3-dimethylbutyramide [CAS RN 139920-32-4]; diethofencarb, isopropyl 3,4-diethoxycarbanilate (EP-A 78 663); edifenphos, O-ethyl S,S-diphenyl phosphorodithioate (DE-A 14 93 736) ethaboxam, N-(cyano-2-thienylmethyl)-4-ethyl-2-(ethylamino)-5-thiazolecarboxamide (EP-A 639 574); fenhexamid, N-(2,3-dichloro-4-hydroxyphenyl)-1-methylcyclohexanecarboxamide (Proc. Br. Crop Prot. Conf.—Pests Dis., 1998, Vol. 2, p. 327); fentin-acetate, triphenyltin (U.S. Pat. No. 3,499,086); fenoxanil, N-(1-cyano-1,2-dimethylpropyl)-2-(2,4-dichlorophenoxy)propanamide (EP-A 262 393); ferimzone, (Z)-2'-methylacetophenone-4,6-dimethylpyrimidin-2-ylhydrazone [CAS RN 89269-64-7]; fluazinam, 3-chloro-N-[3-chloro-2,6-dinitro-4-(trifluoromethyl)phenyl]-5-(trifluoromethyl)-2-pyridinamine (The Pesticide Manual, publ. The British Crop Protection Council, 10th ed. (1995), p. 474); fosetyl, fosetyl-aluminum, ethylphosphonate (FR 22 54 276); iprovalicarb, isopropyl [(1 S)-2-methyl-1-(1-p-tolylethylcarbamoyl)propyl]carbamate (EP-A 472 996); hexachlorobenzene (C. R. Seances Acad. Agric. Fr., Vol. 31, p. 24 (1945)); mandipropamid, (RS)-2-(4-chlorophenyl)-N-[3-methoxy-4-(prop-2-ynyloxy)phenethyl]-2-(prop-2-ynyloxy)acetamide (WO 03/042166); metrafenone, 3'-bromo-2,3,4,6'-tetramethoxy-2',6-dimethylbenzophenone (U.S. Pat. No. 5,945,567); pencycuron, 1-(4-chlorobenzyl)-1-cyclopentyl-3-phenylurea (DE-A 27 32 257); penthiopyrad, (RS)-N-[2-(1,3-dimethylbutyl)-3-thienyl]-1-methyl-3-(trifluoromethyl)-1H-pyrazole-4-carboxamide (JP 10/130268); propamocarb, isopropyl 3-(dimethylamino)propylcarbamate (DE-A 15 67 169); phthalide (DE-A 16 43 347); toloclofos-methyl, 0-2,6-dichloro-p-tolyl 0,0-dimethyl phosphorothioate (GB 14 67561); quintozene, pentachloronitrobenzene (DE-A 682 048); zoxamide, (RS)-3,5-dichloro-N-(3-chloro-1-ethyl-1-methyl-2-oxopropyl)-p-toluamide [CAS RN 156052-68-5]; captafol, N-(1,1,2,2-tetrachloroethylthio)cyclohex-4-ene-1,2-dicarboximide (Phytopathology, Vol. 52, p. 754 (1962)); captan, N-(trichloromethylthio)cyclohex-4-ene-1,2-dicarboximide (U.S. Pat. No. 2,553,770); dichlofluanid, N-dichlorofluoromethylthio-N,N-dimethyl-N-phenylsulfamide (DE-A 1 1 93 498); folpet, N-(trichloromethylthio)phthalimide (U.S. Pat. No. 2,553,770); tolylfluanid, N-dichlorofluoromethylthio-N,N-dimethyl-N-p-tolylsulfamide (DE-A 1 1 93 498); dimethomorph, 3-(4-chlorophenyl)-3-(3,4-dimethoxyphenyl)-1-morpholin-4-yl-propenone (EP-A 120 321); flumetover, 2-(3,4-dimethoxyphenyl)-N-ethyl-α,α,α-trifluoro-N-methyl-p-toluamide [AGROW no. 243, 22 (1995)]; flumorph, 3-(4-fluorophenyl)-3-(3,4-dimethoxyphenyl)-1-morpholin-4-ylpropenone (EP-A 860 438); N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide (WO 03/66610); N-(3',4'-dichloro-4-fluorobiphenyl-2-yl)-3-difluoromethyl-1-methylpyrazole-4-carboxamide and N-(3',4'-dichloro-5-fluorobiphenyl-2-yl)-3-difluoromethyl-1-methylpyrazole-4-carboxamide (WO 03/70705); N-(2-cyanophenyl)-3,4-dichloroisothiazole-5-carboxamide (WO 99/24413); N-(2-(4-[3-(4-chlorophenyl)prop-2-ynyloxy]-3-methoxyphenyl) ethyl)-2-methanesulfonylamino-3-methylbutyramide, N-(2-(4-[3-(4-chlorophenyl)prop-2-ynyloxy]-3-methoxyphenyl) ethyl)-2-ethanesulfonylamino-3-methylbutyramide (WO 04/49804); N-(2-Bicycloprop-2-ylphenyl)-3-difluoromethyl-1-methyl-1H-pyrazole-4-carboxamide is a mixture of the diastereomers N-(trans-2-bicycloprop-2-ylphenyl)-3-difluoromethyl-1-methyl-1H-pyrazole-4-carboxamide and N-(cis-2-bicycloprop-2-ylphenyl)-3-difluoromethyl-1-methyl-1H-pyrazole-4-carboxamide (WO 03/074491 and WO 2006/015866); 3-[5-(4-chlorophenyl)-2,3-dimethyl-isoxazolidin-3-yl]pyridine (EP-A 10 35 122); 2-butoxy-6-iodo-3-propylchromen-4-one (WO 03/14103); N,N-dimethyl-3-(3-bromo-6-fluoro-2-methylindole-1-sulfonyl)-[1,2,4]triazole-1-sulfonamide (EP-A 10 31 571); methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate (EP-A 12 01 648); methyl 3-(4-chlorophenyl)-3-(2-isopropoxycarbonylamino-3-methylbutyrylamino)propionate (EP-A 10 28 125); azoxystrobin, methyl 2-{2-[6-(2-cyano-1-vinylpenta-1,3-dienyloxy)pyrimidin-4-yloxy]phenyl}-3-methoxyacrylate (EP-A 382 375), dimoxystrobin, (E)-2-(methoxyimino)-N-methyl-2-[α-(2,5-xylyloxy)-o-tolyl]acetamide (EP-A 477 631); fluoxastrobin, (E)-{2-[6-(2-chlorophenoxy)-5-fluoropyrimidin-4-yloxy]phenyl}(5,6-dihydro-1,4,2-dioxazin-3-yl) methanone O-methyloxime (WO 97/27189); kresoxim-methyl, methyl (E)-methoxyimino[α-(o-tolyloxy)-o-tolyl] acetate (EP-A 253 213); metominostrobin, (E)-2-(methoxyimino)-N-methyl-2-(2-phenoxyphenyl)acetamide (EP-A 398 692); orysastrobin, (2E)-2-(methoxyimino)-2-{2-[(3E,5E,6E)-5-(methoxyimino)-4,6-dimethyl-2,8-dioxa-3,7-diazanona-3,6-dien-1-yl]phenyl}-N-methylacetamide (WO 97/15552); picoxystrobin, methyl 3-methoxy-2-[2-(6-trifluoromethylpyridin-2-yloxymethyl)phenyl]acrylate (EP-A 278 595); pyraclostrobin, methyl N-{2-[1-(4-chlorophenyl)-1H-pyrazol-3-yloxymethyl]phenyl}(N-methoxy) carbamate (WO 96/01256); trifloxystrobin, methyl (E)-methoxyimino-{(E)-α-[1-(α,α,α-trifluoro-m-tolyl) ethylideneaminooxy]-o-tolyl}acetate (EP-A 460 575); methyl 2-[ortho-(2,5-dimethylphenyloxymethylene)phenyl]-3-methoxyacrylate (EP-A226 917); 5-chloro-7-(4-methylpiperidin-1-yl)-6-(2,4,6-trifluorophenyl)-[1,2,4]triazolo[1,5-a]pyrimidine (WO 98/46608); 3,4-dichloro-N-(2-cyanophenyl)isothiazole-5-carboxamide (WO 99/24413), compounds of the formula III (WO 04/049804); N-(2-(4-[3-(4-chlorophenyl)prop-2-ynyloxy]-3-methoxyphenyl) ethyl)-2-methanesulfonylamino-3-methylbutyramide and N-(2-(4-[3-(4-chlorophenyl)prop-2-ynyloxy]-3-methoxyphenyl)ethyl)-2-ethanesulfonylamino-3-methylbutyramide (WO 03/66609); 2-butoxy-6-iodo-3-propylchromen-4-one (WO 03/14103); N,N-dimethyl-3-(3-bromo-6-fluoro-2-methylindole-1-sulfonyl)-[1,2,4]triazole-1-sulfonamide (WO 03/053145); methyl 3-(4-chlorophenyl)-3-(2-isopropoxycarbonylamino-3-methylbutyrylamino)-propanoate (EP-A 1028125).

The invention also contemplates a veterinary or pharmaceutical composition comprising a) fluralaner, b) a macrocyclic lactone or derivative thereof, and optionally, c) at least one additional veterinary agent.

The invention also contemplates a veterinary or pharmaceutical composition comprising a) fluralaner, b) a macrocyclic lactone or derivative thereof, and c) at least one additional veterinary agent.

The invention also contemplates a veterinary or pharmaceutical composition comprising a) fluralaner b) a macrocyclic lactone or derivative thereof, and optionally, c) at least one additional veterinary agent.

The invention also contemplates a veterinary or pharmaceutical composition comprising a) fluralaner, b) a macrocyclic lactone or derivative thereof, and c) at least one additional veterinary agent.

The invention also contemplates a veterinary or pharmaceutical composition comprising a) fluralaner, b) moxidectin, and optionally, c) at least one additional veterinary agent.

The invention also contemplates a veterinary or pharmaceutical composition comprising a) fluralaner, b) moxidectin, and c) at least one additional veterinary agent.

The invention also contemplates a veterinary or pharmaceutical composition comprising a) fluralaner, b) moxidectin, and c) pyrantel pamoate, oxantel, morantel, novaluron, imidacloprid, febantel, piperazine citrate, niclosamide, lufenuron, nitenpyram, oxibendazole, fenbendazole, fipronil, and amitraz, or any combination thereof.

The invention also contemplates a veterinary or pharmaceutical composition comprising a) fluralaner b) moxidectin, and c) pyrantel pamoate.

The invention also contemplates a veterinary or pharmaceutical composition comprising a) fluralaner, b) selamectin, and optionally, c) at least one additional veterinary agent.

The invention also contemplates a veterinary or pharmaceutical composition comprising a) fluralaner, b) milbemycin or milbemycin oxime, and optionally, c) at least one additional veterinary agent.

The invention also contemplates a veterinary or pharmaceutical composition comprising a) fluralaner, b) moxidectin, selamectin, milbemycin or milbemycin oxime, and optionally, c) praziquantel or epsiprantel.

The invention also contemplates a veterinary or pharmaceutical composition comprising effective amounts of fluralaner, macrocyclic lactone or derivative thereof, and least one additional veterinary agent.

The invention also contemplates a method of treating a parasitic infection or infestation in an animal, in need thereof, comprising administering a veterinary or pharmaceutical composition comprising a) fluralaner b) a macrocyclic lactone or derivative thereof, and optionally, c) at least one additional veterinary agent.

The invention also contemplates a method of treating a parasitic infection or infestation in an animal, in need thereof, comprising administering a veterinary or pharmaceutical composition comprising a) fluralaner, b) moxidectin, milbemycin, milbemycin oxime, or selamectin, and optionally, c) at least one additional veterinary agent.

The invention also contemplates a method of treating a parasitic infection or infestation in an animal, in need thereof, comprising administering a veterinary or pharmaceutical composition comprising a) fluralaner, b) moxidectin, milbemycin, milbemycin oxime, or selamectin, and c) at least one additional veterinary agent.

The invention also contemplates a veterinary or pharmaceutical composition comprising effective amounts of a) fluralaner, b) a macrocyclic lactone or derivative thereof, and optionally, c) at least one additional veterinary agent, as a medicament.

The invention also contemplates the use of the veterinary or pharmaceutical composition comprising a) fluralaner, b) a macrocyclic lactone or derivative thereof, and optionally, c) at least one additional veterinary agent, for the treatment of a parasitic infection or infestation in an animal, in need thereof, by administering an effective amount of each active agent to an animal in need thereof.

In another aspect of the invention, the macrocyclic lactone, or derivative thereof, is selected from the group consisting of: ivermectin, emamectin, selamectin, doramectin, moxidectin, abamectin, eprinomectin, milbemycin, and milbemycine oxime.

In another aspect of the invention, the additional veterinary agent is selected from the group consisting of: monepantel, tetrahydropyrimidines (e.g., pyrantel (pamoate, embonate, citrate, and tartrate salts), oxantel, morantel, and the like), febantel, piperazine citrate, niclosamide, fenbendazole, oxibendazole, mebendazole, flubendazole, dichlorvos, imidacloprid, an insect growth regulator (e.g., s-methoprene, hydroprene, praziquantel, epsiprantel, azadirachtin, diofenolan, fenoxycarb, kinoprene, and the like), chitin synthesis inhibitors (e.g., chlorfluazuron, cryomazine, diflubenzuron, fluazuron, flucycloxuron, flufenoxuron, hexaflumuron, lufenuron, tebufonozide, novaluron, teflubenzuron, triflumuron, and the like), and nitenpyram.

For the additional veterinary agents, for example, pyrantel, fenbendazole, ivermectin, selamectin, moxidectin, milbemycin oxime, oxantel, imidacloprid, and the like, dose ranges will generally range in accordance with approved product labels. For example, a dose range of about 0.5 to 10 μg/kg for moxidectin is contemplated. More preferred, a moxidectin dose range of about 1 to 5 g/kg, and more preferably, about 3 μg/kg is contemplated. An approved dose of milbemycin oxime (0.5 to 2 mg/kg), (0.6 Mg/kg), and selamectin (6 mg/kg), is contemplated; in another instance, a dose range of about 1 to 15 mg/kg is contemplated for pyrantel. More preferred, a pyrantel dose of about 2 to 10 mg/kg, or more preferably 5 mg/kg is contemplated. Further, approved doses for the additional veterinary agent(s) include, for example, imidacloprid (10 mg/kg), febantel (15 mg/kg), praziquantel (3.5 to 12 mg/kg), oxantel (20 mg/kg), piperazine citrate (200 mg/kg), and lufenuron (10 mg/kg), are contemplated.

In an embodiment, the invention comprises administering one or more other active ingredient such as a pyrethroid insecticide, a neonicotinoid, an insecticide repellent.

Pyrethroid insecticide are for example flumethrin, Bifenthrin, Cyfluthrins, Cypermethrin, Cyphenothrin, deltamethrin, d-phenothrin, Esfenvalerate, Etofenprox, Fenpropathrin, Gamma-cyhalothrin, Imiprothrin, Lambda-cyhalothrin, Momfluorothrin, Prallethrin, Permethrin, pyrethrins, Taufluvalinate, Tefluthrin, Tetramethrin.

Neonicotinoids are for example imidacloprid, acetamiprid, clothianidin, dinotefuran, nitenpyram, thiacloprid, thiamethoxam.

In a particular embodiment, the isoxazoline is combined with a pyrethroid instecticide, and a neonicotinoid, in particular, with citridiol and flumethrin.

5.4 Other Embodiments

The invention also contemplates a veterinary or pharmaceutical composition comprising effective amounts of a) fluralaner and b) any additional active agent or combination of active agents disclosed in any of the following documents: WO10003923-WO10003877-WO2013119442-EP2892347-U.S. Pat. No. 9,233,100-U.S. Pat. No. 9,259,417-US2016143285-US2016374994-EP2811998A-EP3061454A.

6 Fluralaner Smart Devices and Methods

The description of the concepts in this section "Fluralaner smart devices and methods" constitutes a description of each of these concepts in combination with each of the concepts disclosed in the other four sections and in particular in combination with the concepts "Fluralaner low dose" disclosed in section 1 hereabove.

In particular, each "smart devices and methods" concept can be combined with a "new galenic" concept, and/or a "new posology" concept, and/or a new therapeutic indication" concept, and/or a "new combinations" concept. Each "low dose" concept is particularly appropriate to be implemented in association with a "new posology" concept, and such association is particularly appropriate to be implemented with a "new galenic" concept, and in a "new therapeutic indication" (each of these indications being with or without the "new galenic" concept and/or with or without a "new combination" concept).

6.1 Important Features

From the known dosage of 25 mg/kg bodyweight/3 months of sustained efficacy (Bravecto), a 1-month dosage is supposed to be 25/3=around 8 mg/kg/month. However, the invention establishes that a dosage as low as 1 or 2 or 3 or 4 mg/kg/month would be sufficient to obtain the desired effect at least in some embodiments. This represents a decrease in dosage of 2 or of more than 2 times. This is particularly interesting fluralaner is not degraded in stools and can pollute the environment. Moreover, adverse effects with fluralaner have been reported and a decrease in dosage enables to limit those undesirable effects. Therefore applying the exact needed dosage to an animal is extremely beneficial, also because of the cost of the active ingredient and the economic advantage produced by an adjustment of the really effective dose.

Target dosage in a particular embodiment: about 35 g/kg/day×90 days: which means 8 times less product than the currently marketed fluralaner product (Bravecto).

The target dosage (expressed in μg of active ingredient/kg of animal bodyweight/day of administration of the active ingredient to the animal) may vary according to the targeted pest and its susceptibility to the active ingredient. Therefore, the target dosage may vary between about 5 μg/kg/day to about 200 g/kg/day. In another embodiment, the target dosage may vary between about 10 μg/kg/day to about 100 g/kg/day or between about 20 μg/kg/day to about 50 μg/kg/day.

Fluralaner may be administered as a regular and/or continuous sustained release for a determined period of time in order to maintain the effective amount of the active ingredient in the body.

Smart dosage forms may contain from about 0.5 mg to about 5 g of an active agent. In one embodiment of the dosage form, the dosage is from about 1 mg to about 500 mg of an active agent. More typically the dosage is about 1 mg to about 25 mg, 1 mg to about 50 mg, 10 mg to 10 about 100 mg, or 20 mg to about 200 mg. In other embodiments, the dosage is about 50 mg to about 300 mg, 50 mg to about 400 mg, 50 mg to about 500 mg, 50 mg to about 600 mg, 50 mg to about 800 mg, or 100 mg to about 1000 mg. In one embodiment of the invention, the active agent is present in the formulation at a concentration of about 0.05% to about 50% weight/volume. In other embodiments, the active agent may be present in the formulation at a concentration of about 0.1% to about 30%, about 0.5% to about 20% (w/v) or about 1% to about 10% (w/v). In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume. In a particular advantageous embodiment of the invention, the daily dose of the compounds is about 0.01 mg/kg to about 0.10 mg/kg of weight of animal. In another embodiment, the dose is about 0.02 mg/kg to about 0.08 mg/kg of weight of animal. In other embodiments, the dose of the inventive compounds is about 0.02 mg/kg to about 0.05 mg/kg, about 0.025 mg/kg to about 0.050 mg/kg or about 0.03 mg/kg to about 0.04 mg/kg. In other preferred embodiments, the dose is about 0.031 mg/kg to about 0.039 mg/kg, 0.032 mg/kg to about 0.038 mg/kg or 0.033 mg/kg to about 0.037 mg/kg. More typically, in some embodiments the dose of the active compounds is about 0.034 mg/kg to about 0.036 mg/kg. In still other embodiments of the invention, the dose received daily (on average, meaning that the dose may be administered repeatedly at intervals greater than a day but at the end the dose is divided by the number of day without administration) by the animal may be as low as about 0.035 mg/kg. With a device adapted for releasing such a dose daily or at greater intervals, the total amount of active received after 3 months does not exceed 3.15 mg/kg (which is highly desirable compared to the current amount dispensed by Bravecto for the same period of time that is 25 mg/kg).

In particular, doses can be administered topically, such as collar, tag, impregnated device such as an impregnated toy, patch, spot-on, pour-on, matrix, such as a matrix with controlled diffusion kinetics.

A smart device or intelligent device is a device that releases a low dose of fluralaner in accordance with the invention, wherein the dose is controlled by an action on the device or remotely on a remote controller that interacts with the device. The remote controller can be a computer, a phone or a smartphone, for example. Interaction is via telephone lines, data channels, and/or magnetic or electromagnetic signals.

The dose releases can be controlled automatically via a remote circuit that includes sensor(s) and/or camera(s) for detection of parameters that trigger a release, or a modification of a release schedule, for example. Alternatively, or in addition, the sensor(s) and/or camera(s) can alert or inform the pet owner of the need to start, stop, or modify a release schedule, or an individual release.

The smart device or intelligent device can be a collar, or another device secured or implanted on or in the animal, such as a patch, implant, matrix, etc., or any other device equipped with a remote control circuit and antenna adapted for remote control by a user. The release is preferentially topical, but the release can also be parenteral, intravenous, oral, buccal and/or nasal.

Documents WO2016001216A1, WO12107585 A1, WO11120427 A1, U.S. Pat. Nos. 7,140,325 BB, 6,010,492 A, US2010137451 AA, JP2002193755 A2, U.S. Pat. Nos. 10,032,123, 5,980,496 A disclose devices and methods that fit for such an invention, but are of course not limitative.

In the present specification, the description or mention of a collar describes a smart or intelligent collar, and also describes a smart device or intelligent other than a collar that is adapted to be used to release controlled low doses in accordance with this section “smart devices and methods”. Conversely, the description or mention of a smart device or smart method describes, inter alia a collar in and as the device and the use of a collar in and for the method. When appropriate the description or mention of a collar also describes a conventional collar adapted to carry, store and/or dispense at least one dose of a topical composition, preferentially a plurality of doses.

6.2 Definitions

Reduced dosage: in the framework of the invention, «reduced dosage» refers to a dosage that is decreased regarding usual recommendation (ie 25 mg/kg/3 months for a dog in Bravecto®). In some embodiments, this reduced dosage corresponds to 1/50, 1/10, 1/8, 1/7, 1/5, 1/4, 1/3, 3/8, 1/2 times the regular dosage for a given period of time.

For instance, with Bravecto, a 25 mg/kg dosage is recommended for a dog over a period of 3 months. A reduced dosage thus corresponds for example to less than 12.5, 9.37, 8.33, 5, 3.5, 3.15, 3, 2.5, 0.5 mg/kg for a period of 3 months, in a single or as multiple administrations.

For a dog receiving fluralaner, this reduced dosage is comprised for example between around 0.5 and around 12.5 mg/kg, preferably between around 2.5 and around 10 mg/kg preferably between around 5 and around 10 mg/kg, preferably between around 7 and around 10 mg/kg.

Around: in the framework of the invention, around refers to a value that is more or less 1%, 2%, 3%, 4%, 5%, 10%, 15%, 20%, 25%, 30% of the target value. For instance, a dosage of around 5 mg/kg refers to a dosage of 5 mg, but also to a dosage comprised between 4.75 and 5.25 mg/kg to dosage comprised between 3.5 to 6.5 mg/kg.

About: in the framework of the invention, about also refers to a value that is more or less 1%, 2%, 3%, 4%, 5%, 10%, 15%, 20%, 25%, 30% of the target value. For instance, a dosage of about 5 mg/kg refers to a dosage of 5 mg, but also to a dosage comprised between 4.75 and 5.25 mg/kg to dosage comprised between 3.5 to 6.5 mg/kg.

In an embodiment, the dosage of 12.5 mg/kg for administration of fluralaner to a dog is specifically excluded.

By “effective amount” or “efficient amount” or “effective dose” is intended a sufficient amount of a composition of the invention to eradicate or reduce the number of parasites infesting the animal. In one embodiment, an effective amount of the active agent achieves at least 70% efficacy against the target parasite compared to a negative control according to known methods used in the art (animal not treated or treated with a placebo). In other embodiments, an effective amount of the active agent achieves at least 80%, or at least 90% efficacy against the target pests. Preferably, an effective amount of the active agent will achieve at least 95% efficacy against the target pests. In some embodiments, an effective amount of the compounds and compositions of the invention achieve at least 98% or 100% efficacy against the target parasites.

6.3 Embodiments

In an embodiment, the device further administers one or more other active ingredient such as a pyrethroid insecticide, a neonicotinoid, an insecticide repellent.

Pyrethroid insecticide are for example flumethrin, Bifenthrin, Cyfluthrins, Cypermethrin, Cyphenothrin, deltamethrin, d-phenothrin, Esfenvalerate, Etofenprox, Fenpropathrin, Gamma-cyhalothrin, Imiprothrin, Lambda-cyhalothrin, Momfluorothrin, Prallethrin, Permethrin, pyrethrins, Tau-fluvalinate, Tefluthrin, Tetramethrin.

Neonicotinoids are for example imidacloprid, acetamiprid, clothianidin, dinotefuran, nitenpyram, thiacloprid, thiamethoxam.

In a particular embodiment, the isoxazoline is combined with a pyrethroid instecticide, and a neonicotinoid, in particular, with citridiol and flumethrin.

BRIEF DESCRIPTION OF THE DRAWINGS

The following detailed description of particular, non-limitative embodiments is given in reference to the appended drawings in which.

Measured Cmax is about 5.9 times what would have been expected.

2. Fleas efficacy: comparison between experimental data and literature data

Figure 8:
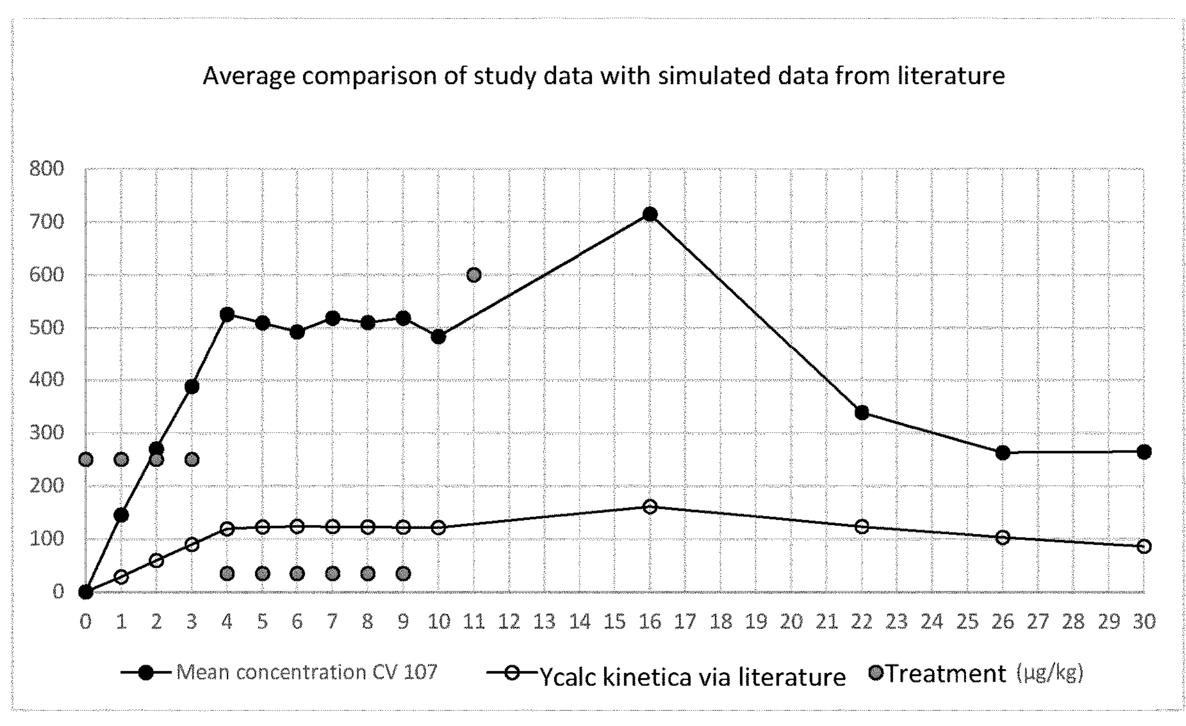

FIG. 8 shows the mean plasma concentration as a function of days, in the treatment study and in simulated data from literature.

Figure 9:
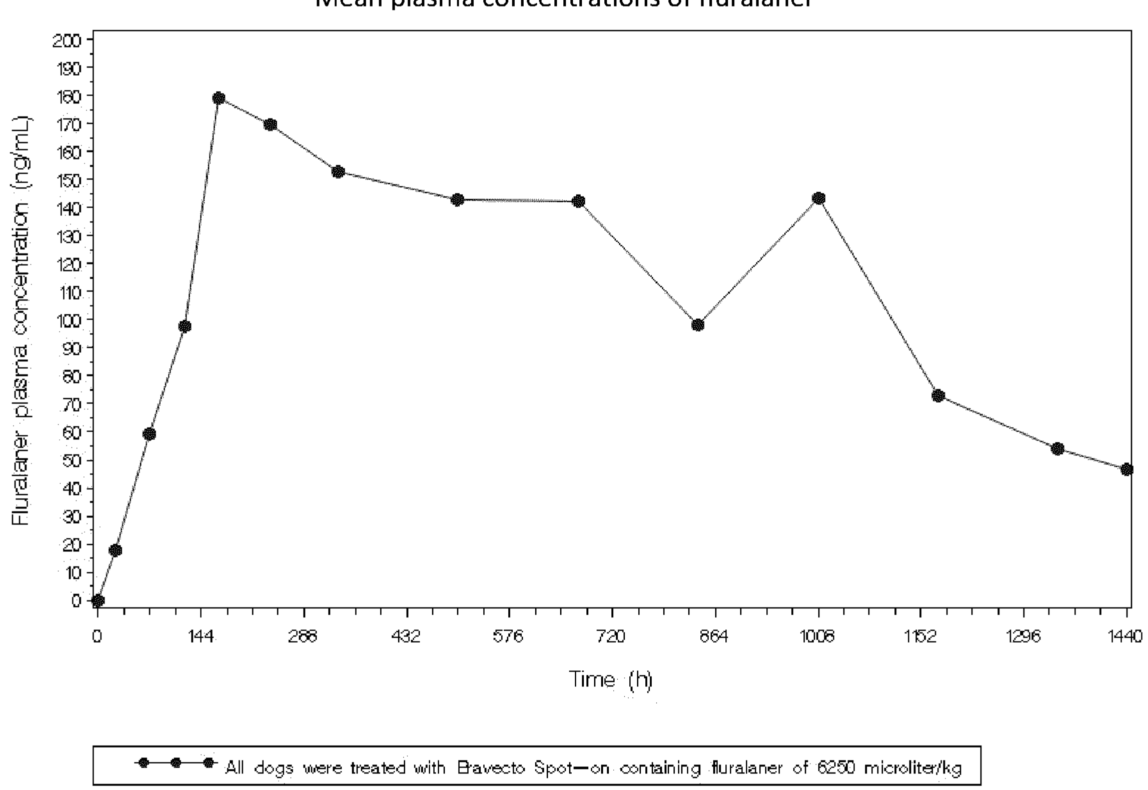

FIG. 9 shows the mean fluralaner plasma concentrations as a function of time, in an experiment of topical administration.

EXAMPLES

1. Oral Administration Against Fleas

Fleas Efficacy

Protocol

The first objective of the study was to obtain the pharmacokinetic parameters after repeated oral administration of 35 μg/kg of fluralaner in dogs, 30 to 35 minutes after feeding.

The second objective was to investigate the pharmacodynamics between the fluralaner plasmatic dose and the effectiveness against fleas.

IVP: Investigational Veterinary Product, is pure Fluralaner+DMSO (35 μg/kg on Days 0 to 3 (0.35 mL/kg))

Control product is DMSO (0.35 mL/kg on Days 0 to 3)

Twelve beagle dogs aged more than 6 months old, in the same age group, weighing ≥10 kg to ≤15 kg) were enrolled in the study of which nine were included and randomly allocated to two groups (1 and 2) based on total live flea counts, obtained one day after the initial infestation. In addition, clinical examinations on Days −7 and −1, daily general health observations, hair length measurement (Day −1) and body weights (Day −1) were performed.

On Days 0, 1, 2 and 3, all dogs assigned to group 2 received the Investigational Veterinary Product. On Days 0 to 3 all dogs in group 1 received the control product at a volume equal to the dogs in group 2. Dogs assigned to group 1 received the control product and served as Placebo controls. The quantity of Investigational Veterinary Product and control product administered was calculated according to the dog's individual body weight measured on Day −1.

Dogs were infested with approximately 100 (±8) viable, adult, *C. felis* fleas on Day −6 for randomisation purposes and on Days 1, 2 and 3 to assess efficacy. Fleas were removed and counted on Days −5, 2, 3 and 4 (24 hours±2 hours after infestation). Dogs were also infested with approximately 50 (±4) viable, adult, unfed *R. sanguineus* ticks on Day 4 to assess acaricidal efficacy. Ticks will be removed and counted on Day 5 (24 hours±2 hours after infestation).

Blood samples were taken from all dogs prior to Investigational Veterinary Product treatment or control product administration on Day 0 and on Days 1 (+24 hours), 2 (+48 hours), 3 (+72 hours), 4 (+96 hours), 5 (+120 hours), 10 (+240 hours), 15 (+360 hours), 20 (+480 hours), 24 (+576 hours) and Day 28 (+672 hours).

The two dogs with the lowest pre-Investigational Veterinary Product flea counts, as well as one dog with pre-Investigational Veterinary Product body weight that was too low, were not included. The study population thus consisted of three dogs in the control group 1 and six dogs in Investigational Veterinary Product group 2. Group 1 contained two females and one male and group 2 contained three females and three males.

Dogs were observed hourly±15 minutes for four hours after administration on Day 0 and once daily two hours±15 minutes after Investigational Veterinary Product or control product administration on Days 1, 2 and 3. Observations were conducted for each individual dog.

On days of administration of pre-Investigational Veterinary Product or Control Product, dogs were fed (the same dog food) approximately half of their normal daily ration 30 minutes to 35 minutes prior to administration. Food consumed by the time of administration was calculated and recorded. The remainder of their normal daily ration was fed immediately after administration.

Results

No Adverse Events as a result of the Investigational Veterinary Product were recorded.

The mean terminal half-life of fluralaner was 217.4 h (range: 155.2 h to 261.4 h).

The mean maximum concentration (Cmax) of fluralaner was 84.38 ng/mL (range: 71.8 ng/mL to 92.4 ng/mL), and was observed in all six animals 24 h after the fourth and last dose application of 35 μg/kg per day.

Steady state concentrations of fluralaner were not reached after the fourth dose, which is not surprising given the terminal half-life of approximately 217 h.

Figure 1:
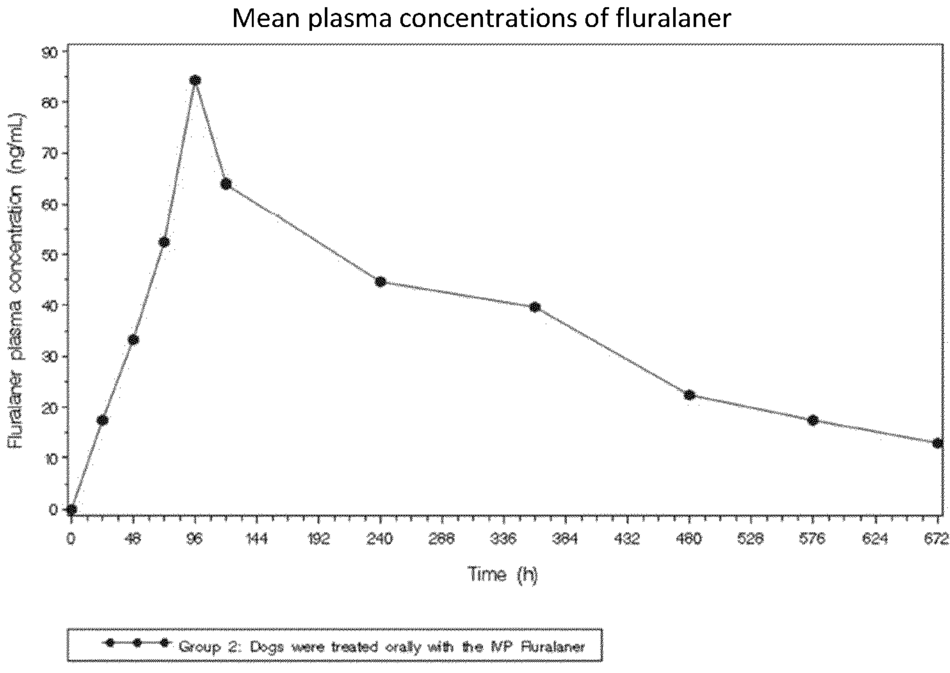
FIG. 1 shows the mean fluralaner plasma concentrations over time in dogs treated orally with the IVP furalaner, in an experiment of oral administration against fleas.

FIG. 1 shows the mean fluralaner plasma concentrations over time in dogs treated orally with the IVP furalaner.

The efficacy of fluralaner against fleas was 100% for the period from Day 2 to Day 4, 24 hours after infestation.

More specifically, the efficacy was 99.6% at 24 h after the first two doses of fluralaner at 35 μg/kg per day, 100% at 24 h after the first three doses, and 99.8% after the fourth and final dose.

The efficacy of fluralaner against ticks was 40.4% which was observed 48 h after the last of the four doses of fluralaner at 35 μg/kg per day.

Figure 2:
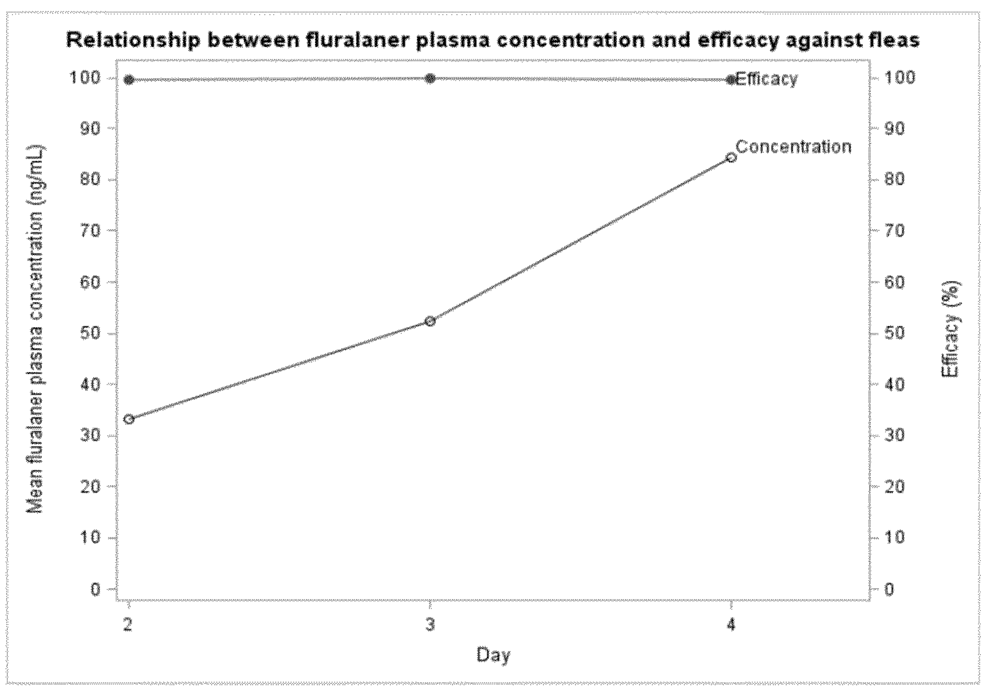
FIG. 2 shows the mean fluralaner plasma concentrations and efficacy values over time, in the same experiment of oral administration against fleas.

FIG. 2 shows the mean fluralaner plasma concentrations and efficacy values over time. The graph underlines the efficacy at the very first doses.

The results for the individual animals of the group study are shown below.

TABLE 1 individual and summary statistics of fluralaner concentration levels (ng/mL)—Group 2

| Animal ID | Time (h) | | | | | | | | | | |
|---|---|---|---|---|---|---|---|---|---|---|---|
| Statistic | 0 | 24 | 48 | 72 | 96 | 120 | 240 | 360 | 480 | 576 | 672 |
| 83F 29E | 0.0 | 16.9 | 32.2 | 47.9 | 91.6 | 63.6 | 34.1 | 39.6 | 17.1 | 14.7 | 9.1 |
| 86A 6A7 | 0.0 | 18.1 | 37.2 | 61.0 | 84.5 | 55.6 | 36.3 | 43.5 | 21.1 | 15.0 | 10.3 |
| ABC D95 | 0.0 | 16.9 | 35.2 | 42.0 | 71.8 | 62.9 | 51.6 | 37.4 | 26.6 | 22.2 | 16.0 |
| AC3 365 | 0.0 | 19.0 | 40.9 | 57.7 | 92.4 | 70.0 | 44.4 | 35.2 | 18.4 | 13.3 | 10.4 |
| AC4 A83 | 0.0 | 16.7 | 26.1 | 44.6 | 89.4 | 72.3 | 54.9 | 42.8 | 25.3 | 17.3 | 16.0 |
| AC7 314 | 0.0 | 16.5 | 27.8 | 60.6 | 76.6 | 60.1 | 45.8 | 39.2 | 26.1 | 22.0 | 15.1 |
| n | 6 | 6 | 6 | 6 | 6 | 6 | 6 | 6 | 6 | 6 | 6 |
| Mean | 0.00 | 17.35 | 33.23 | 52.30 | 84.38 | 64.08 | 44.52 | 39.62 | 22.43 | 17.42 | 12.82 |
| SD | 0.000 | 0.983 | 5.654 | 8.467 | 8.491 | 6.197 | 8.194 | 3.156 | 4.136 | 3.849 | 3.206 |
| Std Err | 0.000 | 0.400 | 2.310 | 3.460 | 3.470 | 2.530 | 3.340 | 1.290 | 1.690 | 1.570 | 1.310 |
| CV % | | 5.7 | 17.0 | 16.2 | 10.1 | 9.7 | 18.4 | 8.0 | 18.4 | 22.1 | 25.0 |
| GeoMean | | 17.33 | 32.83 | 51.72 | 84.01 | 63.83 | 43.87 | 39.51 | 22.10 | 17.07 | 12.48 |
| Median | 0.00 | 16.90 | 33.70 | 52.80 | 86.95 | 63.25 | 45.10 | 39.40 | 23.20 | 16.15 | 12.75 |
| Minimum | 0.0 | 18.5 | 26.1 | 42.0 | 71.8 | 55.6 | 34.1 | 35.2 | 17.1 | 13.3 | 9.1 |
| Maximum | 0.0 | 19.0 | 40.9 | 61.0 | 92.4 | 72.3 | 54.9 | 43.5 | 26.6 | 22.2 | 16.0 |

LOQ: 1.00 ng/mL
Group 2: Dogs were treated orally with the IVP Fluralaner

TABLE 2 individual and summary statistics of fluralaner PK parameters—Group 2
Table 11: Individual and summary statistics of fluralaner PK parameters—Group 2

| Animal ID Statistic | Cmax (ng/mL) | Tmax (h) | Lambda z | t½ (h) | AUC 0-t (ng · h/mL) | AUC 0-inf (ng · h/mL) | AUC extrap (%) |
|---|---|---|---|---|---|---|---|
| 83F 29E | 91.6 | 96 | 0.0045 | 155.2 | 21644 | 23684 | 8.6 |
| 86A 6A7 | 84.5 | 96 | 0.0037 | 185.6 | 22612 | 25369 | 10.9 |
| ABC D95 | 71.8 | 96 | 0.0027 | 261.4 | 24960 | 30994 | 19.5 |
| AC3 365 | 92.4 | 96 | 0.0030 | 233.3 | 23395 | 26895 | 13.0 |
| AC4 A83 | 89.4 | 96 | 0.0030 | 233.6 | 26334 | 31726 | 17.0 |
| AC7 314 | 76.6 | 96 | 0.0029 | 235.6 | 24538 | 29670 | 17.3 |
| n | 6 | 6 | 6 | 6 | 6 | 6 | 6 |
| Mean | 84.38 | 96.0 | 0.00329 | 217.43 | 23913.9 | 28056.4 | 14.38 |
| SD | 8.491 | 0.00 | 0.000681 | 39.158 | 1700.45 | 3237.11 | 4.212 |
| Std Err | 3.470 | 0.00 | 0.000280 | 15.990 | 694.20 | 1321.50 | 1.720 |
| CV % | 10.1 | 0.0 | 20.7 | 18.0 | 7.1 | 11.5 | 29.3 |
| GeoMean | 84.01 | 96.0 | 0.00324 | 214.21 | 23863.6 | 27898.1 | 13.82 |
| Median | 86.95 | 96.0 | 0.00297 | 233.43 | 23966.8 | 28282.4 | 15.00 |
| Minimum | 71.8 | 96 | 0.0027 | 155.2 | 21644 | 23684 | 8.6 |
| Maximum | 92.4 | 96 | 0.0045 | 261.4 | 26334 | 31726 | 19.5 |

Group 2: Dogs were treated orally with the IVP Fluralaner

In conclusion, a high efficacy is obtained against fleas whatever the dose, from 24 hours after administration (infestation at D1, first measurement at D2). Bioavailability is about 5 times higher than expected.

Discussion and Conclusion

The mean terminal half-life of fluralaner was 217.4 h (range: 155.2 h to 261.4 h).

The mean maximum concentration (Cmax) of fluralaner was 84.38 ng/mL (range: 71.8 ng/mL to 92.4 ng/mL), and was observed, as expected, in all six animals 24 h after the fourth and last dose application of 35 µg/kg per day.

Steady state concentrations of fluralaner were not reached after the fourth dose, which is not surprising given the terminal half-life of approximately 217 h.

The efficacy of fluralaner against ticks was 40.4% which was observed 48 h after the last of the four doses of fluralaner at 35 µg/kg per day.

The efficacy of fluralaner against fleas was virtually 100% for the period from Day 2 to Day 4.

More specifically, the efficacy was 99.6% at 24 h after the first two doses of fluralaner at 35 µg/kg per day, 100% at 24 h after the first three doses, and 99.8% after the fourth and final dose.

General Conclusion

Both oral studies provide significantly improved bioavailability of the active substance fluralaner compared to the literature data available.

Both oral studies provide unexpectedly significant improvement in bioavailability, enabling a significantly lower dosage required to achieve superior pharmacokinetic profiles and attain efficacy against ticks and fleas. Bioavailability is about 5 times higher than expected.

2. Oral Administration Against Ticks

Ticks Efficacy

Protocol

The first objective is to obtain the pharmacokinetic parameters after repeated oral administration of 250 jg/kg and 35 µg/kg of fluralaner in dogs after feeding.

The second objective is to investigate the pharmacodynamics between the fluralaner plasmatic dose and the effectiveness against ticks.

IVP: Investigational Veterinary Product, is pure Fluralaner+DMSO (250 μg/kg on Days 0 to 3 (0.25 mL/kg), then 35 μg/kg on Days 4 to 9 (0.35 mL/kg), then 600 μg/kg on Day 11)

Control product is DMSO (0.25 mL/kg on Days 0 to 3, then 0.35 mL/kg on Days 4 to 9)

Twelve beagle dogs (aged more than 6 months old, in the same age group, weighing ≥10 kg to ≤15 kg) were enrolled in the study of which nine were included and randomly allocated to two groups (1 and 2) based on total live flea counts, obtained one day after the initial infestation. In addition, clinical examinations on Days −7 and −1, daily general health observations, hair length measurement (Day −1) and body weights (Day −1) were performed.

On Days 0, 1, 2 and 3, all dogs assigned to group 2 received the Investigational Veterinary Product. On Days 0 to 3 all dogs in group 1 received the control product at a volume equal to the dogs in group 2. Dogs assigned to group 1 received the control product and served as Placebo controls. The quantity of Investigational Veterinary Product and control product administered was calculated according to the dog's individual body weight measured on Day −1.

Dogs were infested with approximately 50 (±4) viable, adult, unfed *R. sanguineus* ticks on Days 1, 3, 5, 8, 10, 12, 16, 22, 26 and 30 to assess efficacy. Ticks will be removed and counted on Days 3, 5, 7 (48 hours±2 hours after infestation) and 9, 11, 13, 17, 24, 27, 32 (24 hours±2 hours after infestation). Dogs were also infested with approximately 100 (±8) viable, adult, *C. felis* fleas on Day −6 (±1 day) for randomisation purposes and on Day 2 to assess efficacy. Fleas will be removed and counted on Days −5 (+1 day) and 3 (24 hours±2 hours after infestation).

Blood samples were taken from all dogs prior to Investigational Veterinary Product treatment on Day 0 and on Days 1 (+24 hours), 2 (+48 hours), 3 (+72 hours), 4 (+96 hours), 5 (+120 hours), 10 (+240 hours), 15 (+360 hours), 20 (+480 hours), 24 (+576 hours) and Day 28 (+672 hours).

The two dogs with the lowest pre-Investigational Veterinary Product flea counts, as well as one dog with pre-Investigational Veterinary Product body weight that was too low, were not included. The study population thus consisted of three dogs in the control group 1 and six dogs in Investigational Veterinary Product group 2. Group 1 contained two females and one male and group 2 contained three females and three males.

Dogs assigned to group 1 received the control product and served as Placebo controls. Dogs were observed hourly±15 minutes for four hours after administration on Day 0 and once daily two hours±15 minutes after Investigational Veterinary Product or control product administration on Days 1, 2 and 3. Observations were conducted for each individual dog.

On days of administration of pre-Investigational Veterinary Product or Control Product, dogs were fed (the same dog food) approximately half of their normal daily ration 30 minutes to 35 minutes prior to administration. Food consumed by the time of administration was calculated and recorded. The remainder of their normal daily ration was fed immediately after administration.

Results

No Adverse Events as a result of the Investigational Veterinary Product were recorded.

The mean terminal half-life of fluralaner was 372.42 h (range: 227.3 h to 494.6 h).

The mean for Cmax of fluralaner was 733.3 ng/mL (range: 561 ng/mL to 1000 ng/mL).

Steady state concentrations were reached with the 35 μg/kg dose per day application from Day 4 to Day 9.

Figure 3:
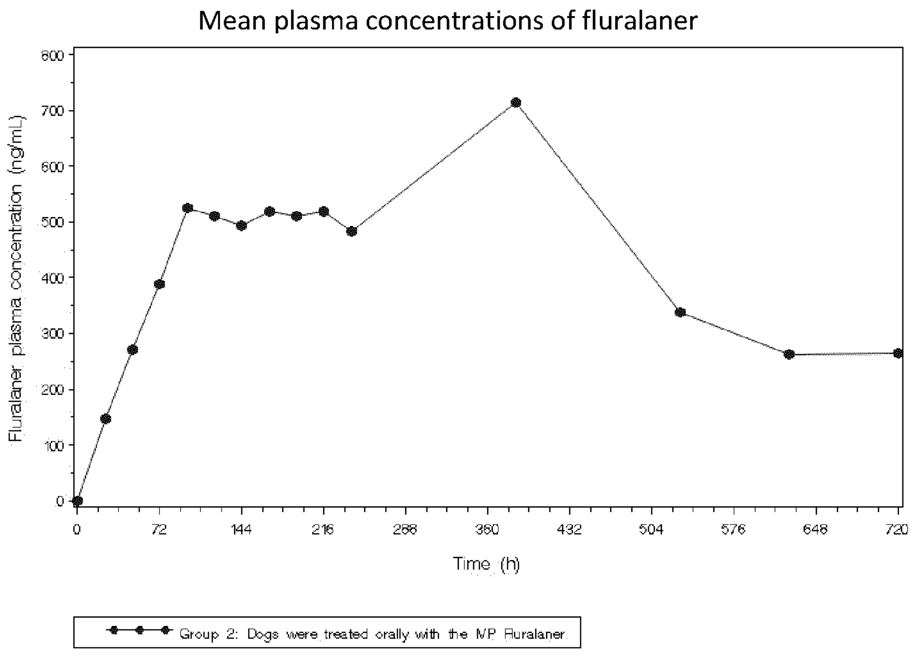
FIG. 3 shows the mean fluralaner plasma concentrations over time in dogs treated orally with the IVP furalaner, in an experiment of oral administration against ticks.

FIG. 3 shows the mean fluralaner plasma concentrations over time in dogs treated orally with the IVP furalaner.

The efficacy of fluralaner against ticks was 100% for the period during the first four doses of 250 μg/kg per day of fluralaner and the following three doses of 35 μg/kg per day. The efficacy decreased to approximately between 50% to 75% from Day 9 to Day 27 after the remaining consecutive doses of 35 μg/kg per day and the following single dose of 600 μg/kg on Day 11.

The efficacy of fluralaner against fleas was 92% on Day 3 (thus following 3 consecutive doses of 250 μg/kg per day of fluralaner.

Figure 4:
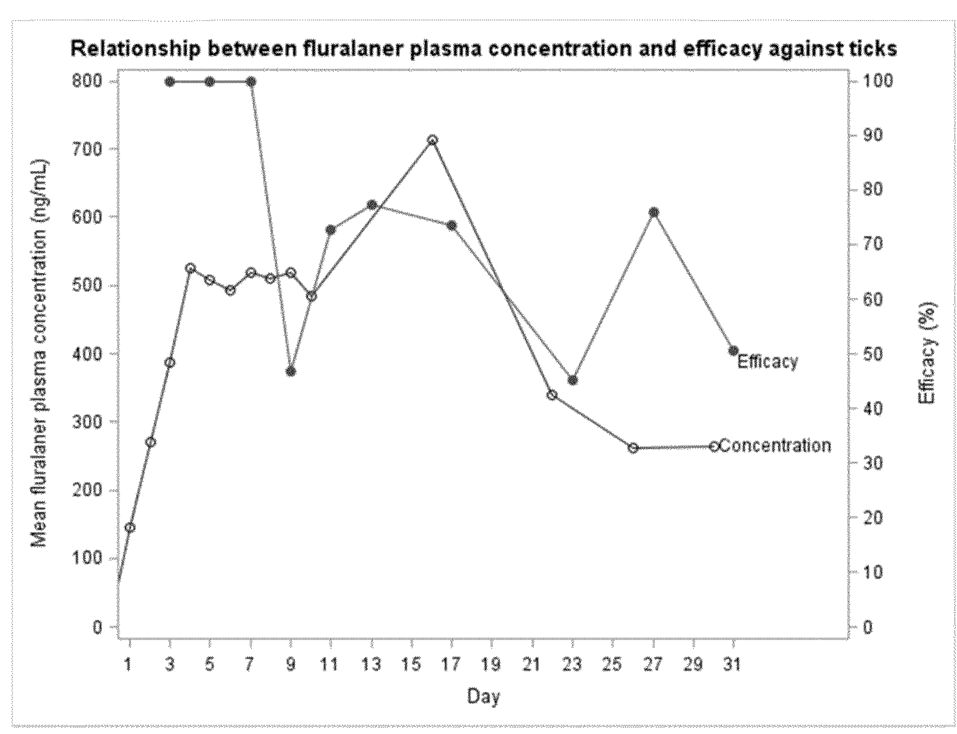
FIG. 4 shows the relationship between fluralaner plasma concentration and efficacy against ticks over time, in the same experiment of oral administration against ticks.

FIG. 4 shows the relationship between fluralaner plasma concentration and efficacy against ticks over time.

The efficacy value at day 9 can be explained by the change of the method of counting ticks. From day 0 to day 8, the count was every 48 hours (days 3, 5, 7). After day 8, it was every 24 hours.

The efficacy values at day 23 and day 31 are unexplained.

The plasmatic concentration at day 16 is also unexplained. It is believed to result from a manipulation or measurement error.

Figure 5:
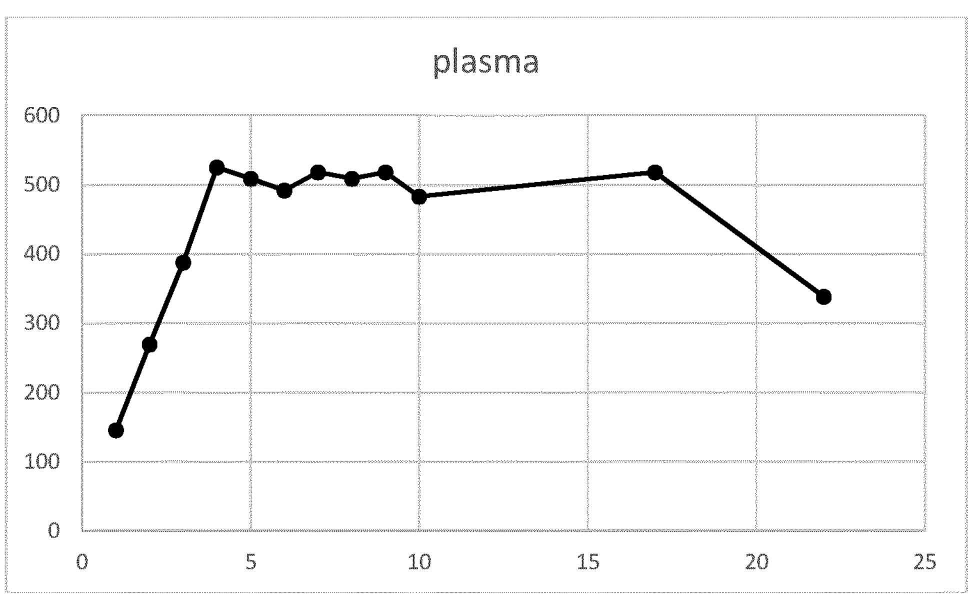
FIGS. 5 and 6 are smoothed graphs corresponding to FIG. 4, showing the fluralaner plasma concentration and efficacy, respectively.
Figure 6:
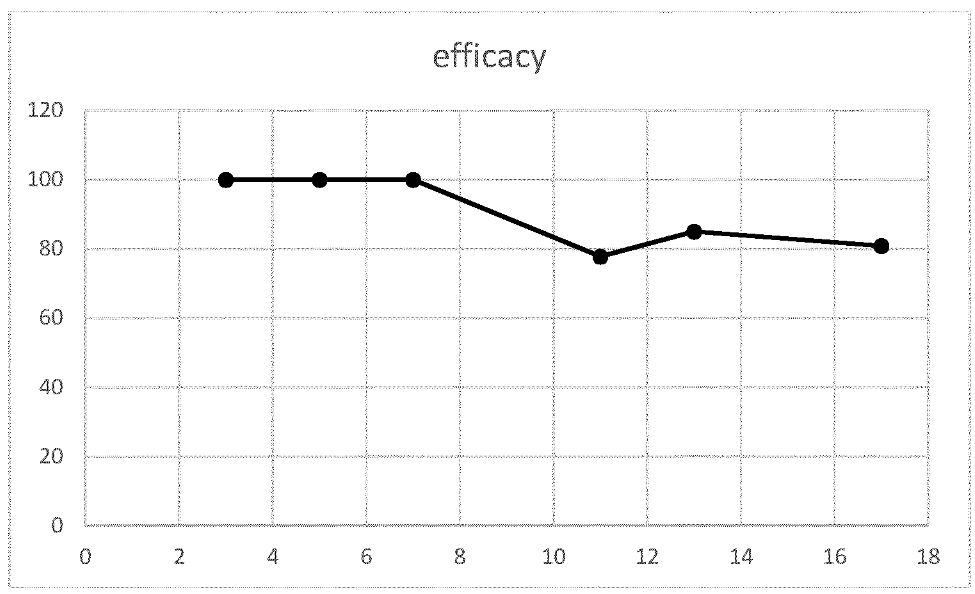

FIGS. 5 and 6 are smoothed graphs corresponding to FIG. 4, showing the fluralaner plasma concentration and efficacy, respectively.

Individual results for the animals in the group study are as follows.

TABLE 3 individual and summary statistics of fluralaner concentration levels (ng/mL)—Group 2

| Animal ID | Time (h) | | | | | | | | | | | | | | |
|---|---|---|---|---|---|---|---|---|---|---|---|---|---|---|---|
| Statistic | 0 | 24 | 48 | 72 | 96 | 120 | 144 | 168 | 192 | 216 | 240 | 384 | 528 | 624 | 720 |
| 86A 749 | 0 | 158 | 283 | 378 | 572 | 535 | 447 | 536 | 558 | 551 | 368 | 523 | 235 | 182 | 275 |
| 86C DCF | 0 | 129 | 253 | 373 | 515 | 554 | 454 | 520 | 455 | 472 | 724 | 715 | 517 | 403 | 248 |
| 86F AA9 | 0 | 135 | 245 | 361 | 471 | 469 | 495 | 461 | 497 | 493 | 422 | 1000 | 283 | 227 | 187 |
| ABD CB0 | 0 | 149 | 312 | 469 | 602 | 536 | 550 | 580 | 548 | 650 | 577 | 593 | 357 | 261 | 293 |
| AC4 107 | 0 | 160 | 257 | 366 | 497 | 495 | 497 | 491 | 542 | 477 | 386 | 561 | 267 | 223 | 300 |
| ACD B84 | 0 | 142 | 269 | 381 | 496 | 465 | 510 | 521 | 456 | 468 | 423 | 893 | 373 | 280 | 285 |
| n | 6 | 6 | 6 | 6 | 6 | 6 | 6 | 6 | 6 | 6 | 6 | 6 | 6 | 6 | 6 |
| Mean | 0.0 | 145.5 | 269.8 | 388.0 | 525.5 | 509.0 | 492.2 | 518.2 | 509.3 | 518.5 | 483.3 | 714.2 | 338.7 | 262.7 | 264.7 |
| SD | 0.00 | 12.44 | 24.56 | 40.37 | 50.55 | 37.85 | 37.92 | 40.40 | 46.65 | 71.32 | 139.19 | 194.10 | 102.27 | 76.62 | 42.15 |
| Std Err | 0.00 | 5.08 | 10.03 | 16.48 | 20.64 | 15.45 | 15.48 | 16.49 | 19.04 | 29.12 | 56.82 | 79.24 | 41.75 | 31.28 | 17.21 |
| CV % | | 8.5 | 9.1 | 10.4 | 9.6 | 7.4 | 7.7 | 7.8 | 9.2 | 13.8 | 28.8 | 27.2 | 30.2 | 29.2 | 15.9 |

TABLE 3-continued

| individual and summary statistics of fluralaner concentration levels (ng/mL)—Group 2 | | | | | | | | | | | | | | | |
|---|---|---|---|---|---|---|---|---|---|---|---|---|---|---|---|
| Animal ID | Time (h) | | | | | | | | | | | | | | |
| Statistic | 0 | 24 | 48 | 72 | 96 | 120 | 144 | 168 | 192 | 216 | 240 | 384 | 528 | 624 | 720 |
| GeoMean | | 145.1 | 268.9 | 386.4 | 523.5 | 507.8 | 491.0 | 516.9 | 507.5 | 514.8 | 468.6 | 693.3 | 327.0 | 254.4 | 261.5 |
| Median | 0.0 | 145.5 | 263.0 | 375.5 | 506.0 | 515.0 | 496.0 | 520.5 | 519.5 | 485.0 | 422.5 | 654.0 | 320.0 | 244.0 | 280.0 |
| Minimum | 0 | 129 | 245 | 361 | 471 | 465 | 447 | 461 | 455 | 468 | 368 | 523 | 235 | 182 | 187 |
| Maximum | 0 | 160 | 312 | 469 | 602 | 554 | 550 | 580 | 558 | 650 | 724 | 1000 | 517 | 403 | 300 |

Efficacy values are summarized in the table below:

TABLE 4

| Efficacy using geometric mean - live ticks: *Rhipicephalus sanguineus* | | | |
|---|---|---|---|
| | Control | Group 2 | |
| Day | Group 1 Mean | Mean | Percentage efficacy |
| Day 3 | 26.0 | 0.0 | 100 |
| Day 5 | 27.7 | 0.0 | 100 |
| Day 7 | 41.8 | 0.0 | 100 |
| Day 9 | 22.4 | 11.8 | 47.3 |
| Day 11 | 35.1 | 7.8 | 77.8 |
| Day 13 | 30.3 | 4.5 | 85.0 |
| Day 17 | 26.7 | 5.1 | 80.8 |
| Day 23 | 30.0 | 16.2 | 46.1 |
| Day 27 | 32.2 | 6.8 | 78.9 |
| Day 31 | 30.2 | 13.3 | 56.1 |

In conclusion, the efficacy against ticks is present from the first day after treatment (at least 24 to 48 hours with infestation at D1, first measurement at D3).

With administration of a charging dose followed by mini-doses during 4 days, a minimal efficacy dose of 100 ng/ml is present in the animal, which is expected to lead to efficacy of at least about 30 days.

Bioavailability is about 5 times higher than expected.

Discussion and Conclusion

The mean terminal half-life of fluralaner was 372.42 h.

The maximum concentration over the entire study period occurred after the initial 4 consecutive doses of 250 µg/kg per day of fluralaner (on Days 0 to 3) in one of the six of the animals, it occurs after the 6 consecutive doses of 35 µg/kg per day (Days 4 to 9) in two of the six animals, and after the single high dose of 600 µg/kg on Day 11 in four of the six animals. This indicates that, although the inter-animal variation of the concentrations of fluralaner was relatively low, the intra-animal variation was quite large.

Steady state concentrations had not been reached after the fourth dose application 250 µg/kg per day (on Day 3), because the mean trough concentrations were still in an increasing phase for the period after the fourth dose on Day 3 and before the next dose (of 35 µg/mL) on Day 4.

Steady state concentrations were reached with the 35 µg/kg per day dose application from Day 4 to Day 9.

The efficacy of fluralaner against ticks was 100% for the period during the first four doses of 250 µg/kg per day of fluralaner and the following three doses of 35 ug/kg per day. The efficacy decreased to approximately between 50% to 75% from Day 9 to Day 27 after the remaining consecutive doses of 35 µg/kg per day and the following single dose of 600 µg/kg on Day 11.

The efficacy of fluralaner against fleas was 92% on Day 3 (thus following 3 consecutive doses of 250 µg/kg per day of fluralaner.

Other Data: Comparison with Literature Data

1. Fleas Efficacy, Comparison Between Experimental Data and Literature Data

TABLE 5

| plasma pharmacokinetic parameters of fluralaner in dogs after either single oral or single i.v. administration<br>Table 1 Plasma pharmacokinetic parameters of fluralaner in dogs after either single oral or single i.v. administration | | | | |
|---|---|---|---|---|
| Parameters | Oral 12.5 mg/kg n = 6 | Oral 25.0 mg/kg n = 6 | Oral 50.0 mg/kg n = 6 | Intravenous 12.5 mg/kg n = 6 |
| $C_{max}$ (ng/mL) | 2144 ± 860 | 3948 ± 1734 | 5419 ± 2086 | 7109 ± 908 |
| $t_{max}^{a}$ (day) | 1 (range 0.08-2) | 1 (range 1-2) | 1 (range 0.17-3) | n/a |
| $AUC_{(0-d112)}$ (day * ng/mL) | 29665 ± 13858 | 46115 ± 18932 | 70171 ± 26412 | 87198 ± 11835 |
| $AUC_{(0\rightarrow\infty)}$ (day * ng/mL) | 29922 ± 13808 | 46416 ± 18929 | 70531 ± 26529 | 87779 ± 12004 |
| $t_{1/2}$ (day) | 13 ± 1 | 12 ± 3 | 14 ± 1 | 15 ± 2 |
| MRT (day) | 19 ± 2 | 15 ± 4 | 17 ± 3 | 20 ± 3 |
| Cl (L/kg/day) | n/a | n/a | n/a | 0.14 ± 0.02 |
| $V_z$ (L/kg) | n/a | n/a | n/a | 3.1 ± 0.5 |

[a]Median, other values are mean ± standard deviation.
n/a - not applicable.

TABLE 6

| Cmax (µg/l) | Tmax (d) | AUClast (µg/L * d) | AUCextra (µg/L * d) | AUCtot (µg/L * d) | $t_{1/2}$ (d) |
|---|---|---|---|---|---|
| 31994.2 | 3 | 483104.77 | 68221.98 | 551326.76 | 9.56 |
| 5419 | 1 | | | 70531 | 14 |
| 5.90 | | | | | |

Figure 7:
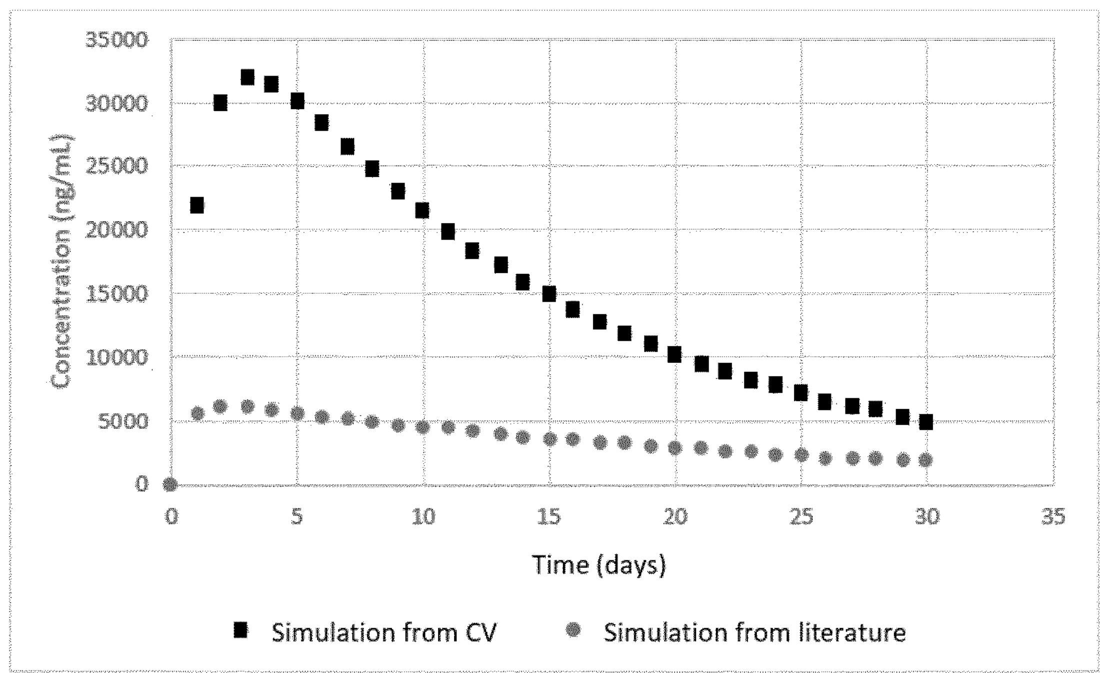
FIG. 7 shows the mean plasma concentration as a function of time, in simulation from CV and simulation from literature.

FIG. 7 shows the mean plasma concentration as a function of time, in simulation from CV and simulation from literature.

Measured Cmax is about 5.9 times what would have been expected.

2. Fleas Efficacy: Comparison Between Experimental Data and Literature Data

FIG. 8 shows the mean plasma concentration as a function of days, in the treatment study and in simulated data from literature.

General Conclusion

Both oral studies provide significantly improved bioavailability of the active substance fluralaner compared to the literature data available.

Both oral studies provide unexpectedly significant improvement in bioavailability, enabling a significantly lower dosage required to achieve superior pharmacokinetic profiles and attain efficacy against ticks and fleas.

3. Topical Administration Study

1—Pharmacokinetic

Protocol

The objective of the study is to determine the pharmacokinetic profile of the Bravecto spot-on containing fluralaner after a single topical administration on dogs at a dose rate of 6250 μg/kg after feeding.

IVP: Investigational Veterinary Product, is Bravecto spot-on containing fluralaner at a dose rate of 6250 μg/kg (22.3112 μL/kg) on Day 0

Ten dogs were enrolled in the study of which six were included meeting the inclusion criteria. In addition, veterinary examinations (Day −14 and Day −2±one day), general health observations (all days) and weighing of all dogs (Day −2±one day) were performed.

On Day 0, all dogs will receive the IVP at a dose rate of 6250 μg/kg. The quantity of IVP to be administered will be calculated according to the dog's individual body weight. Dogs will be observed hourly (±15 minutes) for four hours after administration on Day 0.

Blood specimens will be collected from all dogs on Days −14 and −7 for clinical chemistry and hematology for inclusion and for pharmacokinetic analysis prior to IVP treatment on Day 0 and on Days 1 (+24 hours), 3 (+72 hours), 5 (+120 hours), 7 (+168 hours), 10 (+240 hours), 14 (+336 hours), 21 (+504 hours), 28 (+672 hours), 35 (+840 hours), 42 (+1008 hours), 49 (+1176 hours), 56 (+1344 hours) and 60 (+1440 hours).

Results

No Adverse Events as a result of the Investigational Veterinary Product were recorded.

The mean terminal half-life of fluralaner was 387.65 h (range: 339.9 h to 490.5 h).

The mean maximum concentration (Cmax) of fluralaner was 238 ng/mL (range: 161.0 ng/mL to 353 ng/mL).

The mean AUC0-t of fluralaner was 181191.8 ng·h/mL.

FIG. 9 shows the mean fluralaner plasma concentrations as a function of time.

The results for individual animals in the study group were as follows.

TABLE 7 individual and summarized statistics of fluralaner concentration evels (ng/mL)

| Animal ID | Time (h) | | | | | | |
|---|---|---|---|---|---|---|---|
| Statistic | 0 | 24 | 72 | 120 | 168 | 240 | 336 |
| 698 401 | 0.00 | 34.20 | 99.40 | 151.00 | 202.00 | 204.00 | 190.00 |
| 86A 347 | 0.00 | 22.50 | 121.00 | 191.00 | 353.00 | 258.00 | 249.00 |
| 86A E66 | 0.00 | 37.20 | 56.90 | 78.40 | 205.00 | 136.00 | 121.00 |
| 86A F42 | 0.00 | 4.77 | 15.70 | 42.50 | 106.00 | 125.00 | 150.00 |
| 86D 6FA | 0.00 | 4.75 | 10.80 | 26.50 | 81.90 | 74.90 | 70.60 |
| 886 2A0 | 0.00 | 3.97 | 51.50 | 96.90 | 126.00 | 219.00 | 137.00 |
| n | 6 | 6 | 6 | 6 | 6 | 6 | 6 |
| Mean | 0.000 | 17.898 | 59.217 | 97.717 | 178.983 | 169.483 | 152.933 |
| SD | 0.000 | 15.484 | 44.124 | 63.301 | 99.043 | 68.592 | 61.096 |
| Std Err | 0.000 | 6.321 | 18.014 | 25.843 | 40.434 | 28.003 | 24.942 |
| CV % | | 86.5 | 74.5 | 64.8 | 55.3 | 40.5 | 39.9 |
| GeoMean | | 11.707 | 42.599 | 79.198 | 158.723 | 156.472 | 142.307 |
| Median | 0.000 | 13.635 | 54.200 | 87.650 | 164.000 | 170.000 | 143.500 |
| Minimum | 0.00 | 3.97 | 10.80 | 26.50 | 81.90 | 74.90 | 70.60 |
| Maximum | 0.00 | 37.20 | 121.00 | 191.00 | 353.00 | 258.00 | 249.00 |

| Animal ID | Time (h) | | | | | | |
|---|---|---|---|---|---|---|---|
| Statistic | 504 | 672 | 840 | 1008 | 1176 | 1344 | 1440 |
| 698 401 | 180.00 | 137.00 | 113.00 | 109.00 | 69.60 | 52.40 | 48.40 |
| 86A 347 | 188.00 | 130.00 | 99.90 | 181.00 | 68.70 | 47.50 | 40.30 |
| 86A E66 | 111.00 | 112.00 | 81.40 | 136.00 | 70.70 | 51.30 | 43.00 |
| 86A F42 | 161.00 | 149.00 | 97.60 | 127.00 | 83.60 | 67.90 | 55.30 |
| 86D 6FA | 67.50 | 59.10 | 46.80 | 80.50 | 30.20 | 24.10 | 22.70 |
| 886 2A0 | 150.00 | 267.00 | 150.00 | 225.00 | 115.00 | 80.50 | 70.20 |
| n | 6 | 6 | 6 | 6 | 6 | 6 | 6 |
| Mean | 142.917 | 142.350 | 98.117 | 143.133 | 72.967 | 53.950 | 46.650 |
| SD | 45.807 | 68.724 | 34.146 | 51.957 | 27.363 | 19.191 | 15.873 |
| Std Err | 18.700 | 28.056 | 13.940 | 21.211 | 11.171 | 7.835 | 6.480 |
| CV % | 32.1 | 48.3 | 34.8 | 36.3 | 37.5 | 35.6 | 34.0 |
| GeoMean | 135.258 | 129.378 | 92.578 | 135.521 | 67.918 | 50.618 | 44.135 |
| Median | 155.500 | 133.500 | 98.750 | 131.500 | 70.150 | 51.850 | 45.700 |
| Minimum | 67.50 | 59.10 | 46.80 | 80.80 | 30.20 | 24.10 | 22.70 |
| Maximum | 188.00 | 267.00 | 150.00 | 225.00 | 115.00 | 80.50 | 70.20 |

LOQ: 1.00 ng/mL

All dogs were treated with Bravecto Spot-on containing fluralaner, as a single topical administration of 6250 μg/kg

TABLE 8 individual and summary statistics of fluralaner PK parameters

| Animal ID Statistic | Cmax (ng/mL) | Tmax (h) | Lambda z | t½ (h) | $AUC_{0-t}$ (ng · h/mL) | $AUC_{0-inf}$ (ng · h/mL) | AUC extrapolated (%) |
|---|---|---|---|---|---|---|---|
| 698 401 | 204.0 | 240 | 0.0014 | 490.5 | 179073 | 213325 | 16.1 |
| 86A 347 | 353.0 | 168 | 0.0020 | 339.9 | 211875 | 231639 | 8.5 |
| 86A E66 | 205.0 | 168 | 0.0019 | 367.4 | 142230 | 165025 | 13.8 |
| 86A F42 | 161.0 | 504 | 0.0018 | 375.1 | 155100 | 185028 | 16.2 |
| 86D 6FA | 81.9 | 168 | 0.0011 | 624.1 | 74537 | 94975 | 21.5 |
| 886 2A0 | 267.0 | 672 | 0.0019 | 365.2 | 217681 | 254668 | 14.5 |
| n | 6 | 6 | 6 | 6 | 6 | 6 | 6 |
| Mean | 211.98 | 320.0 | 0.00170 | 427.05 | 163416.1 | 190776.5 | 15.10 |
| SD | 92.245 | 216.10 | 0.000358 | 110.011 | 52830.86 | 56805.50 | 4.205 |
| Std Err | 37.659 | 88.22 | 0.000146 | 44.912 | 21568.11 | 23190.75 | 1.717 |
| CV % | 43.5 | 67.5 | 21.1 | 25.8 | 32.3 | 29.8 | 27.8 |
| GeoMean | 193.18 | 269.8 | 0.00166 | 416.74 | 154460.7 | 182125.4 | 14.57 |
| Median | 204.50 | 204.0 | 0.00187 | 371.28 | 167086.7 | 199176.7 | 15.29 |
| Minimum | 81.9 | 168 | 0.0011 | 339.9 | 74537 | 94975 | 8.5 |
| Maximum | 353.0 | 672 | 0.0020 | 624.1 | 217681 | 254668 | 21.5 |

All dogs were treated with Bravecto Spot-on containing fluralaner, as a single to administration of 6250 μg/kg TABLE 8a individual and summarized statistics of fluralaner PK parameters without 86D 6FA

| Animal ID Statistic | Cmax (ng/mL) | Tmax (h) | Lambda z | t½ (h) | $AUC_{0-t}$ (ng · h/mL) | $AUC_{0-inf}$ (ng · h/mL) | AUC extrap (%) |
|---|---|---|---|---|---|---|---|
| 698 401 | 204.0 | 240 | 0.0014 | 490.5 | 179073 | 213325 | 16.1 |
| 86A 347 | 353.0 | 168 | 0.0020 | 339.9 | 211875 | 231639 | 8.5 |
| 86A E66 | 205.0 | 168 | 0.0019 | 367.4 | 142230 | 165025 | 13.8 |
| 86A F42 | 161.0 | 504 | 0.0018 | 375.1 | 155100 | 185028 | 16.2 |
| 886 2A0 | 267.0 | 672 | 0.0019 | 365.2 | 217681 | 254668 | 14.5 |
| n | 5 | 5 | 5 | 5 | 5 | 5 | 5 |
| Mean | 238.00 | 350.4 | 0.00182 | 387.65 | 181191.8 | 209936.8 | 13.82 |
| SD | 74.565 | 226.81 | 0.000237 | 59.015 | 33452.17 | 35780.04 | 3.123 |
| Std Err | 33.347 | 101.43 | 0.000106 | 26.392 | 14960.26 | 16001.32 | 1.396 |
| CV % | 31.3 | 64.7 | 13.0 | 15.2 | 18.5 | 17.0 | 22.6 |
| GeoMean | 229.35 | 296.6 | 0.00180 | 384.41 | 178692.7 | 207454.4 | 13.48 |
| Median | 205.00 | 240.0 | 0.00189 | 367.44 | 179073.2 | 213325.3 | 14.52 |
| Minimum | 161.0 | 168 | 0.0014 | 339.9 | 142230 | 165025 | 8.5 |
| Maximum | 353.0 | 672 | 0.0020 | 490.5 | 217681 | 254668 | 16.2 |

Animal 86D GFA was excluded from the analysis
All dogs were treated with Bravecto Spot-on containing fluralaner, as a single topical administration of 6250 μg/kg Conclusion The mean values for the PK profile were calculated as follows as summarized from Table 8a:

TABLE 9 mean values for PK profile

| Parameter (unit) | Mean value |
|---|---|
| Cmax (ng/mL | 238.00 |
| Tmax (h) | 350.4 |
| Lambda z | 0.00182 |
| t1/2 (h) | 387.65 |
| AUC 0-t (ng · h/mL) | 181191.8 |
| AUC 0-int (ng · h/mL) | 209936.8 |
| AUC extrap (%) | 13.82 |

General Conclusion

Topical study provides an important and theoretical efficacy against fleas and ticks according to the plasma concentration of fluralaner.

Enabling a significantly lower dosage required to achieve superior pharmacokinetic profiles and attain efficacy against ticks and fleas.

Pharmacokinetic analysis and efficacy statistical analysis

1. Pharmacokinetic Parameters

The PK parameters of fluralaner were calculated using a non-compartmental approach.

The following rules were applied for the calculation of the PK parameters:

All the plasma concentrations, validated by the bioanalytical laboratory, were used for the PK analysis.

The actual blood sampling times were used throughout.

Concentrations below the Limit of Quantification (LOQ) value were considered as zero from time zero (predose) up to the time at which the first quantifiable concentration above the LOQ value was observed. Concentrations below the LOQ value between two quantifiable concentrations were considered as missing. Trailing concentrations below the LOQ value were not used in calculations.

The following PK parameters of fluralaner were derived for each animal after IVP administration:

Cmax the observed maximum concentration in plasma measured after dosing.

tmax the time at which Cmax was apparent.

λz the terminal rate constant (λz) was estimated by log-linear regression analysis on data points visually assessed, to be on the terminal log-linear phase. For the slope of the terminal elimination phase to be accepted as reliable, the following criteria were used:

- the terminal data points were apparently randomly distributed about a single straight line (on visual inspection),
- a minimum of three data points, including the last measured data point and excluding Cmax, were available for the regression.

If these two criteria could not be met, the slope of the terminal elimination phase was considered as not calculable and all the parameters derived from this value (AUC0-□, t1/2) were reported as not calculable (NC).

$t_{1/2}$ the terminal plasma half-life ($t_{1/2}$) was calculated according to the following equation:

$$t_{1/2} = \frac{0.693}{\lambda z}$$

$AUC_{0-t}$ the area under the concentration-time curve from time zero (pre-dose) to the time of last quantifiable concentration (t) was calculated using a linear trapezoidal method.

$AUC_{0-\infty}$ the area under the concentration-time curve from time zero to infinity:

[$AUC_{0-\infty}=AUC_{0-t}+(Ct/\lambda z)$], where Ct was the observed concentration of drug for the last sample on the PK profile in which the drug was detected, and λz was as defined above.

Area Extra (%) (Extrapolated Area Under the Curve):

The extrapolated area under the curve, expressed as a percentage of the total area, AUCinf, was also calculated as:

$$\text{Area Extra (\%)}=(AUC_{0-\infty}-AUC_{0-t})/AUC0\text{-}\infty*100\%.$$

The percentage of extrapolation of $AUC_{0-\infty}$ should normally not exceed 20%.

2. Missing Status and Outliers

The missing status given to data points implied that these points were systematically ignored during the calculation and therefore had no effect on the results.

Possible exclusion of values could be performed if, in the judgment of the pharmacokineticist, they were deemed not to be "pharmacokinetically relevant". No data were excluded.

3. Statistical Analysis of Pharmacokinetic Concentrations and Parameters

The statistical analysis was performed in accordance with the recommendations of:

EMEA/CVMP/133/99: Guidelines for the conduct of pharmacokinetic studies in target animal species.

All values below the LOQ value were substituted with half the LOQ value to obtain more accurate estimates of the descriptive statistics for the concentrations.

Descriptive statistics of the concentration levels and the PK parameters were calculated and presented as arithmetic and geometric mean, standard deviation, standard error of the mean, coefficient of variation (CV %), median, maximum and minimum. The plasma concentration-time profiles were plotted individually and as a group mean.

4. Description of the Software Used for the Pharmacokinetic and Statistical Analyses The PK analysis was performed using WinNonlin Version 5.0 or higher (Pharsight, USA). The statistical analysis was performed using SAS Version 9.3 TS Level 1M2.

5. Efficacy 5.1 Analysis of Data not Used to Calculate the Product Effect

Data of all health and clinical observations/examinations were listed. Descriptive statistics of body weight and hair length were tabulated.

5.2 Comparison of Body Weight, Hair Length and Flea Counts

Body weight, hair length and live flea counts, measured during the acclimatisation period, were compared between the groups in order to evaluate their homogeneity at the time of inclusion. The groups were compared using a one-way Analysis of Variance (ANOVA) (Proc GLM procedure in SAS) with a treatment effect, assuming a normal distribution of the data.

5.3 Methods for Calculating the Adulticidal Product Effect

The efficacy against ticks and fleas were calculated for the study groups at each assessment day according to the formulas given below.

With consideration of available guidelines, EMEA 2000, it was decided that the primary efficacy calculations would be based on arithmetic mean values rather than geometric mean values.

Efficacy calculations based on geometric mean values were, however, also reported on. Such calculations were based on the geometric mean values of the tick or flea (count+1) data. One (1) was subsequently subtracted from the result to obtain a meaningful value for the geometric mean of each group.

Efficacy was calculated as follows:

$$\text{Efficacy (\%)}=100\times(Mc-Mt)/Mc, \text{ where:}$$

- Mc=Mean number of live ticks (categories 1 to 2) or live fleas on dogs in the negative control group (group 1) at a specific time point.
- Mt=Mean number of live ticks (categories 1 to 2) or live fleas on dogs in the IVP group (group 2)

at a specific time point.

Descriptive statistics (mean, minimum, maximum, standard deviation, percentage coefficient of variation (CV %), geometric mean and median) of tick and flea counts for the various assessment days, were calculated and presented.

Summary of Concepts

1 Fluralaner Low Dose Embodiments

1. Fluralaner for use in protecting an animal from a parasitic invertebrate pest, wherein fluralaner is administered to said animal at a reduced dosage.

2. Fluralaner for use in protecting an animal from a parasitic invertebrate pest, wherein fluralaner is administered to said animal at a reduced dosage, said reduced dosage being comprised between 0.025 mg/kg and 12.5 mg/kg, preferably between 0.025 mg/kg and 0.05 mg/kg, more preferably between 0.1 mg/kg and 9.37 mg/kg.

3. Fluralaner for use in protecting an animal from a parasitic invertebrate pest, wherein fluralaner is administered at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92 times in a period of 1, 2, 3, 4, 5, 6, 7, 8, 9, 10, 11, 12 months to said animal at a reduced dosage, more preferably in a period of 3 months to said animal at a reduced dosage.

4. Fluralaner for use in protecting an animal from a parasitic invertebrate pest, wherein fluralaner is administered at a dosage comprised between 10 and 100 μg/kg/day, preferably at a dosage comprised between 20 and 50 μg/kg/day, even more preferably at a dosage comprised between 30 and 40 μg/kg/day.

5. Fluralaner for use in protecting an animal from a parasitic invertebrate pest, wherein fluralaner is administered at a dosage of around 35 μg/kg/day.

6. A method for protecting an animal from a parasitic invertebrate pest comprising orally or parenterally administering to the animal a pesticidally effective amount of fluralaner, an N-oxide, a salt or an enantiomer thereof, wherein fluralaner is administered at a dosage comprised between 10 and 100 μg/kg/day, preferably at a dosage comprised between 20 and 50 μg/kg/day, even more preferably at a dosage comprised between 30 and 40 μg/kg/day.

7. A method for protecting an animal from a parasitic invertebrate pest comprising orally or parenterally administering to the animal a pesticidally effective amount of fluralaner, an N-oxide, a salt or an enantiomer thereof, wherein fluralaner is administered at a dosage comprised between 10 and 100 μg/kg/day, preferably at a dosage comprised between 20 and 50 μg/kg/day, even more preferably at a dosage comprised between 30 and 40 μg/kg/day and wherein fluralaner is administered at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92 times in a period of one week or 1, 2, or 3 months to said animal at a reduced dosage, more preferably in a period of 3 months to said animal.

8. A method for the treatment and prevention of a parasitic infestation or infection in or on an animal, comprising treating the animal with a parasiticidally effective amount of fluralaner or a pharmaceutically acceptable salt thereof wherein fluralaner is administered at a dosage comprised between 10 and 100 μg/kg/day, preferably at a dosage comprised between 20 and 50 μg/kg/day, even more preferably at a dosage comprised between 30 and 40 μg/kg/day, even more preferably at a dosage of around 35 μg/kg/day.

9. A method for the treatment and prevention of a parasitic infestation or infection in or on an animal, comprising treating the animal with a parasiticidally effective amount of fluralaner or a pharmaceutically acceptable salt thereof wherein fluralaner is administered at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92 times in a period of one week or 1, 2, or 3 months to said animal at a reduced dosage, more preferably in a period of 3 months to said animal.

10. A soft chewable veterinary pharmaceutical composition for oral administration comprising fluralaner or a salt or solvate thereof, a solid carrier and a solvent wherein the solvent is DMSO (dimethylsulfoxyde) wherein fluralaner is administered at a dosage comprised between 10 and 100 μg/kg/day, preferably at a dosage comprised between 20 and 50 μg/kg/day, even more preferably at a dosage comprised between 30 and 40 μg/kg/day.

11. A soft chewable veterinary pharmaceutical composition for oral administration comprising fluralaner or a salt or solvate thereof, a solid carrier and a solvent wherein the solvent is DMSO (dimethylsulfoxyde) wherein fluralaner is administered to said animal at a reduced dosage.

12. A method for treating a non-human mammal, comprising administering to the non-human animal reduced dosage of fluralaner, wherein the administration is carried out according to a dosage regimen comprising (i) an initial dose D0, administered at the beginning of treatment, representing at most 65% of the determined total dose, and (ii) a plurality of maintenance doses Di, administered sequentially during the duration of the treatment, the sum of the Di doses and of the DO dose being equal to the determined total dose that is the reduce dosage.

13. The method as in embodiment 12, wherein the initial dose D0 represents 0.5% to 60% of the determined total dose.

14. The method as in embodiment 12, wherein all the maintenance doses Di are identical.

15. The method as in embodiment 12, wherein each maintenance dose Di represents at most 35% of the initial dose D0.

16. The method as in embodiment 12, wherein the frequency of administration of the maintenance doses Di is constant throughout the treatment.

17. The method as in embodiment 12, wherein the frequency of administration of the maintenance doses Di is between 1 h and 1 month.

18. The method as in embodiment 12, wherein the duration of the treatment is between 1 month and 24 months.

19. The method as in embodiment 12, wherein Fluralaner is administered by means of a controlled-release device.

20. The method as in embodiment 18, wherein Fluralaner is applied by means of a smart collar.

21. The method as in embodiment 18, wherein Fluralaner is applied by means of a collar.

22. The method as in embodiment 18, wherein Fluralaner is applied orally.

23. The method as in embodiment 18, wherein Fluralaner is applied by means of an implant.

24. The method as in embodiment 12, wherein the initial dose D0 represents from 0.5-10% of the determined total dose, wherein each maintenance dose Di is identical and administered every 3 days and wherein the preferential duration of the treatment is greater than 2 months.

25. A device for delivering Fluralaner to a non-human mammal, wherein the device comprises a determined total dose of Fluralaner and a controlled sequential release system ensuring the delivery of an initial dose D0 of Fluralaner at the beginning of the treatment, said dose D0 representing 0.5% to 65% of the determined total dose, and of a plurality of maintenance doses Di of the compound, the sum of the Di doses and of the DO dose being equal to the determined total dose that is the reduce dosage.

26. The method as in embodiment 12, wherein each maintenance dose Di represents at most 20% of the initial dose D0.

27. The method as in embodiment 1, wherein each maintenance dose Di represents at most 10% of the initial dose D0.

28. The method as in embodiment 1, wherein the frequency of administration of the maintenance doses Di is between 2 h and 15 days.

29. The method as in embodiment 1, wherein the frequency of administration of the maintenance doses Di is between 4 h and 7 days.

30. The method as in embodiment 1, wherein the frequency of administration of the maintenance doses Di is between 12 h and 96 h.

31. The method as in embodiment 1, wherein the duration of the treatment is between 1 and 2 months.

32. The method as in embodiment 1, wherein the duration of the treatment is between 2 and 12 months.

2 Fluralaner New Galenic Embodiments 2.1. Fluralaner for use in protecting an animal from a parasitic invertebrate pest, wherein fluralaner is administered to said animal as a solid formulation.

2.2. Fluralaner composition of embodiment 2.1, wherein the solid formulation is a tablet or a soft chew (oral chewy composition that has a certain elasticity when chewed by the animal).

2.3. Fluralaner composition of embodiments 2.1 or 2.2, wherein the solid formulation is a pet food composition.

2.4. Composition of any one of embodiments 2.1 to 2.3, wherein the formulation is an implant.

2.5. Composition of embodiment 2.4, wherein the implant having an immediate release of fluralaner in the attack phase (in the hours following the implantation) in order to establish the efficient dose (effective amount) within hours 48 hours, preferably 24 hours, more preferably 12 hours and even more preferably 4, 2, 1 or ½ hours) and with preferably a release rate of order 0 in the maintenance phase.

2.6. Composition of any one of embodiments 2.4 and 2.5, wherein the implant is degradable or biodegradable.

2.7. Composition of any one of embodiments 2.4 to 2.6, wherein the implant is or includes solid or is or includes a liquid.

2.8. Composition or method of any of embodiments 2.1 to 2.3, wherein the formulation is a patch.

2.9. Composition or method of embodiment 2.8, wherein the formulation is a patch having an immediate release of fluralaner in the attack phase (in the hours following the implantation) in order to establish the efficient dose (effective amount) within 48 hours, preferably 24 hours, more preferably 12 hours and even more preferably 4, 2, 1 or ½ hours) and with preferably a release rate of order 0 in the maintenance phase.

2.10. Composition or method of any of embodiments 2.8 and 2.9, wherein the patch is degradable or biodegradable.

2.11. Composition or method of any of embodiments 2.8-2.10, wherein the patch is or includes a solid, or is or includes a liquid.

2.12. Fluralaner for use in protecting an animal from a parasitic invertebrate pest, wherein fluralaner is administered to said animal as a liquid formulation.

2.13. Fluralaner according to embodiment 2.12, wherein the liquid formulation is a solution or a suspension for injection.

2.14. Fluralaner for use in protecting an animal from a parasitic invertebrate pest, wherein the fluralaner is administered to said animal as a topical formulation.

2.15. Fluralaner for use in protecting an animal from a parasitic invertebrate pest, wherein fluralaner is administered to said animal orally as a paste. Such a paste allows a good adjustment of the dose in order to treat the targeted parasites.

2.16. Fluralaner for use in protecting an animal from a parasitic invertebrate pest, wherein fluralaner is administered to said animal as a collar.

2.17. Method for protecting an animal from a parasitic invertebrate pest comprising orally administering to the animal a pesticidally effective amount of fluralaner, an N-oxide, a salt or an enantiomer thereof that includes increasing the amount of fat in the composition containing the fluralaner (pet food enriched in fats, or tablets or soft chews or treets enriched in fats), as compared to a conventional diet for the the animal.

2.18. Method according to embodiment 2.17, using a composition of any of embodiments 2.1-2.17.

2.19. A method for protecting an animal from a parasitic invertebrate pest comprising orally administering to the animal a pesticidally effective amount of fluralaner, an N-oxide, a salt or an enantiomer thereof that consists in increasing the palatability (the taste, the savoury) of the composition containing the fluralaner (pet food enriched in fats, or tablets or soft chews or treets enriched in fats).

2.20. Method according to embodiment 2.19, using a composition of any of embodiments 2.1-2.17.

2.21. A repellent pest control system for the controlled release of fluralaner from a polymer matrix which comprises: a vinyl polymer a liquid plasticizer for said polymer, said plasticizer being present in the maximum amount possible but still maintaining a dry and flowable blend of plasticizer and polymer and triphenyl phosphate, said triphenyl phosphate being present in an amount sufficient to serve as a carrier for said active ingredient.

2.22. Solid moulded bodies which are for external use against parasites on animals, which are based on a polyolefin matrix and which comprise:

- one or more esters comprising a dihydric or trihydric alcohol having up to three carbon atoms and fatty acids having from 6 to 18 carbon atoms
- one or more active compounds comprising fluralaner
- and, where appropriate, additional auxiliary substances and additives 2.23. A method of controlling fleas which comprises continuously administering to the haircoat of a homeothermic animal an effective amount of fluralaner from a sustained release matrix (the sustained release matrix being a collar or a patch) at an average rate of about 0.01 mg/kg/day to about 0.10 mg/kg/day, preferably of about 0.02 mg/kg/day to about 0.08 mg/kg/day, more preferably of about 0.034 mg/kg/day to about 0.036 mg/kg/day.

2.23. A method of controlling fleas on an animal which comprises continuously administering to the haircoat an effective amount of fluralaner from a sustained release matrix material formulated to release fluralaner in the average daily amount of about 0.01 mg/kg/day to about 0.10 mg/kg/day, preferably of about 0.02 mg/kg/day to about 0.08 mg/kg/day, more preferably of about 0.034 mg/kg/day to about 0.036 mg/kg/day, fluralaner for over 90 days, preferably 120 days, more preferably 150 days and even more preferably 180 days.

2.24. A local topical formulation comprising an ectoparasitically effective amount of fluralaner and a veterinarily acceptable carrier, in the absence of an effective amount of a fluralaner crystallization inhibitor.

2.25. A topical composition comprising: fluralaner or a pharmaceutically acceptable salt thereof at a pesticidally effective amount; at least one surfactant and at least one crystallization inhibitor, wherein the flashpoint of the composition is at least 40° C.

2.26. A method of raising the flashpoint of a topical composition comprising fluralaner, or a pharmaceutically acceptable salt thereof at a pesticidally effective amount, comprising using an effective amount of a surfactant, a crystallization inhibitor, an organic solvent and an organic cosolvent.

2.27. A method of improving the stability of a composition comprising fluralaner or a pharmaceutically acceptable salt thereof at a pesticidally effective amount, comprising using an effective amount of a surfactant and a crystallization inhibitor.

2.28. A system, bodies, method, formulation or composition of any of embodiments 2.21-2.27, using a composition of any of embodiments 1-17.

2.29. A system, bodies, method, formulation or composition of any of embodiments 2.21-2.28, using a method of any of embodiments 18-20.

3 Fluralaner New Posology Embodiments 3.1. Use of fluralaner at a dose of 5-10 ng/mL for the immediate and efficient treatment of a non-human animal against fleas.

3.2. Use of fluralaner at a dose of around 90 ng/mL for the rapid and efficient treatment of a non-human animal against ticks.

3.3. Use of fluralaner at a reduced dosage for the immediate and efficient treatment of a non-human animal against fleas.

3.4. Use of fluralaner at a reduced dosage for the immediate and efficient treatment of a non-human animal against ticks.

3.5. Use of fluralaner at a reduced dosage for the rapid and efficient treatment of a non-human animal against fleas.

3.6. Use of fluralaner at a reduced dosage for the rapid and efficient treatment of a non-human animal against ticks.

3.7. Use of fluralaner at a reduced dosage, said reduced dosage being comprised between 0.025 mg/kg and 12.5 mg/kg, more preferably between 0.1 mg/kg and 9.37 mg/kg 3.8. Use of fluralaner at a reduced dosage, said reduced dosage being comprised between 0.025 mg/kg and 12.5 mg/kg, more preferably between 0.1 mg/kg and 9.37 mg/kg, for the immediate and efficient treatment of a non-human animal against ticks.

3.9. Use of fluralaner at a reduced dosage, said reduced dosage being comprised between 0.025 mg/kg and 12.5 mg/kg, more preferably between 0.1 mg/kg and 9.37 mg/kg, for the rapid and efficient treatment of a non-human animal against fleas.

3.10. Use of fluralaner at a reduced dosage, said reduced dosage being comprised between 0.025 mg/kg and 12.5 mg/kg, more preferably between 0.1 mg/kg and 9.37 mg/kg, for the rapid and efficient treatment of a non-human animal against ticks.

3.11. Use of fluralaner at a reduced dosage for the immediate and efficient treatment of a non-human animal against fleas wherein fluralaner is administered at a dosage comprised between 10 and 100 μg/kg, preferably at a dosage comprised between 20 and 50 g/kg, even more preferably at a dosage comprised between 30 and 40 μg/kg and more preferably wherein fluralaner is administered at a dosage of around 35 μg/kg.

3.12. Use of fluralaner at a reduced dosage for the immediate and efficient treatment of a non-human animal against ticks wherein fluralaner is administered at a dosage comprised between 10 and 100 μg/kg, preferably at a dosage comprised between 20 and 50 g/kg, even more preferably at a dosage comprised between 30 and 40 jg/kg and more preferably wherein fluralaner is administered at a dosage of around 35 μg/kg.

3.13. Use of fluralaner at a reduced dosage for the rapid and efficient treatment of a non-human animal against fleas wherein fluralaner is administered at a dosage comprised between 10 and 100 μg/kg, preferably at a dosage comprised between 20 and 50 μg/kg, even more preferably at a dosage comprised between 30 and 40 g/kg and more preferably wherein fluralaner is administered at a dosage of around 35 μg/kg.

3.14. Use of fluralaner at a reduced dosage for the rapid and efficient treatment of a non-human animal against ticks wherein fluralaner is administered at a dosage comprised between 10 and 100 μg/kg, preferably at a dosage comprised between 20 and 50 g/kg, even more preferably at a dosage comprised between 30 and 40 jg/kg and more preferably wherein fluralaner is administered at a dosage of around 35 μg/kg.

3.15. Fluralaner for use in protecting a dog from a parasitic invertebrate pest (ticks, flea or mite), wherein the compound is administered orally, wherein the compound is administered 4 hours prior to a walk in a dangerous environment.

3.16 Fluralaner for use in protecting an animal from a parasitic invertebrate pest, wherein the compound is administered topically 3.17. Fluralaner for use in protecting a dog from a parasitic invertebrate pest (ticks, flea or mite), wherein the compound is administered orally after or concurrently with a meal.

3.18. Fluralaner for use in protecting a dog from a parasitic invertebrate pest (ticks, flea or mite), wherein the compound is administered on a tailored to need posology.

3.19. A method for protecting an animal from a parasitic invertebrate pest comprising orally or parenterally administering to the animal a pesticidally effective amount of fluralaner, an N-oxide, a salt or an enantiomer thereof, wherein the compound is administered orally, wherein the compound is administered 4 hours prior to a walk in a dangerous environment.

3.20. A method for protecting an animal from a parasitic invertebrate pest comprising orally or parenterally administering to the animal a pesticidally effective amount of fluralaner, an N-oxide, a salt or an enantiomer thereof), wherein the compound is administered orally after or concurrently with a meal.

3.21. A method for protecting an animal from a parasitic invertebrate pest comprising orally or parenterally administering to the animal a pesticidally effective amount of fluralaner, an N-oxide, a salt or an enantiomer thereof), wherein the compound is administered on a tailored to need posology.

3.22. Method for protecting an animal from a parasitic invertebrate pest, comprising using any of the compounds of formulations of embodiments 3.1 to 3.18.

3.23. Method of embodiment 3.22, comprising using the method of any of the previous embodiments.

3.24. Method of embodiments 3.19 to 3.23, comprising using the compound or composition of any of the previous embodiments.

4 Fluralaner New Therapeutic Indication Embodiments 4.1. Fluralaner for use in protecting an animal from a parasitic invertebrate pest, wherein said animal is a senior dog.

4.2. Fluralaner for use in protecting an animal from a parasitic invertebrate pest, wherein said animal is a lactose intolerant dog.

4.3. Fluralaner for use in protecting an animal from a parasitic invertebrate pest, wherein said animal is a large breed dog.

4.4. Fluralaner for use in protecting an animal from a parasitic invertebrate pest, wherein said animal is a lactose intolerant dog, wherein fluralaner is administered to said animal at a reduced dosage.

4.5. Fluralaner for use in protecting an animal from a parasitic invertebrate pest, wherein said animal is a large breed dog, wherein fluralaner is administered to said animal at a reduced dosage, said reduced dosage being comprised between 0.025 mg/kg and 12.5 mg/kg, more preferably between 0.5 mg/kg and 9.37 mg/kg.

4.6. Fluralaner for use in protecting an animal from a parasitic invertebrate pest, wherein said invertebrate pest is selected from the list consisting of: flies such as *Haematobia* (Lyperosia) *irritans* (horn fly), *Stomoxys calcitrans* (stable fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus instestinalis, Gastrophilus haemorrhoidalis*, and *Gastrophilus naslis*; lice such as *Bovicola* (*Damalinia*) *bovis, Bovicola equi, Haematopinus asini, Felicola subrostratus, Heterodoxus spiniger, Lignonathus setosus* and *Trichodectes canis*; keds such as *Melophagus ovinus*; mites such as *Psoroptes* spp., *Sarcoptes scabei, Chorioptes bovis, Demodex equi, Cheyleitellia* spp., *Notoedres cati, Trombicula* spp. and *Otodectes cyanotis* (ear mites); ticks such as *Ixodes* spp., *Boophilus* spp., *Rhipicephalus* spp., *Amblyomma* spp., *Dermacentor* spp., *Hyalomma* spp. and *Haemaphysalis* spp.; and fleas such as *Ctenocephalides felis* (cat flea) and *Ctenocephalides canis* (dog flea).

4.7. A method for protecting an animal from a parasitic invertebrate pest, wherein said invertebrate pest is selected from the list consisting of: flies such as *Haematobia* (Lyperosia) *irritans* (horn fly), *Stomoxys calcitrans* (stable fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus instestinalis, Gastrophilus haemorrhoidalis*, and *Gastrophilus naslis*; lice such as *Bovicola* (*Damalinia*) *bovis, Bovicola equi, Haematopinus asini, Felicola subrostratus, Heterodoxus spiniger, Lignonathus setosus* and *Trichodectes canis*; keds such as *Melophagus ovinus*; mites such as *Psoroptes* spp., *Sarcoptes scabei, Chorioptes bovis, Demodex equi, Cheyleitellia* spp., *Notoedres cati, Trombicula* spp. and *Otodectes cyanotis* (ear mites); ticks such as *Ixodes* spp., *Boophilus* spp., *Rhipicephalus* spp., *Amblyomma* spp., *Dermacentor* spp., *Hyalomma* spp. and *Haemaphysalis* spp.; and fleas such as *Ctenocephalides felis* (cat flea) and *Ctenocephalides canis* (dog flea), comprising orally or parenterally administering to the animal a pesticidally effective amount of fluralaner, an N-oxide, a salt or an enantiomer thereof, wherein fluralaner is administered at a dosage comprised between 10 and 100 μg/kg/day, preferably at a dosage comprised between 20 and 50 μg/kg/day, even more preferably at a dosage comprised between 30 and 40 μg/kg/day and wherein fluralaner is administered at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92 times in a period of one week or 1, 2, or 3 months to said animal at a reduced dosage, more preferably in a period of 3 months to said animal.

4.8. Fluralaner for use in soothing an animal, wherein soothe is obtained by the efficient treatment of said animal against a parasiticide.

4.9. Composition containing a calming compound (as for example a pheromone) and fluralaner for use in soothing an animal, wherein soothe is obtained by the efficient treatment of said animal against a parasiticide.

4.10. Fluralaner for use in treating an environment against a pest, wherein said treatment is obtained by administering an efficient amount of fluralaner to a target species, wherein the target specie is a canine or a feline.

4.11. Fluralaner for use in eliminating parasites in an environment, wherein the treatment of the environment is obtained by administering an effective amount of fluralaner to a target specie, wherein the target specie is cattle and wherein the environment is a cattle barn.

4.12. Fluralaner for use in eliminating parasites in an environment, wherein the treatment of the environment is obtained by administering an effective amount of fluralaner to a target specie, wherein the target specie is a domestic cat or a domestic dog and wherein the environment is a house and wherein the parasites are fleas.

4.13. Method for protecting an animal from a parasitic invertebrate pest, comprising using any of the compounds of formulations of embodiments 4.1 to 4.12.

4.14. Method of embodiment 4.13, comprising using the method of any of the previous embodiments.

4.15. Method of embodiments 4.13 or 4.14, comprising using the compound or composition of any of the previous embodiments.

5 Fluralaner New Combination Embodiments 5.1. Combination of fluralaner, flumethrin and imidacloprid for use in protecting an animal from a parasitic invertebrate pest, wherein said combination is active against ectoparasites and endoparasites.

5.2. An insecticidal, miticidal, nematicidal, molluscicidal, microbicidal or bactericidal composition comprising at least two types of active compounds with amounts that are synergistically active, wherein the two types of active compound include: fluralaner and an IGR (insect growth regulator).

5.3. An insecticidal, miticidal, nematicidal, molluscicidal, microbicidal or bactericidal composition comprising at least two types of active compounds with amounts that are synergistically active, wherein the two types of active compound include: fluralaner and lufenuron.

5.4. An insecticidal, miticidal, nematicidal, molluscicidal, microbicidal or bactericidal composition comprising at least two types of active compounds with amounts that are synergistically active, wherein the two types of active compound include: fluralaner, flumethrin and imidacloprid.

5.5. Fluralaner for use in protecting a dog from a parasitic invertebrate pest (ticks, flea or mite), wherein the compound is administered orally, in combination with or formulated in a fat containing device.

5.6. Method for protecting an animal from a parasitic invertebrate pest, comprising using any of the compounds of formulations of embodiments 5.1 to 5.5.

5.7. Method of embodiment 5.6, comprising using the method of any of the previous embodiments.

5.8. Method of embodiment 5.6 or 5.7, comprising using the compound or composition of any of the previous embodiments.

5.9. Compound, composition or method of any of the previous embodiments, comprising an additional active ingredient in the formulation.

5.10. Composition or method of any of the previous embodiments, wherein the additional active ingredient is a complementary active ingredient in the formulation.

5.11. Composition or method of the previous embodiment, wherein the additional active ingredient is a useful and compatible active ingredient in order to enlarge the spectrum of activity.

5.12. Composition or method of any of embodiments 5.9-5.11, wherein the additional active ingredient increases the efficacy against parasites of the animals.

5.13. Composition or method of any of embodiments 5.9-5.12, wherein synergy on the fluralaner effect or on the other(s) active(s) effect(s)) occurs while using effective amount of fluralaner and lesser amount of the other(s) active(s), or while using lesser amount of fluralaner and effective amount of the other(s) active(s).

6 Fluralaner Smart Devices and Methods Embodiments 6.1. Anti-flea and anti-tick external smart device for a pet, such as a collar, to ensure more than four, preferably more than five, more preferably more than six and even more preferably more than eight months of efficacy of greater than 95% against fleas, as determined in a test providing the reinfestation of the pet with 100.±.10 fleas, and more than three months of efficacy of greater than 90% against ticks, as determined in a test providing the reinfestation of the pet with 50.±.3 three ticks, comprising a matrix in which is incorporated from 1 to 15% by weight, relative to the external device, of at least one substance which is active against fleas and ticks, this at least one active substance being fluralaner.

6.2. The external device according to the previous embodiment, wherein fluralaner is administered to said animal at a reduced dosage.

6.3. The external device according to any of embodiments 6.1-6.2, wherein the collar comprises from 2.5 to 5% active substance.

6.4. The external device according to any of embodiments 6.1-6.3, wherein the collar comprises from 1.25 to 10% active substance.

6.5. The external device according to any of embodiments 6.1-6.4, wherein the efficacy is maintained when the collar or external device is taken off or lost, over a period ranging from 2 to 3 months against fleas and from 1 to 2 months against ticks.

6.6. The external device according to any of embodiments 6.1-6.5, wherein it comprises a concentration of active substance which ensures effective protection against fleas for a period longer than or equal to 12 or 18 months.

6.7. The external device according to any of embodiments 6.1-6.6, wherein it comprises a concentration of active substance which ensures effective protection against ticks for a period longer than or equal to 12 or 15 months.

6.8. Anti-flea and anti-tick device according to any of embodiments 6.1-6.2, wherein the device ensures more than six months of efficacy against fleas and more than three months of efficacy against ticks.

6.9. Method for eliminating fleas and ticks from pets to ensure more than six months of efficacy of greater than 95% against fleas, as determined in a test providing the reinfestation of the pet with 100.±.10 fleas, and more than three months of efficacy of greater than 90% against ticks, as determined in a test providing the reinfestation of the pet with 50.±0.3 three ticks, comprising attaching to the pets at least one external smart device having a matrix into which is incorporated fluralaner.

6.10. Method according to the previous embodiment, wherein the compound by weight is present in a concentration of from 1.25 to 10%.

6.11. Method according to any of embodiments 6.9-6.10, wherein the compound by weight is present in a concentration of from 2 to 6%.

6.12. Method according to any of embodiments 6.9-6.11, wherein the compound of formula (I) is present in a proportion of from 2.5 to 5% by weight.

6.13. Method according to any of embodiments 6.9-6.12, wherein the efficacy is greater than 98% or 99% against fleas.

6.14. Method according to any of embodiments 6.9-6.13, wherein the efficacy is greater than 90% against ticks.

6.15. Method according to any of embodiments 6.9-6.14, wherein the efficacy is longer than or equal to 12 months against fleas.

6.16. Method according to any of embodiments 6.9-6.15, wherein the efficacy is longer than or equal to 18 months against fleas.

6.17. Method according to any of embodiments 6.9-6.16, wherein the efficacy is longer than or equal to 12 months against ticks.

6.18. Method according to any of embodiments 6.9-6.17, wherein the efficacy is longer than or equal to 15 months against ticks.

6.19. Method according to any of embodiments 6.9-6.18, wherein the efficacy is maintained when the external device is taken off or lost, over a period ranging from 2 to 3 months against fleas and from 1 to 2 months against ticks.

6.20. A method for distributing an active agent over a pet's body and/or in sebaceous glands of the pet and thereby control fleas and ticks on or eliminate fleas and ticks from the pet to ensure more than four, preferably more than five, more preferably more than six and even more preferably more than eight months of efficacy of greater than 95% against fleas, as determined in a test providing the reinfestation of the pet with 100.±.10 fleas, and more than three months of efficacy of greater than 90% against ticks, as determined in a test providing the reinfestation of the pet with 50.±0.3 ticks, comprising attaching to the pet a collar having a matrix into which is incorporated from 0.1 to 40% by weight, relative to the collar, of the active agent against fleas and ticks, wherein this active agent comprises at least one compound corresponding to formula (I) which is fluralaner.

6.21. A method for distributing an active agent over a pet's body and/or in sebaceous glands of the pet and thereby control fleas and ticks on or eliminate fleas and ticks from the pet to ensure more than four, preferably more than five, more preferably more than six and even more preferably more than eight months of efficacy of greater than 95% against fleas, as determined in a test providing the reinfestation of the pet with 100.±0.10 fleas, and more than three months of efficacy of greater than 90% against ticks, as determined in a test providing the reinfestation of the pet with 50.±0.3 ticks, comprising attaching to the pet a collar having a matrix into which is incorporated from 0.1 to 40% by weight, relative to the collar, of the active agent against fleas and ticks, wherein this active agent comprises Fluralaner.

6.22. The method of any of embodiments 6.20-6.21, wherein the active agent is present in an amount of from 1 to 15% by weight.

6.23. The method of any of embodiments 6.20-6.22, wherein the active agent is present in an amount of from 1.25 to 10% by weight.

6.24. The method of any of embodiments 6.20-6.23, wherein the active agent is present in an amount of from 2 to 6% by weight.

6.25. The method of any of embodiments 6.20-6.24, wherein the active agent is present in an amount of from 2.5 to 5% by weight.

6.26. The method of any of embodiments 6.20-6.25, wherein the active agent is present in an amount of from 1.25 to 10% by weight.

6.27. The method of any of embodiments 6.20-6.26, wherein the efficacy is at least 12 months against fleas.

6.28. The method of any of embodiments 6.20-6.27, wherein the efficacy is at least 18 months against fleas.

6.29. The method of any of embodiments 6.20-6.28, wherein the efficacy is at least 12 months against ticks.

6.30. The method of any of embodiments 6.20-6.29, wherein the efficacy is at least 15 months against ticks.

6.31. The method of any of embodiments 6.20-6.30, wherein the efficacy is maintained over periods of from 2 to 3 months against ticks and from 1 to 2 months against ticks after the collar is removed.

The invention claimed is:

1. A method of protecting an animal from a parasitic invertebrate flea or tick pest, comprising administering daily to an animal a pesticidally effective amount of fluralaner at a fluralaner dosage of from 20 to 50 μg/kg/day, wherein the animal is a dog, and wherein a plasma concentration of at least 150 ng/ml is reached in about 5-7 days.

2. The method of claim 1, wherein the fluralaner is administered at a fluralaner dosage in a range of from 30 and 40 μg/kg/day.

3. The method of claim 1, wherein the fluralaner is administered daily according to a fluralaner dosage regimen comprising (i) an initial fluralaner dose D0, administered at the beginning of treatment, representing at most 65% of a determined total fluralaner dose, and (ii) a plurality of maintenance fluralaner doses Di, administered sequentially during a duration of the treatment, a sum of the fluralaner Di doses and of the fluralaner D0 dose being equal to the determined total fluralaner dose.

4. The method of claim 3, wherein the initial fluralaner dose D0 is in a range of from 0.5% to 60% of the determined total fluralaner dose.

5. The method of claim 3, wherein each maintenance fluralaner dose Di represents at most 35% of the initial fluralaner dose D0.

6. The method of claim 3, wherein the fluralaner dosage is administered by means of a controlled-release device.

7. The method of claim 6, wherein the fluralaner dosage is administered by a smart collar.

8. The method of claim 6, wherein the fluralaner dosage is administered orally.

9. The method of claim 6, wherein the fluralaner dosage is administered by an implant.

10. The method of claim 6, wherein the fluralaner dosage is administered by a soft chewable veterinary pharmaceutical composition for oral administration comprising fluralaner, a solid carrier and a solvent.

11. The method of claim 10, wherein the solvent is DMSO (dimethylsulfoxide).

12. The method of claim 6, wherein the dosage of the fluralaner is sufficient to provide at least 50% efficiency against the parasitic invertebrate pest.

* * * * *